(12) United States Patent
Draper et al.

(10) Patent No.: US 6,310,044 B1
(45) Date of Patent: *Oct. 30, 2001

(54) OLIGONUCLEOTIDE THERAPIES FOR MODULATING THE EFFECTS OF HERPESVIRUSES

(75) Inventors: Kenneth G. Draper, San Marcos; David J. Ecker, Carlsbad; Christopher K. Mirabelli, Encinitas; Stanley T. Crooke, Carlsbad, all of CA (US)

(73) Assignee: Isis Pharmaceuticals, Inc., Carlsbad, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 07/852,132

(22) PCT Filed: Feb. 25, 1991

(86) PCT No.: PCT/US91/01327

§ 371 Date: Apr. 28, 1992

§ 102(e) Date: Apr. 28, 1992

(87) PCT Pub. No.: WO91/12844

PCT Pub. Date: Sep. 5, 1991

Related U.S. Application Data

(63) Continuation-in-part of application No. 07/485,297, filed on Feb. 26, 1990, now Pat. No. 5,248,670.

(51) Int. Cl.$^7$ .......................... A61K 48/00; C07H 21/04; C12Q 1/68; C12P 19/34

(52) U.S. Cl. .......................... 514/44; 536/24.1; 536/24.5; 435/6; 435/91.1; 435/366

(58) Field of Search .............................. 514/44; 536/24.5, 536/24.1; 935/6, 9, 11, 14, 34; 435/6, 91.1, 366

(56) References Cited

U.S. PATENT DOCUMENTS

| | | | |
|---|---|---|---|
| 4,689,320 | * 8/1987 | Kaji | 514/44 |
| 4,757,055 | * 7/1988 | Miller et al. | 514/44 |
| 4,806,463 | * 2/1989 | Goodchild et al. | 435/5 |
| 5,248,670 | * 9/1993 | Draper et al. | 514/44 |

OTHER PUBLICATIONS

W. James, Antiviral Chem. & Chemotherapy, vol. 2(4), ('91) 191–214.*
J. Milligan et al., J. Med. Chem., 36 (14) ('93) 1923–37.*
T. Gura et al., Science, 270 (27 on '95) 575–577.*
C. Stein et al. Science, vol. 261, (1993) p. 1004–1012.*
B. Tseng et al. Cancer Gene Therapy, vol. 1, No. 1 (Mar. '94) pp. 65–71.*
R. Weiss Science News, vol. 139, (Feb. 16, 1991) pp. 108–110.*
Westermann et al. Biomed. Biochim. Acta, vol. 1 (1989) pp. 85–93.*
D. McGeoch et al. J. of Virology, vol. 62, #2 (1988) pp. 443–453.*
M. Matsukura et al. PNAS, vol. 86 (1989) pp. 4244–4248.*
Uhlmann, E., et al. Chemical Reviews, vol. 90, #4 (1990) pp. 543–584.*
Preston, V., et al. Virology, vol. 167 (1988) pp. 458–467.*
Agrawal, S., et al. P.N.A.S., vol. 85 (1988) pp. 7079–7083.*
Baer et al., Nature 310:207–211 (1984).
Blair et al., J. Virol. 61:2499–2508 (1987).
Beaucage et al., "An Improved Sulfurization Reagent For The Synthesis Of Sulfur–containing Oligonucleotides" Ann. N.Y. Acad. Sc. (1989).
Brandt and Grau, Invest. Ophthalmol. Vis. Sci., 31:2214–2223 (1990).
Ceruzzi and Draper, Nucleosides and Nucleotides 8:815–818 (1989).
Cheng et al., abstract presented in Rockville, MD, published in J Biol Chem 264:11521–11526 (1989).
Davison & Scott, J. Gen. Virol. 67:1759–1816 (1987).
Draper et al., Antiviral Res. 13:151–164 (1990).
Frame et al., J. Gen. Virol. 66:1581–1587 (1985).
Grau et al., Invest. Ophthalmol. Vis. Sci., 30:2474–2480.
Iyer et al., (1990) J. Am. Chem. Soc., 112:1253–1254).
Kulka et al., Proc. Natl. Acad. Sci.USA 86:6868–6872 (1989).
Kouzarides et al., J. Virol. 61:125–133 (1987).
Lawrence et al., J. Virol. 64:287–299 (1989).
McGeoch et al., J. Gen. Virol., 69:1531–1574 (1988).
McGeoch et al., J. Mol. Biol. 181:1–13 (1985).
McGeoch et al., Nucleic Acids Res. 14:1727–1745 (1986).
Matsukura et al., Proc. Natl. Acad. Sci. USA 84:7706–7710 (1987).
Perry and McGeoch, J. Gen. Virol. 69: 2831–2846 (1988).
Smith et al., Proc. Nat'l Acad. Sci, USA, 83:2787–2792 (1986).

* cited by examiner

Primary Examiner—Andrew Wang
(74) Attorney, Agent, or Firm—Licata & Tyrrell P.C.

(57) ABSTRACT

Compositions and methods are provided for the treatment and diagnosis of herpesvirus infections. In accordance with preferred embodiments, oligonucleotides are provided which are specifically hybridizable with RNA or DNA deriving from a gene corresponding to one of the open reading frames UL5, UL8, UL9, UL13, UL29, UL30, UL39, UL40, UL42 AND UL52 of herpes simplex virus type 1. The oligonucleotide comprises nucleotide units sufficient in identity and number to effect said specific hybridization. In other preferred embodiments, the oligonucleotides are specifically hybridizable with a translation initiation site; it is also preferred that they comprise the sequence CAT. Methods of treating animals suspected of being infected with herpesvirus comprising contacting the animal with an oligonucleotide specifically hybridizable with RNA or DNA deriving from one of the foregoing genes of the herpesvirus are disclosed. Methods for treatment of infections caused by herpes simplex virus type 1, herpes simplex virus type 2, cytomegalovirus, human herpes virus 6, Epstein Barr virus or varicella zoster virus are disclosed.

10 Claims, 37 Drawing Sheets

```
base no.    1                                                                              50
    HSV-1   ATGGATGAGT  CCCGCAGACA  GCGACCTGCT  GGTCATGTGG  CAGCTAACCT
    HSV-2   ATGGATGAGT  CCGGGCGACA  GCGACCTGCT  GGTCGTGTGG  CAGCTGACAT
  Matches   ATGGATGAGT  CC-G---GACA GCGACCTGCT  GGTC-TGTGG  CAGCT-AC-T 51                                                                              100
    HSV-1   CAGCCCCCAA  GGTGCACGCC  AACGGTCCTT  CAAGGATTGG  CTCGCATCCT
    HSV-2   CAGCCCCCAA  GGTGCACACC  GACGCTCCTT  CAAGGCCTGG  CTCGGTCCT
  Matches   CAGCCCCCAA  GGTGCAC-CC  -ACG-TCCTT  CAAGG---TGG CTCGC-TCCT 101                                                                              150
    HSV-1   ACGTACACTC  CAACCCCCAC  GGGCCTCCG   CCGCTCCTCC  CACGGGTCCC
    HSV-2   ACATACACTC  CCTCAGCCGC  CGGGCGTCCG  CGGAGCCCGC  CCGGGTCCC
  Matches   AC-TACACTC  C--C---CC-C C-GGGC-TCCG C-G---CC--C C-CGGGTCCC 151                                                                              200
    HSV-1   CTCCAGGACG  CCGCCGTCTC  CCGCTCCTCC  GCCACCGATC  CGGCCCCTCT
    HSV-2   CCCCGAGACG  GCGCCGTCTC  CGGAGCCCGC  GCCGCCGATC  CGGCCCCTCC
  Matches   C-CC--GACG  -CGCCGTCTC  C-G---CC--C GCC-CCGATC  CGGCCCCTC- 201                                                                              250
    HSV-1   CGGCCTCCGC  GAGCGGCTTC  GCGCGGGACT  ATCCCGATGG  GCCACCGATC
    HSV-2   CAGCTTCCGG  GAGCGGCTTC  GCGCGGGACT  GTCCCGATGG  CGAGTGAGCC
  Matches   C-GC-TCCG-  GAGCGGCTTC  GCGCGGGACT  -TCCCGATGG  CGA-TGAGCC 251                                                                              300
    HSV-1   GCTCGTCTCA  TCGCCGCGCG  TCCCCCGAGA  CGCCCGGTAC  GGCGGCCAAA
    HSV-2   GCTCGTCTCG  TCGCCGCTCG  TCCCCCGAGG  CCCCCGGCCC  TGCGGCCAAG
  Matches   GCTCGTCTC-  TCGCCGC-CG  TCCCCCGAG-  C-CCCGG---C -GCGGCCAA-
```

*Fig. 3A*

```
        301
HSV-1   CTGAACCGCC CGCCCCTGCG CAGATCCCAG GCGGGCGTTAA CCGCACCCCC
HSV-2   CTAAGGCGCC CGCCCCTGCG CAGGTCCGAG ACGGCCATGA CCTCGCCCCC
Matches CT-A--CGCC CGCCCCTGCG CAG-TCC-AG -CGGC---T-A CC-C-CCCCC
                                                              350

351
HSV-1   CTCGTCCCCC TCGCACATCC TCACCCTCAC GCGCATCCGC AAGCTATGCA
HSV-2   GTCGCCCCCC TCGCACATCC TGTCCCTGCG GCGCATCCAC AAGCTATGCA
Matches -TCG-CCCCC TCGCACATCC T--CCCTC-C GCGCATCC-C AAGCTATGCA
                                                              400

401
HSV-1   GCCCCGTGTT CGCCATCAAC CCCGCCCTAC ACTACACGAC CCTCGAGATC
HSV-2   TCCCCGTATT CGCCGTCAAC CCCGCCCTCC GCTACACGAC CTCGGAGATC
Matches -CCCCGT-TT CGCC-TCAAC CCCGCCCT-C -CTACACGAC C----GAGATC
                                                              450

451
HSV-1   CCCGGGGCCC GAAGCTTCGG GGGGTCTGGG GGATACGGTG ACGTCCAACT
HSV-2   CCCGGGGCCC GCAGCTTCGG GGGCTCTCGG GGGTACGGCG AGGTGCAGTT
Matches CCCGGGGCCC G-AGCTTCGG GGG-TC-GGG GG-TACGG-G A-GT-CA--T
                                                              500

501
HSV-1   GATTCGCGAA CATAAGCTTG CCGTTAAGAC CATAAAGGAA AAGGAGTGGT
HSV-2   GATTCGCGAA CACAAACTCG CCGTGAAGAC CATCCGGGAA AAAGAGTGGT
Matches GATTCGCGAA CA-AA--CT-G CCGT-AAGAC CAT---GAA AA-GAGTGGT
                                                              550

551
HSV-1   TTGCCGTTGA GCTCATCGCG ACCCTGTTGG TCGGGGAGTG CGTTCTACGC
HSV-2   TGCCCGTGGA GCTCGTCGCG ACCCTGCTCG TGGGGAGTG CGCTCTTCGC
Matches TTGCCCGT-GA GCTC-TCGCG ACCCTG-T-G T-GGGGAGTG CG-TCT-CGC
                                                              600
```

*Fig. 3B*

```
         601                                                           650
HSV-1    GCCGGCCCGCA CCCACAACAT CCGCGGCTTC ATCGCGCCCC TCGGGTTCTC
HSV-2    GGCGGCCCGCA CCCACGACAT CCGCGGCTTT ATCACCCCGC TCGGGTTCTC
Matches  G-CGGCCCGCA CCCAC-ACAT CCGCGGCTT- ATC-C-CC-C TCGGGTTCTC
         651                                                           700
HSV-1    GCTGCAACAA CGACAGATAG TGTTCCCCGC GTACGACATG GACCTCGGTA
HSV-2    GCTGCAGCAG CGCCAGATCG TGTTCCCCGC GTACGACATG GACCTCGGCA
Matches  GCTGCA-CA- CG-CAGAT-G TGTTCCCCGC GTACGACATG GACCTCGG-A
         701                                                           750
HSV-1    AGTATATCGG CCAACTGGCG TCCCTGCGCA CAACAAACCC CTCGGTCTCG
HSV-2    AGTACATCGG CCAGCTGGCG TCCCTGCGCG CGACCACCCC CTCCGTCGCG
Matches  AGTA-ATCGG CCA-CTGGCG TCCCTGCGC- C-AC-A-CCC CTC-GTC-CG
         751                                                           800
HSV-1    ACGGCCCTCC ACCAGTGCTT CACGGAGCTG GCCCGCGCCG TTGTGTTTTT
HSV-2    ACGGCCCTCC ACCACTGCTT CACAGACCTG GCGGCGCCG TGGTGTTCCT
Matches  ACGGCCCTCC ACCA-CTGCTT CAC-GA-CTG GC-CGCGCCG T-GTGTT--T
         801                                                           850
HSV-1    AAACACCACC TGCGGGATCA GCCACCTGGA TATCAAGTGC GCCAACATCC
HSV-2    GAACACCAGG TGCGGGATCA GCCACCTGGA CATCAAGTGC GCCAACGTCC
Matches  -AACACCA-- TGCGGGATCA GCCACCTGGA -ATCAAGTGC GCCAAC-TCC
         851                                                           900
HSV-1    TCGTCATGCT GCGGTCGGAC GCCGTCTCGC TCCGGGGGGC CGTCCTCGCC
HSV-2    TCGTGATGCT GCGATCGGAC GCGGTGTCGC CATCAAGTGC CGTCCTGGCC
Matches  TCGT-ATGCT GCG-TCGGAC GC-GT-TCGC -ATCAAGTGC CGTCCT-GCC
```

```
        901
HSV-1   GACTTTAGCC TCGTCACCCT CAACTCCAAC TCCACGATCG CCCGGGGCA
HSV-1   GACTTTAGCC TGGTGACCCT GAACTCCAAC TCCACGATAT CCCGGGGCCA
Matches GACTTTAGCC T-GT-ACCCT -AACTCCAAC TCCACGAT-- CCCGGGG-CA
                                                          1000
HSV-1   GTTTTGCCTC CAGGAGCCGG ACCTCAAGTC CCCCCGGATG TTTGGCATGC
HSV-2   GTTTTGCCTC CAGGAGCCGG ACCTCGAGTC CCCCCGGGGG TTTGGGATGC
Matches GTTTTGCCTC CAGGAGCCGG ACCTC-AGTC CCCCCGG--G TTTGG-ATGC
        1001                                              1050
HSV-1   CCACCGCCCT AACCACAGCC AACTTTCACA CCCTGGTGGG TCACGGGTAT
HSV-2   CCGCCGCCCT GACCACGCC  AACTTTCACA CTCTGGTGGG GCACGGGTAC
Matches CC-CCGCCCT -ACCAC-GCC AACTTTCACA C-CTGGTGGG -CACGGGTA-
        1051                                              1100
HSV-1   AACCAGCCCC CGGAGCTGTT GGTGAAATAC CTTAACAACG AACGGGCCGA
HSV-2   AACCAGCCAC CGGAGCTCTC GGTAAAGTAC CTCAACAACG AGCGGGCCGA
Matches AACCAGCC-C CGGAGCT-T- GGT-AA-TAC CT-AACAACG A-CGGGCCGA
        1101                                              1150
HSV-1   ATTTACCAAC CACCGCCCTGA AGCACGACGT CGGGTTAGCG GTTGACCTGT
HSV-2   GTTTAACAAC CGCCCCCTGA AGCACGACGT CGGGCTGGCG GTCGATCTCT
Matches -TTTA-CAAC C-CC-CCTGA AGCACGACGT CGGG-T-GCG GT-GA-CT-T
        1151                                              1200
HSV-1   ACGCCCTGGG CCAGACGCTG CTGGAGTTGG TGGTTAGCGT GTACGTCGCC
HSV-2   ACGCCCTGGG GCAGACGCTG CTGGAGCTGC TGGTTAGCCT GTACGTGGCC
Matches ACGCCCTGGG -CAGACGCTG CTGGAG-TG- TGGTTAGCGT GTACGT-GCC
```

```
        1201                                                          1250
HSV-1   CCGAGCCCTGG GCGTACCCGT GACCCGGTTT CCCGGTTACC AGTATTTTAA
HSV-2   CCGAGCCCTGG GCGTCCCCGT GACCCGCGTC CCGGGCTACC AGTACTTTAA
Matches CCGAGCCCTGG GCGT-CCCGT GACCCG---T- CC-GG-TACC AGTA-TTTAA
        1251                                                          1300
HSV-1   CAACCAGCTG TCGCCGGACT TCGCCCTGGC CCTGCTCGCC TATCGCTGCG
HSV-2   CAACCAGCTC TCGCCGGACT TTGCCCGTGG CCTCCTCGCC TATCGCCGCG
Matches CAACCAGCT- TCGCCGGACT T-GCC-TGGC CCT-CTCGCC TATCGC-GCG
        1301                                                          1350
HSV-1   TGCTGCACCC AGCCCTGTTT GTCAACTCGG CCGAGACCAA CACCCACGGC
HSV-2   TTCTGCACCC CGCCCTCTTT GTCAACTCGG CCGAGACCAA CACCCACGGC
Matches T-CTGCACCC -GCCCT-TTT GTCAACTCGG CCGAGACCAA CACCCACGGC
        1351                                                          1400
HSV-1   CTGGCGTATG ACGTCCCAGA GGGCATCCCG CGCCACCTCC GCAATCCCAA
HSV-2   CTGGCGTATG ACGTGCCGGA GGGCATCCGG CGCCACCTTC GCAATCCCAA
Matches CTGGCGTATG ACGT-CC-GA GGGCATCC-G CGCCACCT-C GCAATCCCAA
```

*Fig. 3E*

```
                1401                          1450
HSV-1   GATTCGGCGC GCGTTTACGG ATCGGTGTAT CACACACACA
HSV-2   GATTCGGCGC GCGTTCACGG AGCAGTGTAT CGCACGCACA
Matches GATTCGGCGC GCGTT-ACGG A-C-GTGTAT C-CAC-CACA 1451                          1500
HSV-1   AGGCGATACT GTCGTCGGTG GCGCTGCCTC CCGAGCTTAA
HSV-2   AGGCCCGTCCT GTCGTCGGTG TCGCTGCCGC CCGAGCTGAG
Matches AGGC--T-CT GTCGTCGGTG -CGCTGCC-C CCGAGCT-A-

1501                          1550
HSV-1   GTGCTGGTGT CCCGCCTGTG TCACACCAAC CCGTGCCGCG
HSV-2   GTGCTGGTCT CCCGCCCTG  TCACGCCAAC CCGGCCGCGC
Matches GTGCTGGT-T CCCGCCT-TG TCAC-CCAAC CCG--CGCGC 1551
HSV-1   GTCGTGA
HSV-2   GTCGTGA
Matches GTCGTGA
```

*Fig. 3F*

HSV-1    1  ..TACCACAGGTGGGTGCTTTGGAAACTTGTCGGTCGCCGTGCTCCTGTG        48
HSV-2    1  ACCACAACAGGTGGGTGCTTCGGGGACTTGACGGTCGCCACTCTCCTGCG        50

49  AGC......TTGCGTCCCCTCCCCGGTTTCCTTTGCCTCTCCCGCCTTCCGGA       93
        51  AGCCCTCACGTCTTCGCCCACCGATTCCTGTTGCCGTTCCTGTGCGGCCGGT      100

94  CCTGCTCTCGCCTATCTTCTTTGGCTCTCGGTGCGATTCGTCAGGCAGCG       143
       101  GCTGTCCTGTCGACAGATTGTTGGC.GACTGCCCGGGTGATTCGTCGGCC       149

144  GCCTTGTGTCGAATCTCGACCCCACCACTCGCCCGACTCGCCGACGTCCCT      193
       150  GGTGCGTCCTTTCGGTCGTACCGCCCCACCCCGCCTCCCACGGGCCCGCCG      199

194  CTCGAGCCCGCCCGAAACCCGCCGTCTGTTGAAATGGCC                  243
       200  CTGTTTCCGTTCATCGCGTCCGAGCCACCGTCACCTTGGTTCCAATGGCC       249

244  AGCCGCCCAGCGCCCATCCCTCTCCCCGGTCGAAGCGCGGCCCCGGTTGGGGG    293
       250  AACCGCCCCTGCCGCATCCGCCCCTCGCCGGGAGCGCGGTCTCCGTCCGAACG    299

294  ACAGGAGCCGGGGCCGCCAGCGCAGCCACCCAGGGGGAGGCCGCGGGG         343
       300  ACAGGAACCCCGGGAGCCCGGAGGTCGCGAGTCGCCCCCCCTGG..........   335

*Fig. 4A*

```
344 CCCCTCTCGCCCCACGGGCCACCACGTGTACTGCCAGCGAGTCAATGGCGTG --- 393
336 ..........CGGCGACCACGTGTTTGCAGGAAAGTCAGCGGCGTG --- 372
394 ATGGTGCTTTCCGACAAGAGCGCCCGGGTCCGCGTCCTACCGCATCAGCGA --- 443
373 ATGGTGCTTTCCAGCGATCCCCCCGGCCCGCGCCTACCGCATTAGCGA --- 422
444 TAGCAACTTTGTCCAATGTGGTTCCAACTGCACCATGATCATCGACGGAG --- 493
423 CAGCAGCTTTGTTCAATGCGCTCCAACTGCAGTATGATAATCGACGGAG --- 472
494 ACGTGGTGCGGCGCCCCCAGGACCCGGGCATCCCCCGCT --- 543
473 ACGTGGCGCGCGGTCATTGCGTGACCCTGAGGCGCTACGTCCACCGGC --- 522
544 CCCTTCGTTGCGGTGACAAACATCGGAGCCGGCAGCGACGGCGGACCGC --- 593
523 ACGTGGCGCGGTCATTGCGTGACCCTGAGGCGCTACGTCCACCGGC --- 572
594 CGTCGTGGCATTCGGGGAACCCCACGTCGCTCGGCGGGACGTCTACCG --- 643
573 CGTCGTGGCGCTCGGCGAACCTCGGCCCCGTCCGGCCGGAACCGC --- 622
```

*Fig. 4B*

```
644 GTACCCAGACGGCC...GACGTCCCCACCGAGGCCCTTGGGGCCCC...   687
     ||||||||||||||   ||||||||||||||||||||||||||||
623 GGACCCAGACGGTCCGGGGAGTTCCTCCAACGGGAACCCAAGGACCCCCGAA  672

688 .........CCTCCTCCCCCGCTTCACCCTGGTGCGGCTGTGTTC         728
              |||| ||||| ||||||  |||||||||||||||
673 CCCCAAGGACCCCAGGCTGTCCCCCCGCCTCCTCCCCCCTTTCCATG       722

729 CTGTCGCGACACACGGCGCCGCTCTGCGGTATTCGGGGGAGGGGATC       778
     |||||||| |||| || |||||  ||||| ||||||||||||||||
723 GGGCCACGAGTGCTGCGCCCGCTGCGCCAGGGGGCGCCGAGAAGG         772

779 CAGTCGGCCCCCGGAGTTCGTCTCGGACACCGTCGTCCGATTCCGAC       828
     |||||||   ||||||||||  |||||  |||||| |||||||||
773 ACGTCGGGGGCCGCGGAGTCATGGTCAGAGTCGTCCCCGTCGTCCGAA      822

829 TCGGATGACTCGGA............GGACACGGACTCGGAGAC         860
     ||||||||||||||            ||||||||||||||||||
823 ACGGAGGACTCGGACTCCCTCGGACGAGGATACGGGCTCGGGTTCGGAGAC   872

861 GCTGTCACACGCCTCCGACGTGTCCGGGGCCACGTACGACGACG          910
     ||||| |||| |||| |||||||||||| ||||||||||||||
873 GCTGTCTCGATCCCTCTTCGATCTGGCCGCAGGGCGACTGACGACGATG    922

911 CCCTTGACTCCGATTCGTCATCGGATGACTCCCTGCAGATAGATGGCCCC   960
     ||||||||||||||| ||||||||||||||||||||||||||||||||
923 ACAGGCGACTCCGACTCGCGGTTCGCGGACGACTCCGTGCAGCCCGACGTTGTC  972
```

*Fig. 4C*

```
  961 GTGTGTCGCCCGTGGAGCAATGACACCGCGCCCCTGGATGTT..........    1002
      ||  |||||||| |   | || || ||||  ||| |||||
  973 GTTCGTCGCAGATGGAGCGACGGCCCTGCCCCGTGGCCTTTCCCAAGCC       1022

1003 ..........TGCCCCGGGACCCCGGCCCCGGGCGCCCGGCCGACGCCG       1036
                ||||||| || |||| |||||||   || || ||||||
 1023 CCGGCGCCCCGGCGCCCCGGCGACTCCCCCGGAAACCCGCTGGGCCACCG      1072

1037 GTGGTCCCTCAGCGGTAGACCCACACGCGACGCCAGAGGCCGGCGCT         1086
      || |||||||||||| ||| || |||||||||| |||||| ||||
 1073 GGCCGGGCTCCGCGACGGACCCCGCGCGCGCGTC..........GGCCGACTCC 1113

1087 GGTCTCTTGCGGCCACGTCTCTGGGAACGGGCACGGCCCTACCCCGTCCCCCTGG 1136
      || ||||||||  |||||| ||||| ||||| |||||| ||||| ||||||||
 1114 GATTCCGCGACGGCACGTGTGGGAACGGACGACCCCAGGCGCTACCCCAGTCCCCTAG 1163

1164 GGACCCCCGCGAGAACGCGGAGGCCCGTGGCCGCGCTTTCTGGAGATGCC       1186
      || |||| ||||||||||||||  ||||||||| |||||||||||  ||
 1187 GGACAGCGGCGAGAACGCGGAGGCGGTGGCCGCGTTTCTGGGGACGCC        1213

1214 AACTCACGCCCGAGAACGCGGAGGCCCGTGGCCGCGCTTGGCGCCTTTTGCCGGTGCCGG 1236
      ||||||||||||||||||||||||   ||||||||||     || ||||||||| |||
 1237 AACTCACGCCCGAGAACGCGGAGGCGGTGGCCGCGCC               GTGTGCCCG 1263

1264 GTGAACCGGCGAACCCGGCGCTCATGCTGGAGTACTTTTGCCGGTGCCCG       1286
      ||  |||| |  |||||| |||||||||||||||||| ||||||||||||
      GTCGACCGGGAGCCCGGCGCTCATGCTGGAGTACTTCTGTGGTGCCCCG       1313
```

*Fig. 4D*

```
1287  CGAGGAAACCAAGCGTGTCCCCCCAGGACATTCGGCAGCCCCCTCGCC  1336
      ||||||||| |||||||||||||| ||||||||||||| |||| |||
1314  CGAGGAGAGCAAGCGCGTGCCCCCACGAACCTTCGGCAGCCCCCCGCC  1363

1337  TCACGGAGGACGACTTTGGGCTTCTCAACTACGCGCTCGTGGAGATGCAG  1386
      ||||||||||||||||||||| |||||||||||||||||||||||||||
1364  TCACGGAGGACGACTTTGGGCTCCTGAACTACGCGCTCGATGCGA      1413

1414  CGCCTGTGTCTGGACGTTCCTCCGGTCCCCGAACGCATACATGCCCTA   1463
      ||||||||||||||||||||  ||||||||| |||||||||||||||
1464  CGCCTGTGCCTGGACCTTCCCCCCGTCCCCCAAGCATACACGCCCTA    1463

1437  TTATCTCAGGGAGTATGTGACGCGGCTGGTCAAGCGGGTTCAAGCCGCTGG  1486
      |||||||||||||||||  ||||||||||||||||||||||||| |||||
1464  TCATCTGAGGGAGTATGCGACGCGGCTGGTTAACGGGTTCAAACCCCTGG  1513

1487  TGAGCCGGTCCGCTCGCCCTTTACCGCATCCTGGGGGTTCTGGTGCACCTG  1536
      ||| |||||||| ||||||| |||||||||||||||||||| ||||||||
1514  TGCGGCGGTCCGCCCGCCCGCCCTGTATCGCATCCTGGGATTCTGGTTCACCTG  1563

1537  CGGATCCGGACCCGGAGGCCTCCTTTGAGGAGTGGCTGCGATCCAAGGA   1586
      |||||||| ||| ||||||||| ||||||||| ||||| ||| |||||
1564  CGCATCCGGTACCCGGAGGCCCTCTTTGAGGAATGCGATGCCCTCCAAGGA  1613

1587  AGTGGCCCTGGATTTTGGCCTTGACGGCGAAAGGCTTCGCGAGCACGAAGCCC  1636
      ||||||||||| || |||||| |||||||||||||||||||||| |||||||
1614  GGTGGACCTGGACTTCGGGCTGACGGCGAAAGGCTTCGCGAACACGAGGCCC  1663
```

Fig. 4E

```
1637  AGCTGGTGATCCTGGCCCAGGCTCTCTGGACCATTACGACTGTCTGATCCAC  1686
      |||| ||||||||||||||||||||||   ||| ||| || || ||||||||
1664  AGCTAATGATCCTGGCCCAGGCCCTGAACCCCTGAACCCTACGACTGTCTGATCCAC  1713

1687  AGCACACCGCACACGCTGGTCGAGCGGGGCTGCAATCGGCCCTGAAGTA  1736
      |||||  |||  ||||||||||||||||||||| |||||||||||||||
1714  AGCACCCCGAACACGCTCGTCGAGCGGGGCTGCAGTCGGCCCTGAAGTA  1763

1737  TGAGGAGTTTACCTAAAGCGTTTTGGCGGCACTACATGGAGTCCGTCT  1786
      || || ||||||||| |||   |||||||||||||||||||||||||
1764  CGAAGAGTTTACCTCAAGCGCTTCGGCGGCACTACATGGAGTCCGTCT  1813

1787  TCCAGATGTACACCCGCCATCGCCCGGCTTTTGGCCTGCCGGGCCACGCGC  1836
      ||||||||||||||||||||||||||||| || |||||||||||| |||
1814  TCCAGATGTACACCCGCCATCGCCCGGGTTCCTGGCGTGCCGGGCGACCCGC  1863

1837  GGCATGCGCCACATCGCCCTGGGGCGAGAGGGTCGTGGTGGGAAATGTT  1886
      ||||||||||||||||||||||||||  |||||||||||||||||||||
1864  GGCATGCGCCACATCGCCCTGGGGCGACAGGGGTCGTGGTGGGAAATGTT  1913

1887  CAAGTTCTTTTTCCACCGCCCTCTACGACCACCAGATCGTACCGTCGACCC  1936
      ||||||||| || |||||||| |||||||||||||||||||||||||||
1914  CAAGTTCTTTTTCCACCGCCTCTACGACCACCAGATCGTGCCGTCCACCC  1963

1937  CCGCCATGCTGAACCTGGGACCCGCAACTACTACACCTCCAGCTGCTAC  1986
      |||||||||||||||||||  |||||||||||||||| |||||||||||
1964  CCGCCATGCTGAACCTCGGAACCCGCAACTACTACACGTCCAGCTGCTAC  2013
```

*Fig. 4F*

```
1987  CTGGTAAACCCCCAGGCCACCACAAACAAGGCGACCCTGCGGGCCATCAC  2036
      ------------------------------------------------
      CTGGTAAACCCCCAGGCCACCACAAACAAGGCGACCCTGCGGGCCATCAC  2063

2037  CAGCAACGTCAGTGCCATCCTCGCCCGCAACGGGGGCATCGGGCTATGCG  2086
      ------------------------------------------------
2064  CGGCAACGTGAGCGCCATCCTCGCCCGCAACGGGGCATCGGGCTGTGCA  2113

2087  TGCAGGCGTTTAACGACTCCGGCCCCCCGGGACCGCCAGCGTCATGCCCGCC  2136
      ------------------------------------------------
2114  TGCAGGCGTTCAACGACGACGGCCCCAGCCGCCACCGCCATCATGCCGGCC  2163

2137  CTCAAGGTCCTTGACTCGGTGGCGCGCCGTGGCGCACAACAAAGAGAGCGCG  2186
      ------------------------------------------------
2164  CTGAAGGTCCTGGACTCCCTGGTGGCGCGCCACAACAAACAGAGCACGCG  221

2187  TCCGACCGGCGCGTGCCGTGTACCTGGAGCCGTGGCACACCGACGTGCGGG  2236
      ------------------------------------------------
2214  CCCCACCGGGGCGTGCCGTGTACCTGGAACCCTGGCACACAGCGACGTTCGGG  2263

2237  CCGTGCTCCGGATGAAGGGGTCCTCGCCGGCGAAGAGGCCCAGCGCTGC  2286
      ------------------------------------------------
2264  CCGTGCTCAGAATGAAGGGCGTCCTCCGCCGGCGAGGAGGCCCAGCGCTGC  2313

2287  GACAATATCTTCAGCGCCCTCTGGATGCCAGACCTGTTTTTCAAGCGCCT  2336
      ------------------------------------------------
2314  GACAACATCTTCAGCGCCCTCTGGATGCCGGACCTGTTCTTCAAGCGCCT  2363
```

*Fig. 4G*

```
2337 GATTCGCCACCTGGACGGCGAGAAGAACGTCACATGGACCCTGTTCGACC 2386
     ||||:|||||||||||||||||||||||||||||||||||:|||||||||
2364 GATCCGCCACCTCGACGGCGAGAAAAACGTCACCTGTCCCTGTTCGACC 2413

2387 GGGACACCAGCATGTCGCTCGCCGACTTTCACGGGAGGAGTTCGAGAAG 2436
     ||||||||||||||||||||||||||||||||||||||||||||||||
2414 GGGACACCAGCATGTCGCTCGCCGACTTTCACGGGAGGAGTTCGAGAAG 2463

2437 CTCTACCAGCACCTCGAGTTCATGGGGTTCGGCGAGCAGATACCCATCCA 2486
     |||:||||||||||||||||||||||:|||||||||||||||:|||||
2464 CTGTACGAGCACCTCGAGGCCATGGGGTTCGGCGAAACGATCCCCATCCA 2513

2487 GGAGCTGGCCTATGGCATTGTGCCAGTACCGGACCGCCACGGGAGCCCCT 2536
     ||||||||||||||||||||||||||||||||||||||||||||||:||
2514 GGACCTGGCGTACGCCATCGTGCCAGCGCGGCCACCGGAAGCCCCT 2563

2537 TCGTCATGTTCAAAGACGCGGGTGAACCGCCACTACATCTACGACACCCAG 2586
     ||||||:|||:|||||||||||||||||||||||||||||||||||||||
2564 TCATCATGTTTAAGGACGCGGTAAACCGCCACTACATCTACGACACGCAA 2613

2587 GGGGCGGCCATCGCGCCGGCTCCAACCTCTGCACCGAGATCGTCCATCCGGC 2636
     |||:|||||||:|||||||||||||||||||||||||||||||||||||
2614 GGGCGGCCATTGCGCCGGCTCCAACCTCTGCACGGAGATCGTCCACCCGTC 2663

2637 CTCCAAGCGATCCAGTGGGTCTGCAACCTGGGAAGCGTGAATCTGGCCC 2686
     ||||||:|||||||||||||||||||||||||||:|||||||||||||
2664 CTCCAAACGCTCCAGCGGGTCTGCAACCTGGGCAGCGTGAATCTGGCCC 2713
```

Fig. 4H

```
2687  GATGCGTCTCCAGGCAGAGACGTTTGACTTTGGGGGCTCCGGCGACGCCGTG   2736
2714  GATGCGTCTCCCCGGGGGACGTTCGATTTTGGCATGCTCCGACGCCGTG      2763
2737  CAGGCGTGCGTGCTGATGGTGAACATCATGATCGACAGCACGCTACAACC     2786
2764  CAGGCGTGCGTGCTAATGGTTAATATCATGATAGACAGCACGCTGCAGCC     2813
2787  CACGCCCCAGTGCACCCCGGCAACGACAACCTGCCGTCCATGGGAATCG      2836
2814  GACGCCCCAGTGCGCGGCCCCGGCCACGACAACCTGCCGTCCATGGGCATTG   2863
2837  GCATGCAGGGCCTGCACACGGCCTGCCTGAAGCTGGGGCTGGATCTGGAG     2886
2864  GCATGCAGGGCCTGCACACGGCCGTGCCTGAAGATGGGCCTGGATCTGGAG    2913
2887  TCTGCCGAATTTCAGGACCTGAAACAAACACATCGCCGAGGTGATGCTGCT    2936
2914  TCGGCCGAGTTCCGGGACCTGAAACATCGCCGAGGTGATGCTGCT          2963
2937  GTCGGCGATGAAGACCAGCAACGCGCTGTGCCTTCGCGGGCCCGTCCCT      2986
2964  CGCGGCCATGAAGACCAGTAACGCGCTGTGCCGTTCGCGGGGCCGTCCCT     3013
2987  TCAACCACTTTAAGCGCAGCATGTATCGCGGCCGCTTTCACTGGGAG        3036
3014  TCAGCCCACTTTAAGCGCAGCATGTACCGCGGCCGCTTTCACTGGGAG       3063
```

Fig. 4I

```
3037 CGCTTTCCGGACGCCCGGCCCGGTACGAGGGCGAGTGGGAGATGCTACG 3086
3064 CGCTTTTCGAACGCGCCAGCCCGCGTACGAGGGCGAGTGGGAGATGCTACG 3113
3087 CCAGAGCATGATGAAACACGGCCTGCGCAACAGCCAGTTTGTCGCGCTGA 3136
3114 CCAGAGCATGATGAAACACGGCCTGCGCAACAGCCAGTTCATCGCGCTCA 3163
3137 TGCCCACCGCCCGCCTCGGCGCAGATCTCGGACGTCAGCGAGGGCTTTGCC 3186
3164 TGCCCACCGCCCGCCTCGGCCCAGATCTCGGACGTCAGCGAGGGCTTTGCC 3213
3187 CCCCTGTTCAACCAACCTGTTCAGCAAGGTGACCCGGGACGGCGAGACGCT 3236
3214 CCCCTGTTCAACCAACCTGTTCAGCAAGGTGACCAGGACGGCGAGACGCT 3263
3237 GCGGCCTCCTGGAGGTGATGGACAGTCTCCTGCTAAAGGAACTGAAACGCACGTTTAGCGGGA 3286
3264 GCGCCCCAACACGCTCTTGCTGAAGGAACTCGAGCGCACGTTCGGCGGGA 3313
3287 AGCGGCTCCTGGAGGTGATGGACAGTCTCGACGCCAAGCAGTGGTCCGTG 3336
3314 AGCGGCTCCTGGAGGTGATGGACAGTGGTCGAGCGCAGCAGTGGTCTGTG 3363
```

*Fig. 4J*

```
3337  CCGCAGGCGCTCCCGTGCCTGGAGCCCACCCCCTCCGGCGATTCAA  3386
      |||  |||| ||| ||||||||| ||||| |||||||||  ||||
3364  GCCCAGGCCCTGCCTTGCCTGGACCCCGCCCCCTCCGGCGGTTCAA  3413

3387  GACCGCGTTTGACTACGACCAGAAGTTGCTGATCGACCTGTGTGCCGACC  3436
      || |||| ||||||||||||||| || ||||||||||||||||||| |||
3414  GACGGCCTTCGACTACGACCAGGAACTGCTGATCGACCTGTGTGCAGACC  3463

3437  GCGCCCCCTACGTCGACCATAGCCAATCCATGACCCTGTATGTCACGGAG  3486
      ||||||||| ||| |||||| |||||||||||||| |||||||||| |||
3464  GCGCCCCCTATGTTGATCACAGCCAATCCATGACTCTGTATGTCACAGAG  3513

3487  AAGGGCGACGGGACCCCTCCCAGCCCTCCACCCCTGGTCCCTTCTGGTCCA  3536
      ||||| ||||||||| ||||||||| ||||||||||||||| ||||||||
3514  AAGGGCGACGGGACGCGCTCCCCGCGCTCCACCCCTGGTCCCGCTTCGTCCA  3563

3537  CGCATATAAGCGCGGACTAAAAACAGGGATGTACTACTGCAAGGTTCGCA  3586
      |||||||||||||||||| ||||||||| ||||||||||||||||||||
3564  CGCATATAAGCGCGGCCTGAAGACGGGGATGTACTACTGCAAGGTTCGCA  3613

3587  AGGCGACCAACAGCGGGTCTTTGGCGGACGACAACATTGTCTGCATG  3636
      |||||||||||||||||| |||||||||||||||||||||||| |||
3614  AGGCGACCAACAGCGGGTGTTCGCGGACGACAACATCGTCTGCACA  3663

3637  AGCTGCGCGCTGTGA  3651
      ||||||||||||| |
3664  AGCTGCGCGCTGTAA  3678
```

*Fig. 4K*

```
HSV-1    1 GTACTACTGCAAGGTTCGCCAACAGCGGGGTGTTCGCCGGCG    50
HSV-2    1 ..ACTACTGCAAGGTTCGCGACCAACAGCGGGTCTTTGGCGGCG   48

51 ACGACAACATCGTCTGCACAAGCTGCGCGCTGTAAGCAACA...GCGCTC  97
        49 ACGACAACATTGTCTGCAC.GGCTGCGCGCTGTGACCGACAAACCCCCTC  97

98 CGATCGGGGTCAGGCCGTCGCTCTCGGTCCCGCATATCG..........  135
        98 CGGCCCAGGCCCGCCCGCCACTGTCGTCGCCGTCCCCACGCGCTCCCCGCT 147

136 ..........C[ATG]GATCCCGCGTCTCCCCCCGCGAGCACCGACCCCCT 175
       148 GCC[ATG]GATTCCGCGCCCCAGCCCCCTCCCCCGCTCTGACGGCCCATAC  197

176 AGATACCCACGCGGTCGGGGCCGGAGATTCCGGTGTGCCCCA         225
       198 GGGCCATAGCGCGACGCGGAGACCTAGCGATTCCAGATTCCAAAGTGCCCCG 247

226 CCCCCGAGCGGTACTTCTACACCTCCCCAGTGCCCCGACATCAACCACCTT 275
       248 ACCCCGAGAGGTACTTCTACACCTCCCCAGTGTCCCGACATTAACCACCTG 297

276 CGCTCCCCTCAGCATCCTGAACCTGGCTGGAGACCGAGCTCGTGTTCGT   325
       298 CGCTCCCCTCAGCATCCTTAACCGTGGCTGGAAACCGAGCTTGTTTTCGT  347
```

Fig. 5A

```
326  GGGGGACGAGGAGGACGTCTCCAAGCTCTCCGAGGGCGAGCTCGGCTTCT  375
348  GGGGGACGAGGAGGACGTCTCCAAGCTCTCCGAGGGCGAGCTCAGCTTTT  397
376  ACCGCTTTCTGTTTGCCTTCTCCTGTCGCGGACGACCTGGTGACGGAA   425
398  ACCGCTTCCTCTTCGCTTTCTCCTGTCGCGGACGACCTGGTTACGGAA   447
426  AACCTGGGCGGCCCTCTCCGGCCTCTTCGAACAGAAGGACATTCTTCACTA  475
448  AACCTGGGCGGCCCTCTCCGGCCTGTTTGAGCAGAAGGACATTCTCCACTA  497
476  CTACGTGGAGCAGGAATGCATCGAGGTCGTCCACTCGCGCGTCTACAACA  525
498  CTACGTGGAGCAGGAATGCATCGAAGTCGCACACTCGGCGCGTGTACAACA  547
526  TCATCCAGCTGGTGCTCTTTCACAACAACGACCAGGCCCGGCCTAT    575
548  TCATCCAGCTGGTGCTTTTCCACAACAACGACCAGGCCCGCGAGTAC   597
576  GTGGCCCGCACCATCAACCACCCGGCCATTCGCGTCAAGGTGGACTGGCT  625
598  GTGGCCCGGCACCATCAACCACCCGGCCATCCGCGCCAAGGTGGACTGGCT  647
626  GGAGGCGCGGGTGCGGGAATGCGACTCGATCCCGGAGAAGTTCATCCTCA  675
648  GGAAGCGCGGGTGCGGGAATGCGCCTTCCGTTCCGGAAAAGTTCATTCTCA  697
```

*Fig. 5B*

```
676  TGATCCTCATCGAGGGCGTCTTTTTGCCGCCTCGTTCGCCATCGCG  725
     ----------------------------------------------
698  TGATCCTCATCGAGGGCATCTTTTTGCCGCCTCGTTTGCCATCGCC  747
       .         .         .         .         .
726  TACCTGCGCACCAACAACCTCCTGCGGTCACCTGCCAGTCGAACGACCT  775
     ------------------------------------------------
748  TACCTTGCGCACCAACAACCTTCTGCGGGTCACCTGCCAGTCAAACGACCT  797
       .         .         .         .         .
776  CATCAGCCGCGACGAGGCCGTGCATACGACAGCCTCGTGCTACATCTACA  825
     --------------------------------------------------
798  CATCAGCCGCGACGAGGCCGTGCACACGACGGCCTCGTGTTACATCTACA  847
       .         .         .         .         .
826  ACAACTACCTCGGGGAGGCGGTCCAAGCCCAAGAGGCGGCGTGTACCGG  875
     -------------------------------------------------
848  ACAACTACCTCGGGGCGGTCCAAGCACCCCGACCGGCGTGTACGGG  897
       .         .         .         .         .
876  CTGTTTCGGGAGGCGGTGGATATCGAGAGATCGGGTTCATCCGATCCCAGGC  925
     ---------------------------------------------------
898  CTGTTCCGCCAGGCGGTCGAGATCGGAGATCGGATTTATCCGATCCCAGGC  947
       .         .         .         .         .
926  CCCGACGACAGCTCTATCCTGAGTCCGGGGCCTGGCGGCCATCGAGA  975
     -----------------------------------------------
948  GCCGACGACAGCCATATCCTGAGCCCGGCGGCCTGGCGGCCATCGAAA  997
       .         .         .         .         .
976  ACTACGTGCGATTCAGCGCGGATCGCCTGGGCCTGATCCATATGCAG  1025
     -----------------------------------------------
998  ACTACGTGCGATTCAGCGCGGATCGCCTGTTGGGCCTTATCCACATGAAG  1047
```

*Fig. 5C*

```
1026 CCCCTGTATTCCGCCCCCCGACGCGCCCCCCGACGCGGCCAGCTTCCCCTCAGCCTCAT 1075
        ||||||||||||||  ||  |||||||||  ||  ||||||||||||| ||||||||
1048 CCACTGTTTTCCGCCCCCACCCCCGACGCCAGCTTCCGCTGAGCCTCAT 1097

1076 GTCCACCGACAAACACACCAACTTCTTCGAGTGCCGCAGCACCTCGTACG 1125
     |||||||||||||||||||||||||| |||||||||||||||||||||
1098 GTCCACCGACAAACACACCAATTTTTCGAGTGTCGCAGCACCTCCTACG 1147

1126 CCGGGGCCGTCGTCAACGATCTGTGA 1151
     ||||||||||||||||||||||||||
1148 CCGGGGCGGTCGTCAACGATCTGTGA 1173
```

*Fig. 5D*

| HSV-1 | | VZV | | EBV | |
|---|---|---|---|---|---|
| UL5 | (6133-3485) | 55 | (95996-98641) | BBLF4 | (114259-111830) |
| UL8 | (11478-9226) | 52 | (90493-92808) | BBRF1 | (114204-116045) |
| UL9 | (14261-11706) | 51 | (87881-90388) | BBRF2 | (116045-119137) |
| UL13 | (19504-17948) | 47 | (83168-84700) | BGLF4 | (123613-122325) |
| UL29 | (53053-49463) | 29 | (50857-54471) | BALF2 | (164770-161384) |
| UL30 | (53807-57514) | 28 | (50636-47052) | BALF5 | (156746-153701) |
| UL39 | (77444-80857) | 19 | (28845-26518) | BORF2 | (76407-78887) |
| UL40 | (80926-81948) | 18 | (26493-25573) | BaRF1 | (78900-79808) |
| UL42 | (84113-85579) | 16 | (23794-22568) | BMRF1 | (79899-81113) |
| UL52 | (100048-103224) | 6 | (8577-5326) | BSLF1 | (86879-84257) |

FIG.IIA
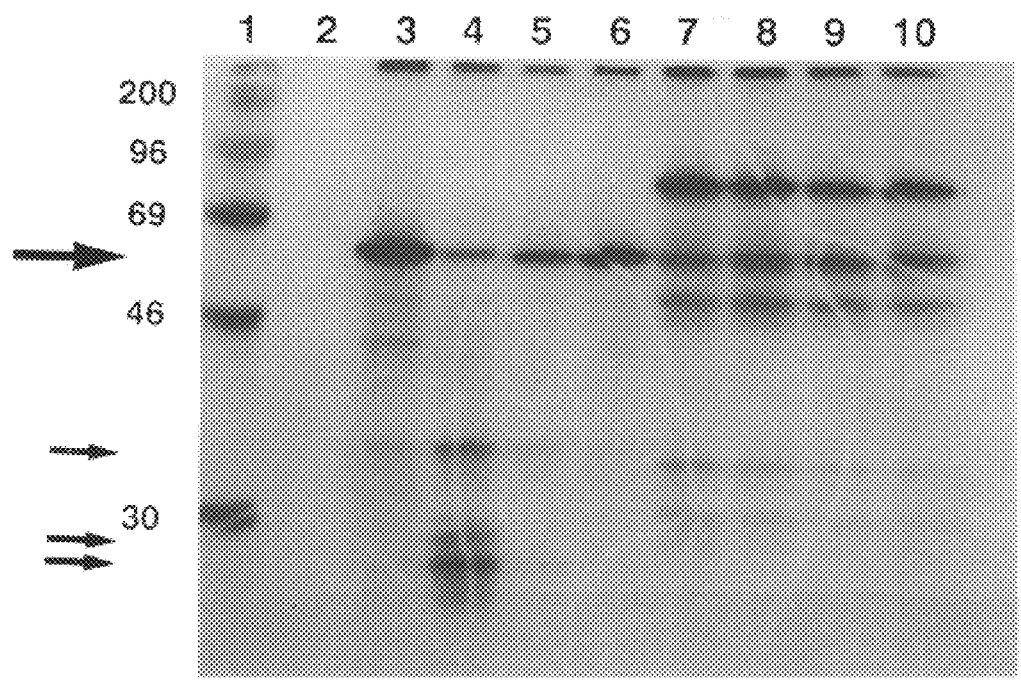
FIG.IIB
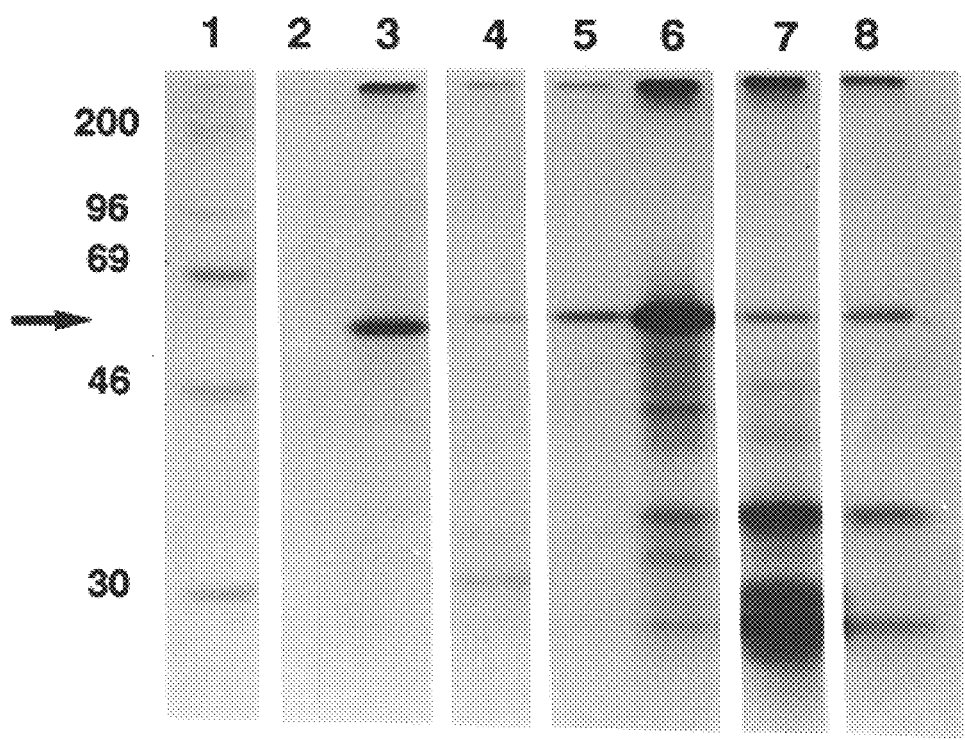

SEQUENCE LISTING

<160> NUMBER OF SEQ ID NOS: 16

<210> SEQ ID NO 1
<211> LENGTH: 18
<212> TYPE: DNA

```
<213> ORGANISM: Artificial Sequence
<220> FEATURE:
<223> OTHER INFORMATION: Description of Artificial Sequence:Synthetic

<400> SEQUENCE: 1
gtccgcgtcc atgtcggc                                                 18

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:Synthetic

<400> SEQUENCE: 2
ggactcatcc atccttcggc c                                             21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:Synthetic

<400> SEQUENCE: 3
gcggctggcc atttcaacag a                                             21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:Synthetic

<400> SEQUENCE: 4
cgcggaatcc atggcagcag g                                             21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:Synthetic

<400> SEQUENCE: 5
accgaggtcc atgtcgtacg c                                             21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence:Synthetic

<400> SEQUENCE: 6
ggactcatcc atccgtccgc c                                             21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:Synthetic

<400> SEQUENCE: 7
gccgaggtcc atgtcgtacg c                                             21
```

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:Synthetic

<400> SEQUENCE: 8
gcggttggcc attggaacca a                                        21

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence:Synthetic

<400> SEQUENCE: 9
gaggtccatg tcgta                                               15

<210> SEQ ID NO 10
<211> LENGTH: 12
<212> TYPE: DNA
<213> ORGANISM: Artificial Sequence
<220> FEATURE:
<223> OTHER INFORMATION: Description of Artificial Sequence:Synthetic

<400> SEQUENCE: 10
ttcctcctgc gg                                                  12

<210> SEQ ID NO 11
<211> LENGTH: 1557
<212> TYPE: DNA
<213> ORGANISM: human herpesvirus 1

<400> SEQUENCE: 11
atggatgagt cccgcagaca gcgacctgct ggtcatgtgg cagctaacct cagcccccaa      60
ggtgcacgcc aacggtcctt caaggattgg ctcgcatcct acgtacactc caacccccac    120
ggggcctccg ggcgcccag cggcccctct ctccaggacg ccgccgtctc ccgctcctcc     180
cacgggtccc gccaccgatc cggcctccgc gagcgccttc gcgcgggact atcccgatgg    240
cgaatgagcc gctcgtctca tgccgcgcg tccccgaga cgcccggtac ggcggccaaa      300
ctgaaccgcc cgcccctgcg cagatcccag gcggcgttaa ccgcacccc ctcgtccccc     360
tcgcacatcc tcaccctcac gcgcatccgc aagctatgca gccccgtgtt cgccatcaac    420
cccgccctac actacacgac cctcgagatc cccggggccc gaagcttcgg ggggtctggg    480
ggatacggtg acgtccaact gattcgcgaa cataagcttg ccgttaagac cataaaggaa    540
aaggagtggt tgccgttga gctcatcgcg accctgttgg tcggggagtg cgttctacgc    600
gccggccgca cccacaacat ccgcggcttc atcgcgcccc tcggttctc gctgcaacaa    660
cgacagatag tgttccccgc gtacgacatg gacctcggta agtatatcgg ccaactggcg    720
tccctgcgca acaaaaccc ctcggtctcg acggccctcc accagtgctt cacggagctg    780
gcccgcgccg ttgtgttttt aaacaccacc tgcgggatca gccacctgga tatcaagtgc    840
gccaacatcc tcgtcatgct gcggtcggac gccgtctcgc tccggcgggc cgtcctcgcc    900
gactttagcc tcgtcaccct caactccaac tccacgatcg gggggca gttttgcctc      960
caggagccgg acctcaagtc cccccggatg tttggcatgc ccaccgccct aaccacagcc   1020

-continued

| | |
|---|---|
| aactttcaca ccctggtggg tcacgggtat aaccagcccc cggagctgtt ggtgaaatac | 1080 |
| cttaacaacg aacgggccga atttaccaac caccgcctga agcacgacgt cgggttagcg | 1140 |
| gttgacctgt acgccctggg ccagacgctg ctggagttgg tggttagcgt gtacgtcgcc | 1200 |
| ccgagcctgg gcgtacccgt gacccggttt cccggttacc agtattttaa caaccagctg | 1260 |
| tcgccggact tcgccctggc cctgctcgcc tatcgctgcg tgctgcaccc agccctgttt | 1320 |
| gtcaactcgg ccgagaccaa cacccacggc ctggcgtatg acgtcccaga gggcatccgg | 1380 |
| cgccacctcc gcaatcccaa gattcggcgc gcgtttacgg atcggtgtat aaattaccag | 1440 |
| cacacacaca aggcgatact gtcgtcggtg gcgctgcctc ccgagcttaa gcctctcctg | 1500 |
| gtgctggtgt cccgcctgtg tcacaccaac ccgtgcgcgc ggcacgcgct gtcgtga | 1557 |

<210> SEQ ID NO 12
<211> LENGTH: 1557
<212> TYPE: DNA
<213> ORGANISM: human herpesvirus 2

<400> SEQUENCE: 12

| | |
|---|---|
| atggatgagt ccgggcgaca gcgacctgct ggtcgtgtgg cagctgacat cagcccccaa | 60 |
| ggtgcacacc gacgctcctt caaggcctgg ctcgcgtcct acatacactc cctcagccgc | 120 |
| cgggcgtccg gacgccaag cggcccctcc ccccgagacg cgccgtctc cggagcccgc | 180 |
| cccgggtccc gccgccgatc cagcttccgg gagcggcttc gcgcgggact gtcccgatgg | 240 |
| cgagtgagcc gctcgtctcg tcgccgctcg tcccccgagg ccccggccc tgcggccaag | 300 |
| ctaaggcgcc cgcccctgcg caggtccgag acggccatga cctcgccccc gtcgcccccc | 360 |
| tcgcacatcc tgtccctcgc gcgcatccac aagctatgca tccccgtatt cgccgtcaac | 420 |
| cccgccctcc gctacacgac ctcggagatc cccggggccc gcagcttcgg gggctcgggg | 480 |
| gggtacggcg aggtgcagtt gattcgcgaa cacaaactcg ccgtgaagac catccgggaa | 540 |
| aaagagtggt ttgccgtgga gctcgtcgcg accctgctcg tgggggagtg cgctcttcgc | 600 |
| ggcggccgca cccacgacat ccgcggcttt atcacccgc tcgggttctc gctgcagcag | 660 |
| cgccagatcg tgttccccgc gtacgacatg gacctcggca agtacatcgg ccagctggcg | 720 |
| tccctgcgcg cgaccacccc ctccgtcgcg acggccctcc accactgctt cacagacctg | 780 |
| gcgcgcgccg tggtgttcct gaacaccagg tgcgggatca gccacctgga catcaagtgc | 840 |
| gccaacgtcc tcgtgatgct gcgatcggac gcggtgtcgc tccggcgggc cgtcctggcc | 900 |
| gactttagcc tggtgacccct gaactccaac tccacgatat cccggggcca gttttgcctc | 960 |
| caggagccgg acctcgagtc cccccggggg tttgggatgc ccgccgccct gaccacggcc | 1020 |
| aactttcaca ctctggtggg gcacgggtac aaccagccac cggagctctc ggtaaagtac | 1080 |
| ctcaacaacg agcgggccga gtttaacaac cgccccctga agcacgacgt cgggctggcg | 1140 |
| gtcgatctct acgccctggg gcagacgctg ctggagctgc tggttagcgt gtacgtggcc | 1200 |
| ccgagcctgg gcgtccccgt gacccgcgtc ccgggctacc agtactttaa caaccagctc | 1260 |
| tcgccggact ttgccgtggc cctcctcgcc tatcgccgcg ttctgcaccc cgccctctt | 1320 |
| gtcaactcgg ccgagaccaa cacccacggc ctggcgtatg acgtgccgga gggcatccgg | 1380 |
| cgccaccttc gcaatcccaa gattcggcgc gcgttcacgg agcagtgtat aaattaccag | 1440 |
| cgcacgcaca aggcgtcct gtcgtcggtg tcgctgccgc ccgagctgag gccgctgctg | 1500 |
| gtgctggtct cccgcctctg tcacgccaac ccggccgcgc gccactctct gtcgtga | 1557 |

<210> SEQ ID NO 13
<211> LENGTH: 3651
<212> TYPE: DNA
<213> ORGANISM: human herpesvirus 1

<400> SEQUENCE: 13

| | | | | | |
|---|---|---|---|---|---|
| taccacaggt | gggtgctttg | gaaacttgtc | ggtcgccgtg | ctcctgtgag | cttgcgtccc | 60 |
| tccccggttt | cctttgcgct | cccgccttcc | ggacctgctc | tcgcctatct | tctttggctc | 120 |
| tcggtgcgat | tcgtcaggca | gcggccttgt | cgaatctcga | ccccaccact | cgccggactc | 180 |
| gccgacgtcc | cctctcgagc | ccgccgaaac | ccgccgaaac | ccgccgcgtc | tgttgaaatg | 240 |
| gccagccgcc | cagccgcatc | ctctcccgtc | gaagcgcggg | cccggttgg | gggacaggag | 300 |
| gccggcggcc | ccagcgcagc | cacccagggg | gaggccgccg | ggcccctct | cgcccacggc | 360 |
| caccacgtgt | actgccagcg | agtcaatggc | gtgatggtgc | tttccgacaa | gacgcccggg | 420 |
| tccgcgtcct | accgcatcag | cgatagcaac | tttgtccaat | gtggttccaa | ctgcaccatg | 480 |
| atcatcgacg | gagacgtggt | gcgcgggcgc | ccccaggacc | cgggggccgc | ggcatccccc | 540 |
| gctcccttcg | ttgcggtgac | aaacatcgga | gccggcagcg | acggcgggac | cgccgtcgtg | 600 |
| gcattcgggg | gaaccccacg | tcgctcggcg | gggacgtcta | ccggtaccca | gacggccgac | 660 |
| gtccccaccg | aggcccttgg | gggcccccct | cctcctcccc | gcttcaccct | gggtggcggc | 720 |
| tgttgttcct | gtcgcgacac | acggcgccgc | tctgcggtat | tcggggggga | gggggatcca | 780 |
| gtcggccccg | cggagttcgt | ctcggacgac | cggtcgtccg | attccgactc | ggatgactcg | 840 |
| gaggacacgg | actcggagac | gctgtcacac | gcctcctcgg | acgtgtccgg | cggggccacg | 900 |
| tacgacgacg | cccttgactc | cgattcgtca | tcggatgact | ccctgcagat | agatggcccc | 960 |
| gtgtgtcgcc | cgtggagcaa | tgacaccgcg | ccctggatg | tttgccccgg | gaccccggc | 1020 |
| ccgggcgccg | acgccggtgg | tccctcagcg | gtagacccac | acgcgccgac | gccagaggcc | 1080 |
| ggcgctggtc | ttgcggccga | tccgccgtg | gcccgggacg | acgcggaggg | gctttcggac | 1140 |
| ccccggccac | gtctgggaac | gggcacggcc | taccccgtcc | ccctggaact | cacgcccgag | 1200 |
| aacgcggagg | ccgtggcgcg | ctttctggga | gatgccgtga | accgcgaacc | cgcgctcatg | 1260 |
| ctggagtact | tttgccggtg | cgcccgcgag | gaaaccaagc | gtgtcccccc | caggacattc | 1320 |
| ggcagccccc | ctcgcctcac | ggaggacgac | tttgggcttc | tcaactacgc | gctcgtggag | 1380 |
| atgcagcgcc | tgtgtctgga | cgttcctccg | gtcccgccga | acgcatacat | gccctattat | 1440 |
| ctcagggagt | atgtgacgcg | gctggtcaac | gggttcaagc | cgctggtgag | ccggtccgct | 1500 |
| cgcctttacc | gcatcctggg | ggttctggtg | cacctgcgga | tccggacccg | ggaggcctcc | 1560 |
| tttgaggagt | ggctgcgatc | caaggaagtg | gccctggatt | ttggcctgac | ggaaaggctt | 1620 |
| cgcgagcacg | aagcccagct | ggtgatcctg | gcccaggctc | tggaccatta | cgactgtctg | 1680 |
| atccacagca | caccgcacac | gctggtcgag | cggggggctgc | aatcggccct | gaagtatgag | 1740 |
| gagttttacc | taaagcgttt | tggcgggcac | tacatggagt | ccgtcttcca | gatgtacacc | 1800 |
| cgcatcgccg | gcttttggcc | ctgccggggcc | acgcgcggca | tgcgccacat | cgccctgggg | 1860 |
| cgagagggt | cgtggtggga | aatgttcaag | ttcttttttcc | accgcctcta | cgaccaccag | 1920 |
| atcgtaccgt | cgacccccgc | catgctgaac | ctggggaccc | gcaactacta | cacctccagc | 1980 |
| tgctacctgg | taaacccccca | ggccaccaca | aacaaggcga | ccctgcgggc | catcaccagc | 2040 |
| aacgtcagtg | ccatcctcgc | ccgcaacggg | ggcatcgggc | tatgcgtgca | ggcgtttaac | 2100 |
| gactccggcc | ccgggaccgc | cagcgtcatg | cccgccctca | aggtccttga | ctcgctggtg | 2160 |

-continued

| | |
|---|---|
| gcggcgcaca acaaagagag cgcgcgtccg accggcgcgt gcgtgtacct ggagccgtgg | 2220 |
| cacaccgacg tgcgggccgt gctccggatg aaggggtcc tcgccggcga agaggcccag | 2280 |
| cgctgcgaca atatcttcag cgccctctgg atgccagacc tgtttttcaa cgcctgatt | 2340 |
| cgccacctgg acggcgagaa gaacgtcaca tggaccctgt cgaccggga caccagcatg | 2400 |
| tcgctcgccg actttcacgg ggaggagttc gagaagctct accagcacct cgaggtcatg | 2460 |
| gggttcggcg agcagatacc catccaggag ctggcctatg gcattgtgcg cagtgcggcc | 2520 |
| acgaccggga gccccttcgt catgttcaaa gacgcgtga accgccacta catctacgac | 2580 |
| acccaggggg cggccatcgc cggctccaac ctctgcaccg agatcgtcca tccggcctcc | 2640 |
| aagcgatcca gtgggtctg caacctggga agcgtgaatc tggcccgatg cgtctccagg | 2700 |
| cagacgtttg actttgggcg gctccgcgac gccgtgcagg cgtgcgtgct gatggtgaac | 2760 |
| atcatgatcg acagcacgct acaacccacg ccccagtgca cccgcggcaa cgacaacctg | 2820 |
| cggtccatgg gaatcggcat gcagggcctg cacacggcct gcctgaagct ggggctggat | 2880 |
| ctggagtctg ccgaatttca ggacctgaac aaacacatcg ccgaggtgat gctgctgtcg | 2940 |
| gcgatgaaga ccagcaacgc gctgtgcgtt cgcggggccc gtcccttcaa ccactttaag | 3000 |
| cgcagcatgt atcgcgccgg ccgctttcac tgggagcgct ttccggacgc ccggccgcgg | 3060 |
| tacgagggcg agtgggagat gctacgccag agcatgatga acacggcct gcgcaacagc | 3120 |
| cagtttgtcg cgctgatgcc caccgccgcc tcggcgcaga tctcggacgt cagcgagggc | 3180 |
| tttgcccccc tgttcaccaa cctgttcagc aaggtgaccc gggacggcga gacgctgcgc | 3240 |
| cccaacacgc tcctgctaaa ggaactggaa cgcacgttta gcgggaagcg cctcctggag | 3300 |
| gtgatggaca gtcgacgc aagcagtgg tccgtgccgc aggcgctccc gtgcctggag | 3360 |
| cccacccacc ccctccggcg attcaagacc gcgtttgact acgaccagaa gttgctgatc | 3420 |
| gacctgtgtg cggaccgcgc cccctacgtc gaccatagcc aatccatgac cctgtatgtc | 3480 |
| acggagaagg cggacgggac cctcccagcc tccaccctgg tccgccttct ggtccacgca | 3540 |
| tataagcgcg gactaaaaac aggatgtac tactgcaagg ttcgcaaggc gaccaacagc | 3600 |
| ggggtctttg cggcgacga caacattgtc tgcatgagct gcgcgctgtg a | 3651 |

<210> SEQ ID NO 14
<211> LENGTH: 3678
<212> TYPE: DNA
<213> ORGANISM: human herpesvirus 2

<400> SEQUENCE: 14

| | |
|---|---|
| accacaacag gtgggtgctt cggggacttg acggtcgcca ctctcctgcg agccctcacg | 60 |
| tcttcgccca ccgattcctg ttgcgttcct gtcggccggt gctgtcctgt cgacagattg | 120 |
| ttggcgactg cccgggtgat tcgtcggccg gtgcgtcctt tcgctcgtac cgcccacccc | 180 |
| gcctccacg ggcccgccgc tgtttccgtt catcgcgtcc gagccaccgt caccttggtt | 240 |
| ccaatggcca accgccctgc cgcatccgcc ctcgccggag cgcggtctcc gtccgaacga | 300 |
| caggaacccc gggagcccga gtcgcccccc cctggcggcg accacgtgtt ttgcaggaaa | 360 |
| gtcagcggcg tgatggtgct ttccagcgat ccccccggcc ccgcggccta ccgcattagc | 420 |
| gacagcagct ttgttcaatg cggctccaac tgcagtatga taatcgacgg agacgtggcg | 480 |
| cgcggtcatt tgcgtgacct cgagggcgct acgtccaccg cgccttcgt cgcgatctca | 540 |
| aacgtcgcag ccggcgggga tggccgaacc gccgtcgtgg cgctcggcgg aacctcgggc | 600 |
| ccgtccgcga ctacatccgt ggggacccag acgtccgggg agttcctcca cgggaaccca | 660 |

```
aggaccccg  aaccccaagg  accccaggct  gtcccccgc   cccctcctcc  cccctttcca   720
tggggccacg  agtgctgcgc  ccgtcgcgat  gccaggggcg  gcgccgagaa  ggacgtcggg   780
gccgcggagt  catggtcaga  cggcccgtcg  tccgactccg  aaacgagga   ctcggactcc   840 tcggacgagg  atacgggctc  gggttcggag  acgctgtctc  gatcctcttc  gatctgggcc   900 gcagggcga   ctgacgacga  tgacagcgac  tccgactcgc  ggtcggacga  ctccgtgcag   960
cccgacgttg  tcgttcgtcg  cagatggagc  gacggccctg  cccccgtggc  ctttcccaag  1020
ccccggcgcc  ccgcgactc   ccccggaaac  cccgcctgg   gcgccggcac  cgggccgggc  1080
tccgcgacgg  acccgcgcgc  gtcggccgac  tccgattccg  cggcccacgc  cgccgcaccc  1140
caggcggacg  tggcgccggt  tctggacagc  cagcccactg  tgggaacgga  ccccggctac  1200
ccagtccccc  tagaactcac  gcccgagaac  gcggaggcgg  tggcgcggtt  tctgggggac  1260
gccgtcgacc  gcgagcccgc  gctcatgctg  gagtacttct  gtcggtgcgc  ccgcgaggag  1320
agcaagcgcg  tgcccccacg  aaccttcggc  agcgccccc   gcctcacgga  ggacgacttt  1380
gggctcctga  actacgcgct  cgctgagatg  cgacgcctgt  gcctgaccct  tccccggtc   1440 cccccaacg   catacacgcc  ctatcatctg  agggagtatg  cgacgcggct  ggttaacggg  1500
ttcaaacccc  tggtgcggcg  gtccgcccgc  ctgtatcgca  tcctggggat  tctggttcac  1560
ctgcgcatcc  gtacccggga  ggcctccttt  gaggaatgga  tgcgctccaa  ggaggtggac  1620
ctggacttcg  ggctgacgga  aaggcttcgc  gaacacgagg  cccagctaat  gatcctggcc  1680
caggccctga  acccctacga  ctgtctgatc  cacagcaccc  cgaacacgct  cgtcgagcgg  1740
gggctgcagt  cggcgctgaa  gtacgaagag  ttttacctca  agcgcttcgg  cgggcactac  1800
atggagtccg  tcttccagat  gtacacccgc  atcgccgggt  tcctggcgtg  ccgggcgacc  1860
cgcggcatgc  gccacatcgc  cctggggcga  caggggtcgt  ggtgggaaat  gttcaagttc  1920 ttttccacc   gcctctacga  ccaccagatc  gtgccgtcca  ccccgccat   gctgaacctc  1980 ggaacccgca  actactacac  gtccagctgc  tacctggtaa  accccaggc   caccactaac  2040 caggccaccc  tccgggccat  caccggcaac  gtgagcgcca  tcctcgcccg  caacggggc   2100 atcgggctgt  gcatgcaggc  gttcaacgac  gccagcccg   gcaccgccag  catcatgccg  2160
gccctgaagg  tcctggactc  cctggtggcg  gcgcacaaca  aacagagcac  gcgcccacc   2220 ggggcgtgcg  tgtacctgga  accctggcac  agcgacgttc  gggccgtgct  cagaatgaag  2280
ggcgtcctcg  ccggcgagga  ggcccagcgc  tgcgacaaca  tcttcagcgc  cctctggatg  2340
ccggacctgt  tcttcaagcg  cctgatccgc  cacctcgacg  gcgagaaaaa  cgtcacctgg  2400
tccctgttcg  accgggacac  cagcatgtcg  ctcgccgact  tcacggcga   ggagttcgag  2460 aagctgtacg  agcacctcga  ggccatgggg  ttcggcgaaa  cgatccccat  ccaggacctg  2520
gcgtacgcca  tcgtgcgcag  cgcggccacc  accggaagcc  ccttcatcat  gtttaaggac  2580
gcggtaaacc  gccactacat  ctacgacacg  caaggggcgg  ccattgccgg  ctccaacctc  2640
tgcacggaga  tcgtccaccc  gtcctccaaa  cgctccagcg  ggtctgcaa   cctgggcagc  2700 gtgaatctgg  cccgatgcgt  ctcccggcgg  acgttcgatt  ttggcatgct  ccgcgacgcc  2760
gtgcaggcgt  gcgtgctaat  ggttaatatc  atgatagaca  gcacgctgca  gccgacgccc  2820
cagtgcgccc  gcggccacga  caacctgcgg  tccatgggca  ttggcatgca  gggcctgcac  2880
acggcgtgcc  tgaagatggg  cctggatctg  gagtcggccg  agttccggga  cctgaacaca  2940
cacatcgccg  aggtgatgct  gctcgcggcc  atgaagacca  gtaacgcgct  gtgcgttcgc  3000
```

-continued

| | |
|---|---|
| ggggcgcgtc ccttcagcca ctttaagcgc agcatgtacc gggccggccg ctttcactgg | 3060 |
| gagcgctttt cgaacgccag cccgcggtac gagggcgagt gggagatgct acgccagagc | 3120 |
| atgatgaaac acggcctgcg caacagccag ttcatcgcgc tcatgcccac cgccgcctcg | 3180 |
| gcccagatct cggacgtcag cgagggcttt gccccctgt tcaccaacct gttcagcaag | 3240 |
| gtgaccaggg acgcgagac gctgcgcccc aacacgctct tgctgaagga actcgagcgc | 3300 |
| acgttcggcg ggaagcggct cctggacgcg atggacgggc tcgaggccaa gcagtggtct | 3360 |
| gtggcccagg ccctgccttg cctggacccc gccacccccc tccggcggtt caagacggcc | 3420 |
| ttcgactacg accaggaact gctgatcgac ctgtgtgcag accgcgcccc ctatgttgat | 3480 |
| cacagccaat ccatgactct gtatgtcaca gagaaggcgg acgggacgct ccccgcctcc | 3540 |
| accctggtcc gccttctcgt ccacgcatat aagcgcggcc tgaagacggg gatgtactac | 3600 |
| tgcaaggttc gcaaggcgac caacagcggg gtgttcgccg gcgacgacaa catcgtctgc | 3660 |
| acaagctgcg cgctgtaa | 3678 |

<210> SEQ ID NO 15
<211> LENGTH: 1151
<212> TYPE: DNA
<213> ORGANISM: human herpesvirus 1

<400> SEQUENCE: 15

| | |
|---|---|
| gtactactgc aaggttcgca aggcgaccaa cagcggggtg ttcgccggcg acgacaacat | 60 |
| cgtctgcaca agctgcgcgc tgtaagcaac agcgctccga tcgggtcag gcgtcgctct | 120 |
| cggtcccgca tatcgccatg gatcccgccg tctcccccgc gagcaccgac cccctagata | 180 |
| cccacgcgtc gggggccggg gcggccccga ttccggtgtg ccccaccccc gagcggtact | 240 |
| tctacacctc ccagtgcccc gacatcaacc accttcgctc cctcagcatc ctgaaccgct | 300 |
| ggctggagac cgagctcgtg ttcgtggggg acgaggagga cgtctccaag ctctccgagg | 360 |
| gcgagctcgg cttctaccgc tttctgtttg ccttcctgtc ggccgcggac gacctggtga | 420 |
| cggaaaacct gggcggcctc tccggcctct tcgaacagaa ggacattctt cactactacg | 480 |
| tggagcagga atgcatcgag gtcgtccact cgcgcgtcta acatcatc cagctggtgc | 540 |
| tctttcacaa caacgaccag gcgcgccgcg cctatgtggc ccgcaccatc aaccaccgg | 600 |
| ccattcgcgt caaggtggac tggctggagg cgcgggtgcg ggaatgcgac tcgatcccgg | 660 |
| agaagttcat cctcatgatc ctcatcgagg gcgtcttttt tgccgcctcg ttcgccgcca | 720 |
| tcgcgtacct gcgcaccaac aacctcctgc gggtcacctg ccagtcgaac gacctcatca | 780 |
| gccgcgacga ggccgtgcat acgacagcct cgtgctacat ctacaacaac tacctcgggg | 840 |
| gccacgccaa gcccgaggcg gcgcgcgtgt accggctgtt tcgggaggcg gtggatatcg | 900 |
| agatcgggtt catccgatcc caggcccga cggacagctc tatcctgagt ccgggggccc | 960 |
| tggcggccat cgagaactac gtgcgattca gcgcggatcg cctgctgggc ctgatccata | 1020 |
| tgcagccccct gtattccgcc cccgccccg acgccagctt tccccctcagc ctcatgtcca | 1080 |
| ccgacaaaca caccaacttc ttcgagtgcc gcagcaccto gtacgccggg gccgtcgtca | 1140 |
| acgatctgtg a | 1151 |

<210> SEQ ID NO 16
<211> LENGTH: 1173
<212> TYPE: DNA
<213> ORGANISM: human herpesvirus 2

<400> SEQUENCE: 16

-continued

```
actactgcaa ggttcgcaag gcgaccaaca gcggggtctt tggcggcgac gacaacattg      60
tctgcacggc tgcgcgctgt gaccgacaaa ccccctccgc gccaggcccg ccgccactgt     120
cgtcgccgtc ccacgcgctc ccccgctgcc atggattccg cggccccagc cctctccccc     180
gctctgacgg cccatacggg ccatagcgcg acggcggacc tagcgatcca gattccaaag     240
tgccccgacc ccgagaggta cttctacacc tcccagtgtc ccgacattaa ccacctgcgc     300
tccctcagca tccttaaccg ctggctggaa accgagcttg ttttcgtggg ggacgaggag     360
gacgtctcca agctttccga gggcgagctc agcttttacc gcttcctctt cgctttcctg     420
tcggccgccg acgacctggt tacggaaaac ctgggcggcc tctccggcct gtttgagcag     480
aaggacattc tccactacta cgtggagcag gaatgcatcg aagtcgcaca ctcgcgcgtg     540
tacaacatca tccagctggt gcttttccac aacaacgacc aggcgcgccg cgagtacgtg     600
gccggcacca tcaaccaccc ggccatccgc gccaaggtgg actggctgga agcgcgggtg     660
cgggaatgcg cctccgttcc ggaaaagttc attctcatga tcctcatcga gggcatcttt     720
tttgccgcct cgtttgccgc catcgcctac cttcgcacca acaaccttct gcgggtcacc     780
tgccagtcaa acgacctcat cagccgggac gaggccgtgc acacgacggc ctcgtgttac     840
atctacaaca actacctggg cgggcacgcc aagcccccgc ccgaccgcgt gtacgggctg     900
ttccgccagg cggtcgagat cgagatcgga tttatccgat cccaggcgcc gacggacagc     960
catatcctga gcccggcggc gctggcggcc atcgaaaact acgtgcgatt cagcgcggat    1020
cgcctgttgg gccttatcca catgaagcca ctgttttccg ccccaccccc cgacgccagc    1080
tttccgctga gcctcatgtc caccgacaaa cacaccaatt ttttcgagtg tcgcagcacc    1140
tcctacgccg gggcggtcgt caacgatctg tga                                 1173
```

OLIGONUCLEOTIDE THERAPIES FOR MODULATING THE EFFECTS OF HERPESVIRUSES

This application is a continuation-in-part of U.S. Ser. No. 07/485,297, filed Feb. 26, 1990, now U.S. Pat. No. 5,248,670.

FIELD OF THE INVENTION

This invention relates to therapies and diagnostics for herpesvirus infections. In particular, this invention relates to antisense oligonucleotide interactions with certain portions of herpesvirus RNA which have been found to lead to modulation of the activity of the RNA and, thus, to modulation of the effects of the viruses themseves.

BACKGROUND OF THE INVENTIONS

Approximately 500,000 new cases of genital herpes are reported each year, and it is estimated that 30 million Americans are affected by this currently incurable disease. Similarly, it is estimated that there is an annual incidence of 500,000 new cases of herpes simplex gingivostomatitis and at least 100 million Americans suffer from recurrent herpes labialis. Overall the prevalence of seropositive individuals in the general population is approximately 70–80%. Although recurrent herpes simplex virus infections are the most prevalent of all herpesvirus infections, there is a need to develop more specific forms of therapy for diseases such as herpes simplex encephalitis, keratoconjunctivitis, herpetic whitlow and disseminated herpes infections of neonates and immunocompromised hosts.

The incidence of encephalitis is low (one case in 250,000 individuals per year), yet with existing therapy, the mortality rate is as high as 40% and approximately 50% of the survivors are left with severe neurological sequelae. Ocular infections are neither rare nor trivial. They are usually caused by HSV-1 and are a leading cause of blindness in many countries of the world. Herpetic whitlow is an occupational hazard of nurses, dentists and physicians which begins with erythema and tenderness of the distal segments of the fingers and is followed by coalescence and enlargement of the vesicles. An accompanying lymphangitis and lymphadenopathy of the draining lymphatics is a common feature. Neonatal HSV infection is usually encountered as a consequence of a child being born through an infected birth canal. The incidence of the disease is approximately 1 in 10,000 births. Mortality in babies with limited infection can be as high as 20% while mortality of neonates from disseminated infection, even with current therapy, can approach 75% and many survivors have significant neurological impairment.

Currently, nucleoside analogs are clearly the preferred therapeutic agents for HSV infections. A number of pyrimidine deoxyribonucleoside compounds have a specific affinity for the virus-encoded thymidine (dCyd) kinase enzyme. The specificity of action of these compounds confines the phosphorylation and antiviral activity of these compounds to virus-infected cells. A number of drugs from this class, e.g., 5-iodo-dUrd (IDU), 5-trifluoromethyl-dUrd (FMAU), 5-ethyl-dUrd (EDU), (E)-5-(2-bromovinyl)-dUrd (BVDU), 5-iodo-dCyd (IDC), and 5-trifluoromethyl-dUrd (TFT), are either in clinical use or likely to become available for clinical use in the near future. IDU is a moderately effective topical antiviral agent when applied to HSV gingivostomatitis and ocular stromal keratitis, however, its use in controlled clinical studies of HSV encephalitis revealed a high toxicity associated with IDU treatment. Although the antiviral specificity of 5-arabinofuranosyl cytosine (Ara-C) was initially promising, its clinical history has paralleled that of IDU. The clinical appearance of HSV strains which are deficient in their ability to synthesize the viral thymidine kinase has generated further concern over the future efficacy of this class of compounds.

The utility of a number of viral targets has been defined for anti-HSV compound development. Studies with thiosemicarbazone compounds have demonstrated that inhibition of the viral ribonucleotide reductase enzyme is an effective means of inhibiting replication of HSV In vitro. Further, a number of purine nucleosides which interfere with viral DNA replication have been approved for treatment of human HSV infections. 9-(β-D-arabinofuranosyl) adenine (Ara-A) has been used for treatment of HSV-1 keratitis, HSV-1 encephalitis and neonatal herpes infections. Reports of clinical efficacy are contradictory and a major disadvantage for practical use is the extremely poor solubility of Ara-A in water. 9-(2-hydroxyethoxymethyl) guanine (Acyclovir, ACV) is of major interest. In humans, ACV has been used successfully in the therapy of localized and disseminated HSV infections. However, there appear to be both the existence of drug-resistant viral mutants and negative results in double-blind studies of HSV-1 treatment with ACV. ACV, like Ara-A, is poorly soluble in water (0.2%) and this physical characteristic limits the application forms for ACV. The practical application of purine nucleoside analogs in an extended clinical situation suffers from their inherently efficient catabolism, which not only lovers the biological activity of the drug but also nay result in the formation of toxic catabolites.

All of the effective anti-HSV compounds currently in use or clinical testing are nucleoside analogs. The efficacy of these compounds is diminished by their inherently poor solubility in aqueous solutions, rapid intracellular catabolism and high cellular toxicities. An additional caveat to the long-term use of any given nucleoside analog is the recent detection of clinical isolates of HSV which are resistant to inhibition by nucleoside compounds which were being administered in clinical trials. Antiviral oligonucleotides offer the potential of better compound solubilities, lower cellular toxicities and less sensitivity to nucleotide point mutations in the target gene than those typical of the nucleoside analogs.

It is apparent that new routes to the diagnosis and therapy of herpesvirus infections are greatly desired. It is particularly desired to provide compositions and methods for therapy which are, at once, highly effective and possessed of no or only minor side effects. Thus, the provision of antisense oligonucleotide therapies for herpesvirus infections in accordance with this invention satisfies the long-felt need for such therapies.

OBJECTS OF THE INVENTION

It is a principal object of the invention to provide therapies for herpesvirus and related infections.

It is a further object of the invention to provide antisense oligonucleotides which are capable of inhibiting the function of RNA of herpesviruses and related viruses.

Yet another object is to secure means for diagnosis of herpesvirus infection.

These and other objects of this invention will become apparent from a review of the instant specification.

SUMMARY OF THE INVENTION

In accordance with the present invention, oligonucleotides and oligonucleotide analogs are provided which are specifically hybridizable with RNA or DNA deriving from a gene corresponding to one of the open reading frames UL5, UL8, UL9, UL13, UL29, UL30, UL39, UL40, UL42 AND UL52 of herpes simplex virus type 1. The oligonucleotide comprises nucleotide units sufficient in identity and number to effect such specific hybridization. It is preferred that the oligonucleotides or oligonucleotide analogs be specifically hybridizable with a translation initiation site and preferably that the oligonucleotide comprise a sequence CAT.

In accordance with preferred embodiments, the oligonucleotides and oligonucleotide analogs are designed to be specifically hybridizable with DNA or even more preferably, RNA from one of the species herpes simplex virus type 1 (HSV-1), herpes simplex virus type 2 (HSV-2), cytomegalovirus, human herpes virus 6, Epstein Barr virus (EBV) or varicella zoster virus (VZV). Such oligonucleotides and analogs are conveniently and desirably presented in a pharmaceutically acceptable carrier.

In accordance with other preferred embodiments, the oligonucleotides and oligonucleotide analogs are formulated such that at least some of the linking groups between nucleotide units of the oligonucleotide units comprise sulfur-containing species such as phosphorothioate moieties.

Other aspects of the invention are directed to methods for diagnostics and therapeutics of animals, especially humans, suspected of having a herpesvirus infection. Such methods comprise contacting either the animal or a body fluid of the animal with oligonucleotides or oligonucleotide analogs in accordance with the invention in order to inhibit the proliferation or effect of such infection, or to effect a diagnosis thereof Persons of ordinary skill in the art will recognize that the particular open reading frames described for herpes simplex virus type 1 find counterparts in the other viruses named. Thus each of herpes simplex virus type 2, cytomegalovirus, human herpes virus type 6, Epstein Barr virus and varicella zoster virus are believed to have many analogous open reading frames which code for proteins having similar functions. Accordingly, the present invention is directed to antisense oligonucleotide therapy where the oligonucleotides or oligonucleotide analogs are directed to any of the foregoing viruses, or indeed to any similar viruses which may become known hereafter, which have one or more of such analogous open reading frames. For convenience in connection with the present invention, all such viruses are denominated as herpesviruses.

BRIEF DESCRIPTION OF THE DRAWINGS

FIG. 3 depicts a comparison of the UL13 translational open reading frames (ORFs) of the HSV-1(SEQ ID NO: 11), strain 17 and HSV-2(SEQ ID NO: 12), strain HG52 mRNA species.

FIG. 4 is a sequence comparison of the UL39 gene DNAs for HSV-1(SEQ ID NO: 13), strain 17 and HSV-2(SEQ ID NO: 14), strain 333 with the translation initiation codon highlighted at 238 of HSV-1.

FIG. 5 is a sequence comparison of the UL40 gene DNAs for HSV-1(SEQ ID NO: 15), KOS strain and HSV-2(SEQ ID NO: 16), strain 333 with the translation initiation codon highlighted at 138 of HSV-1.

FIG. 6 is tabulation of the homologous ORFS among HSV-1, VZV, and EBV as predicted from published DNA sequence data.

FIGS. 11A–11B are photographs showing the effect of various oligonucleotides upon the in vitro translation of RNA. Numbers to the left of the gels indicate the relative molecular mass of marker proteins shown in Lane 1. The bold arrow points to the major polypeptide product synthesized from HSV RNAs. Lesser arrows point to the polypeptides synthesized from HSV RNA in the presence of inhibitory oligonucleotide. For translational inhibition, the molar ratio of oligonucleotide:RNA was 50:1. (A.) Specificity of oligonucleotide inhibitory effect. Lanes 2–10 contain In vitro translation products from reticulocyte lysates using the following: lane 2, no RNA; lanes 3–6, pIP-1 RNA (0.112 pmoles); lanes 7–10, 5LO RNA (0.145 pmoles). Lanes 4 and 8, ISIS 1049; lanes 5 and 9, ISIS 1082; lanes 6 and 10, ISIS 1238. (B.) Spectrum of inhibitory activity. Lanes 2–8 contain in vitro translation products from reticulocyte lysates using the following: lane 2, no RNA; lanes 3–5, pIP-2 RNA (0.108 pmoles); lanes 6–8, pIP-1 RNA (0.112 pmoles); lanes 4 and 7, ISIS 1049; lanes 5 and 8, ISIS 1082.

DETAILED DESCRIPTION OF THE INVENTION

Figure 1:
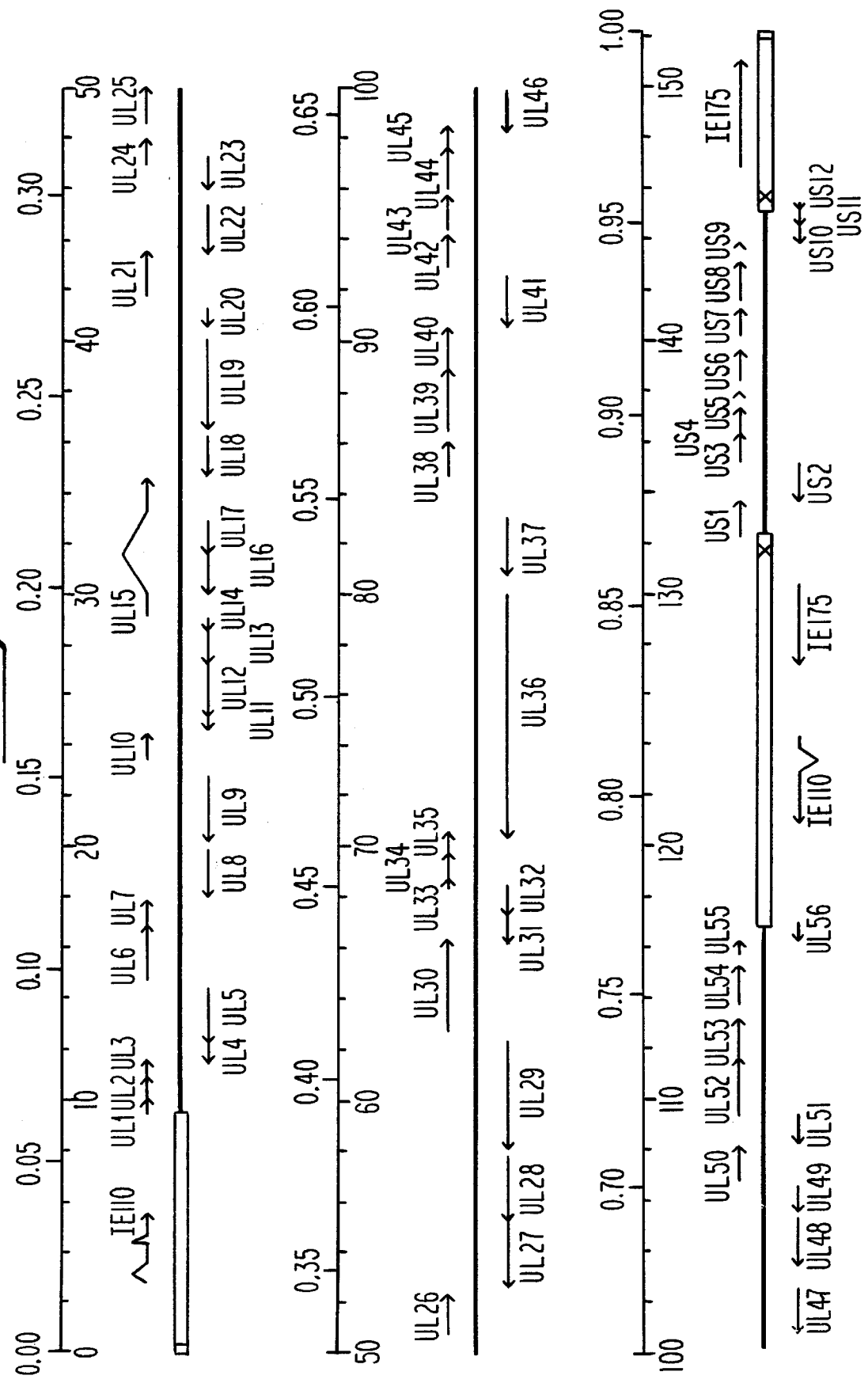
FIG. 1 is a depiction of the arrangement of the genes of herpes simplex virus type 1 in accordance with the data of McGeoch, D. J. et. al.; J. Gen. Virol., 69, 1531–1574 (1988).

Herpes simplex virus is the most studied of the human herpes viruses. The virus exists in two similar but distinct subtypes (HSV-1 and HSV-2); numerous strains of each subtype are known. Although the host range of some HSV strains is limited to certain tissues in vivo, the in vitro host range of all strains includes most human tissue types (both primary and transformed cells) as well as many non-human cells. The viral replication cycle is rapid, requiring approximately 24 hours for HSV-1 and 48 hours for HSV-2 to produce infectious progeny. The rapid replication and broad host range of HSV has resulted in an extensive molecular analysis of viral gene structure and of the control of viral gene expression during infection.

The productive infection of HSV consists of a number of differentiable stages which include: adsorption of the virus to the host cell membrane, fusion of the viral envelope with the cellular membrane, penetration of the non-enveloped virion to the nucleus of the cell, uncoating of viral nucleic acid, expression of viral genes and replication of the viral genome, nuclear packaging of the genome into newly formed viral capsids and finally, egress of the mature virion from the cell. Virally encoded proteins have been identified which control, in part, each of these stages of viral replication. The DNA sequence of the HSV-1 genome has been published and supports prior estimates that at least 71 unique viral proteins are encoded by the virus during a productive infection. McGeoch, D. J., Dolan, A., Donald, S., and Rixon, F. J. *J. Mol. Biol.* 181; 1–13 (1985); McGeoch, D. J., Dolan, A., Donald, S., and Brauer, D. H. K.; *Nucleic Acids Res.* 14: 1727–1745 (1986); McGeoch, D. J., Dalrymple, M. A., Davison, A. J., Dolan, A., Frame, M. C., McNab, D., Perry, L. J., Scott, J. E., and Taylor, P.; *J. Gen. Virol.* 69: 1531–1574 (1988); and Perry, L. J. and McGeoch, D. J.; *J. Gen. Virol.* 69: 2831–2846 (1988).

The structure of HSV genes is quite simple. The transcription of each mRNA is controlled by a promoter region located immediately 5' to the RNA cap site for that gene. Splicing of mRNAs is rare and restricted primarily to the immediate early class of transcripts. A unique mRNA species exists for each putative protein product encoded by the virus and each of the viral mRNAs are considered to act like a monocistronic species even though multiple open reading frames (ORFS) are present in many of the RNAs. The control of viral gene expression is a finely orchestrated cascade which can be divided into three general stages: the immediate early, early and late phases. The immediate early transcripts are synthesized at the onset of viral replication, even in the presence of translational inhibitors such as cycloheximide. Thus, the synthesis of this class of transcripts is controlled by existing cellular proteins and/or proteins brought into the cell by the infecting virion. The immediate early proteins are known to influence cellular and viral gene expression in both positive and negative manners, and the expression of these proteins is important for the transcriptional activation of other HSV genes, especially the early genes. The early gene transcripts encode many of the viral products which are necessary for replication of the viral genome. Because the synthesis of late gene transcripts is controlled by both the immediate early proteins and template abundance, the late genes are transcribed maximally only after viral DNA synthesis. The proteins encoded by the late genes include the envelope glycoproteins, the capsid proteins and other proteins which are necessary to maintain viral structure or permit egress of newly formed virions from the cell.

DNA sequence analysis predicts a conservative estimate of 71 proteins encoded within the HSV-1 genome. FIG. 1 sets forth nomenclature of HSV-1 genes and genomic organization of the unique long (UL) and unique short (US) regions. Although a number of viral gene products have been shown to be dispensable to viral replication in vitro, only the viral thymidine kinase function has been known to be dispensable for viral growth in the human host. Logically, this leaves 70 gene targets which could be amenable to target-directed antiviral chemotherapy. During viral replication, the viral mRNAs represent the most diverse and versatile targets for antisense oligonucleotide inhibition.

Because the transcription of HSV mRNAs is tightly regulated within the cascade pattern of gene expression, the relative concentration of an HSV mRNA depends upon the time of sampling during the course of infection. Generally, maximal levels of mRNA concentration are reached at a time 3–4 hours after the onset of its synthesis. The rates of mRNA decay are not known for all of the HSV mRNAs; rates vary among the examples cited in the literature. A number of structural features of HSV mRNAs are important to the efficient translation of viral proteins. The 5' caps, consensus translation initiation codons and the 3' polyadenylated tails of HSV mRNAs are presumed to function in a manner analogous to similar mRNA structures which have been described for many cellular mRNAs. Splicing of HSV mRNAs is rare, but the splice sites of the immediate early transcripts represent another structural feature of the viral transcripts which could be considered as a feasible site of antisense inhibition. Additionally, unique structural features of the HSV UL48 mRNA have been reported to influence the rate of tegument protein synthesis. See Blair, E. D., Blair, C. C., and Wagner, E. K.; *J. Virol.* 61: 2499–2508 (1987). The presence of similar structures in other HSV mRNAs or the ability of these structures to influence synthesis of their cognate protein species has not been examined. Thus, a large number of potential structural regions of an HSV mRNA can be targeted as a putative site for antisense oligonucleotide inhibition of mRNA function. Indeed, the treatment of infected cells with oligonucleotides which are complementary to the splice sites of the US1 and US2 genes or the translation initiation region of the UL48 gene has resulted in the inhibition of HSV replication in vitro. See Smith, C. C., Aurelian, L., Reddy, M. P., Miller, P. S., and Ts'o, P. O. P.; *Proc. Natl. Acad. Sci. USA* 83: 2787–2792 (1986); and Ceruzzi, M, and Draper, K.; *Nucleosides and Nucleotides* 8: 815–818 (1989).

Viral gene products which are known to contribute a biological function to HSV replication can be categorized into three groups. These are 1. transcriptional activator or repressor proteins, 2. DNA replication proteins and 3. structural proteins. The immediate early class of HSV transcripts encode proteins which function as transcriptional activators and repressors of other viral genes. Strains of virus which are deficient in the production of these proteins have been reported and with the exception of the IE175 gene product, the immediate early proteins do not appear to be essential to viral replication. The transacting functions of other immediate early proteins can be substituted by either IE175 or host functions. The transcription of IE175 mRNA continues in the infected cell until levels of IE175 protein reach concentrations which inhibit the further transcription of IE175 mRNA. Thus, the inhibition of IE175 protein synthesis by an appropriate antisense oligonucleotide would result in steadily increasing levels of the IE175 mRNA, which could eventually exceed the molar threshold of concentration that represents the limit for effective oligonucleotide inhibition. An additional problem of antisense therapy designed for immediate early genes is that the temporal expression of the immediate early genes could necessitate a prophylactic administration of oligonucleotide for efficacy.

Although this type of dosage is possible, it is not feasible in lost human infections.

The most studied group of viral proteins are those involved in genomic replication. At least seven viral proteins (UL5, 8, 9, 29, 30, 42 and 52) are directly involved in viral DNA replication. The viral DNA polymerase, the thymidine kinase and the ribonucleotide reductase enzyme functions have been inhibited successfully with nucleoside analogs and work continues to find more potent versions of these compounds. The development of drug-resistant strains of HSV limit the feasibility of developing a nucleoside analog with long-term efficacy in clinical use. Because the transcription of some late viral genes depends upon gene dosage for efficient expression, antisense inhibition of viral structural protein synthesis could also be accomplished indirectly by targeting the DNA synthetic proteins.

The use of structural proteins in antiviral efforts has centered on the development of vaccines and represents an unexplored field for chemotherapeutic intervention with antisense compounds. Proteins classed into this group include those known to play roles in viral assembly and structural integrity, viral adsorption, virion fusion with the host cell membrane and virus penetration into the infected cell.

Recently it has been reported that some viral proteins may serve bifunctional roles in HSV replication. In accordance with the present invention, these are now believed to offer the opportunity to directly affect multiple levels of viral replication by inhibiting a single protein product. The members of this class of viral proteins (UL13 and UL39) are limited in number, but represent targets which are believed to be very promising candidates for antisense inhibition. The viral proteins identified as the UL13 and UL39 ORFs of HSV-1 exhibit a high degree of nucleotide sequence conservation among homologues of various HSV-1 and HSV-2 subtypes. The UL13 and UL39 genes have now been determined to be the best sites for targeting therapeutic attack. A third protein, UL40, which forms the active ribonucleotide reductase enzyme complex with the UL39 protein, is also now believed to be a promising target for antisense inhibition.

Additional proteins are also believed to be good targets for antisense oligonucleotide therapeutic attack. These include proteins from the open reading frames UL5, UL8, UL9, UL29, UL30, UL42 And UL52. Accordingly, the present invention is preferably directed to inhibition of the function of mRNAs deriving from a gene corresponding to one of the open reading frames UL5, UL8, UL9, UL13, UL29, UL30, UL39, UL40, UL42 AND UL52 of herpes simplex virus type 1.

Figure 2A:
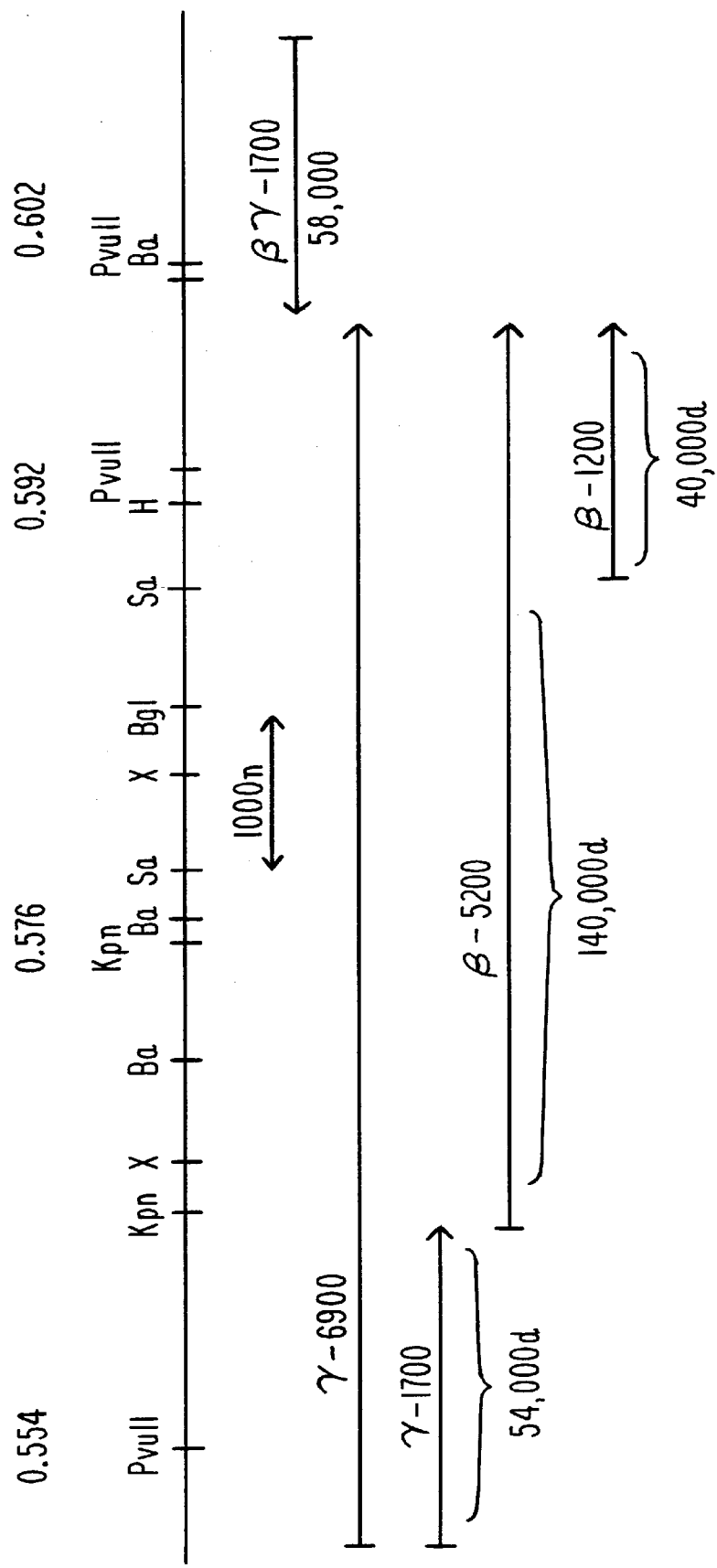
FIG. 2A reflects certain open reading frames (ORFs) including the ORFs for UL39 (140,000d) and UL40 (40,000d) in herpes simplex virus type 1.
Figure 2B:
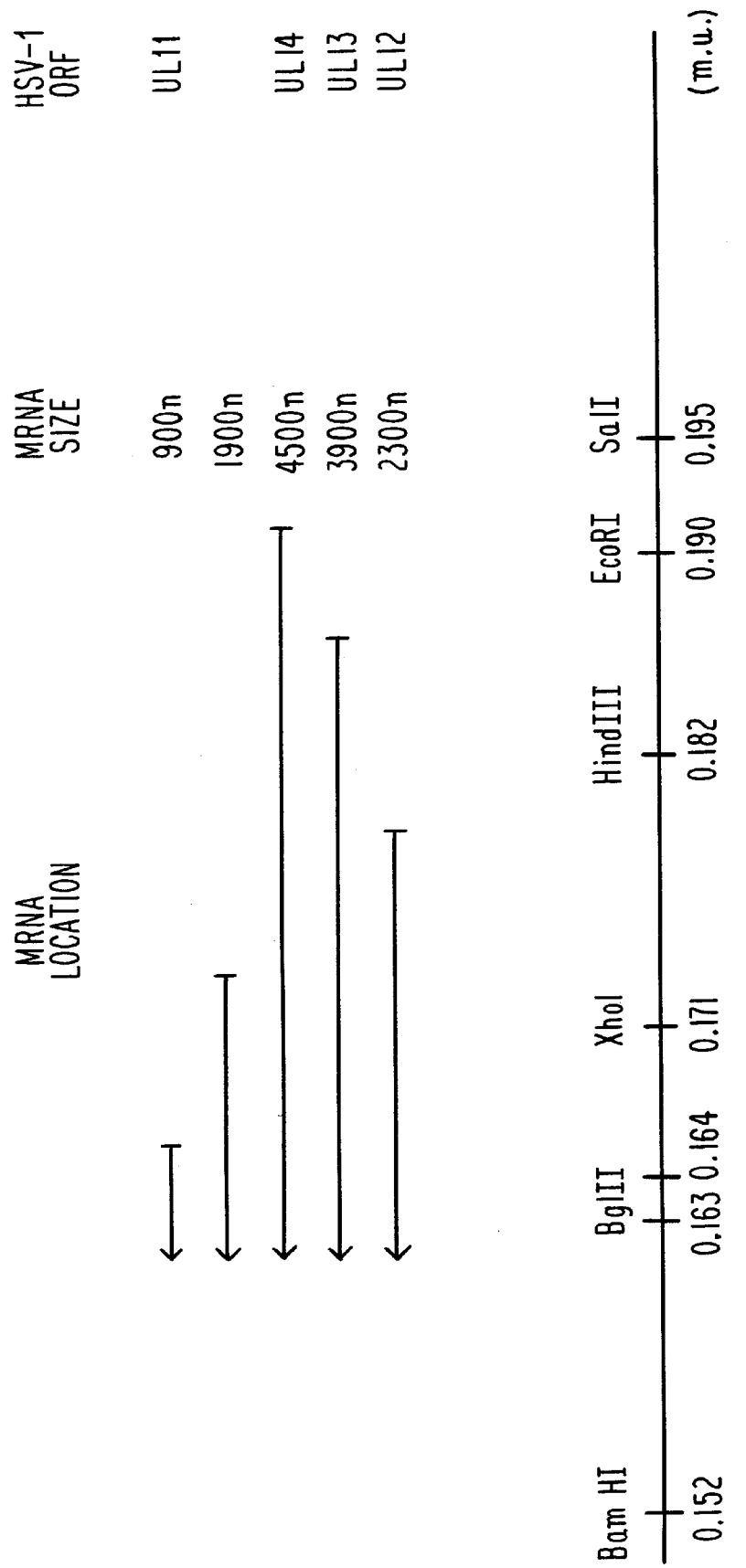
FIG. 2B shows one of a nested set of five 3'-coterminal transcripts including the UL13 gene of HSV-1, strain 17.

The UL13 protein of HSV-1 is a virion capsid protein which putatively encodes a protein kinase activity that is responsible for the specific phosphorylation of virion capsid proteins. The protein is encoded by a 4.1 kb mRNA which is one of a nested set of five 3'-coterminal transcripts as depicted in FIG. 2. The UL13 mRNA is a minor viral species which first appears at 3–4 hours after the onset of viral replication in tissue culture. The abundance of the UL13 mRNA increases somewhat after viral DNA replication occurs but remains low relative to the abundances of the major viral mRNAs throughout late times of infection. It has now been found through DNA sequence analysis that the mRNA sequence encoding UL13 is highly conserved among HSV-1 and HSV-2 isolates. The predicted molecular weights of the HSV-1 and HSV-2 proteins are 57193 and 57001, respectively. Because the synthesis of UL13 protein is not detected until after the onset of viral DNA synthesis, it is assumed that the primary control of UL13 translation is the abundance of the 4.1 kb mRNA. The role, if any, of the 5'non-translated region of the 4.1 kb mRNA in controlling the rate of UL13 protein synthesis has not been examined. A comparison of the translational open reading frames (ORFs) of the HSV-1 and HSV-2 mRNA species depicted in FIG. 3 reveals a conserved nucleotide sequence which is an attractive target for oligonucleotide inhibition of HSV UL13 synthesis and viral replication. The similarity in nucleotide sequence in this region (mismatches are only 205 of 1554 nucleotides) reflects an important structural feature of the mRNA which, it has now been found, can be exploited by antisense oligonucleotide therapy to achieve broad antisense inhibitory activity against both HSV-1 and HSV-2 with single oligonucleotide sequences.

The UL39 protein of HSV-1 is closely associated with a second protein which is encoded by a neighboring gene, UL40, to form a complex that exhibits a ribonucleotide reductase activity. See Frame, M. C., Marsden, H. S., and Dutia, B. M.; *J. Gen. Virol.* 66: 1581–1587 (1985). A homologous set of proteins is encoded by HSV-2 and exhibits a similar ribonucleotide reductase activity. Alone, the HSV-2 homolog of the UL39 protein possesses an autophosphorylating protein kinase activity. A similar kinase activity has not been demonstrated for the HSV-1 UL39 protein. The UL39 and UL40 proteins are encoded by a pair of 3' coterminal mRNAs which are 5.2 and 1.2 kb in length, respectively. In an HSV-1 infection, the 5.2 kb mRNA is a major mRNA early in infection that decreases in abundance at late times of infection. The 1.2 kb mRNA becomes modestly abundant at early times and remains so throughout the infection. In an HSV-2 infection, the 1.2 kb mRNA homolog is the abundant early species and the 5.2 kb mRNA homolog is only moderately abundant. Again, both species of mRNA are only moderately abundant late in the infection. The biological significance of the differences in mRNA abundances between the HSV species is uncertain, but these differences may have profound effects upon the selection of an effective target for oligonucleotide inhibition of the viral ribonucleotide reductase or protein kinase activities. The proteins of the HSV ribonucleotide reductase complex are synthesized prior to viral DNA replication and the enzymatic activity probably plays an essential role in preparing substrates which are required for DNA synthesis. Inhibition of this important enzymatic function will not only interfere with DNA synthesis but also indirectly inhibit the synthesis of those late protein products whose encoding genes rely upon template abundance to efficiently synthesize the appropriate mRNAs. A comparison of the ORFs of the HSV ribonucleotide reductase mRNAs reveals a degree of nucleotide divergence, as shown in FIG. 4, which may influence intertypic efficacy of the mRNA function. The divergence in nucleotide sequence around the AUG codons may require that separate nucleotide therapeutic preparations be used to inhibit the initiation of HSV-1 and HSV-2 UL39 and UL40 protein synthesis. Other regions within the body of the HSV-1 and HSV-2 UL39 and UL40 ORFs exhibit more extensive DNA homologies such that oligonucleotide preparations which have homologies to these regions may effectively inhibit replication of both HSV-1 and HSV-2.

The genome of HSV-1 contains both cis- and transacting elements which function in viral DNA replication. The cis-acting elements correspond to the origins of DNA replication and the trans-acting elements are the enzymes responsible for HSV-1 DNA replication. Seven of the open reading frames encoded by the HSV-1 genome correspond to the seven complementation groups known to be essential for HSV-1 DNA replication. These seven open reading frames encode the viral DNA polymerase enzyme (UL30), a single-stranded DNA binding protein (UL29), the $ori_s$-binding protein (UL9). a double-stranded DNA binding protein (UL42), and three proteins which comprise the helicase-primase complex (UL5, UL8 and UL52). The DNA sequence of these genes is known only for the HSV-1 genome, but the general colinearity and gross DNA sequence homologies between the HSV-1 and HSV-2 genomos in regions encoding critical viral functions has been established such that it is likely that an oligonucleotide inhibitor for each of these HSV-1 gene functions will be found which will also inhibit functional expression of the homologous HSV-2 gene.

Three HSV gene targets have been reported to be sensitive to antisense inhibitors in in vitro assays. An oligonucleotide comprising a sequence of $[dC]_{28}$ linked internucleosidically by phosphorothioate groups inhibits HSV-2 DNA polymerase activity, but this action appears to be non-specific because the same oligonucleotide has also been shown to interfere with genomic replication of an unrelated virus, Human Immunodeficiency Virus. Cheng, Y-C., Gao, W., Stein, C. A., Cohen, J. S., Dutschman, G. E., and Hanes, R. N.; Abstract and poster presented at Oligonucleotides as Antisense Inhibitors of Gene Expression: Therapeutic Implications, held in Rockville, Md. (1989); Matsukura, M., Shinozuka, K., Zon, G., Mitsuya, H., Reitz, M., Cohen, J. S., and Broder, S.; *Proc. Natl. Acad. Sci. USA* 84: 7706–7710 (1987). Although this oligonucleotide has been shown to inhibit the respective viral replicases, inhibition of viral replication is not realized. Methylphosphonate linked and psoralen-derivitized oligonucleotides complementary to the splice junction acceptor sites of the HSV-1 US1 and US12 mRNAs have been shown to inhibit HSV-1 replication in vitro. Kulka, M., Smith. C. C., Aurelian, L., Fishelevich, R., Meade, K., Miller, P., and T'so, P. O. P.; *Proc. Natl. Acad. Sci. USA* 86: 6868–6872 (1989); and Smith, C. C., Aurelian, L., Reddy, M. P., Miller, P. S., and Ts'o, P. O. P.; *Proc. Nat'l Acad. Sci, USA*, 83, 2787–2792 (1986). These results are intriguing because the target genes have been shown to be non-essential to HSV replication. An oligonucleotide sequence which is complementary to a gene which is essential to the replication of the virus is expected to be a better therapeutic agent than oligonucleotides targeted to non-essential gene products. Proof of this supposition was demonstrated by Ceruzzi and Draper using the HSV-1 UL48 mRNA as a target sequence. Ceruzzi, M, and Draper, K.; *Nucleosides and Nucleotides*, 8: 815–818 (1989). The antiviral efficacy achieved by Ceruzzi and Draper with a natural (phosphodiester-linked) oligonucleotide was reported to be comparable to the efficacy observed by Smith et. al. using their modified oligonucleotides. This increase in antiviral efficacy was probably related to the important role of the UL48 protein in enhancing immediate early transcription of the virus.

The development of a set of oligonucleotide inhibitors of the UL13 capsid protein synthesis and virion protein phosphorylation represents a novel target for anti-HSV chemotherapy. The targeting of a number of independent viral functions offers the opportunity for broad intertypic antiviral activity by using the most highly effective antisense oligonucleotides determined by our studies in combination with each other or with an existing nucleoside therapy. Comparison of the DNA sequences of herpes simplex virus type 1 (HSV-1), varicella zoster virus (VZV) and Epstein Barr virus (EBV) has revealed that the genes which have now been found to be the best targets for antisense oligonucleotide attack are conserved among the human herpesviruses. The VZV and EBV genes which are homologous to the HSV-1 genes are set forth in FIG. 6. The predictions of ORFs are taken from Genbank annotations of published DNA sequences. Davison, A. J. & Scott, J. Z., *J. gen. Virol.* 67: 1759–1816 (1987); McGeoch, D. J., Dalrymple, M. A., Davison, A. J., Dolan, A., Frame, M. C., McNab, D., Perry, L. J., Scott, J. E., & Taylor, P., *J. Gen. Virol.* 69: 1531–1574 (1988); Baer, R., Bankier, A. T., Biggin, M. D., Deininger, P. L., Farrell, P. J., Gibson, T. J., Hatfull, G., Hudson, G. S., Satchwell, S. C., Sequin, C., Tuffnell, P. S., & Barrall, B. G., *Nature* 310: 207–211 (1984).

Although the EBV BBRF2 and BORF2 genes are listed as being homologous to HSV-1 UL9 and UL39 genes, respectively, the encoded amino acids of these genes are not highly homologous. This lack of amino acid homology in the encoded ORFs may reflect a disruption of the EBV ORFs by splicing events within the mRNAs although verification of splices within these mRNAs has not yet been made. A number of regions of nucleotide homology which exist within these various herpesvirus genes are now believed to be good targets for antisense oligonucleotide inhibition. It is believed that an oligonucleotide which inhibits HSV-1 and/or HSV-2 and also possesses homology to the corresponding nucleotide sequence of either VZV or EBV will be an effective inhibitor of VZV and/or EBV replication as well. The sequence of the other human herpesviruses has not been published in toto, but limited nucleotide data available has shown that Human Cytomegalovirus (HCMV) and Human Herpesvirus 6 (HHV 6) have homology to the HSV-1 UL13 gene. Lawrence, G. L., Chee, M., Craxton, M. A., Gompels, U. A., Honess, R. W., and Barrell, B. G.; *J. Virol.* 64: 287–299 (1989). Additionally, the DNA sequence of the HCMV homolog of the HSV-1 UL30 gene has been published (Kouzarides, T., Bankier, A. T., Satchwell, S. C., Weston, K., Tomlinson, P., and Barrell, B. G.; *J. Virol* 61: 125–133 (1987) and shown to exhibit regions of homology to the HSV-1 gene. Once the sequences of other human herpesviruses are known, it is believed that the genes which have now been targeted will be retained at least in part and show significant nucleotide homology to the original HSV gene sequences. The present invention employs oligonucleotides and oligonucleotide analogs for use in antisense inhibition of the function of messenger RNAs of herpesviruses. In the context of this invention, the term "oligonucleotide" refers to a plurality of joined nucleotide units formed from naturally-occurring bases and cyclofuranosyl groups joined by native phosphodiester bonds. This term effectively refers to naturally-occurring species or synthetic species formed from naturally-occurring subunits.

"Oligonucleotide analog," as that term is used in connection with this invention, refers to moieties which function similarly to oligonucleotides but which have non naturally-occurring portions. Thus, oligonucleotide analogs may have altered sugar moieties or inter-sugar linkages. Exemplary among these are the phosphorothioate and other sulfur containing species which are known for use in the art. They may also comprise altered base units or other modifications consistent with the spirit of this invention.

In accordance with certain preferred embodiments, at least some of the phosphodiester bonds of the oligonucleotide have been substituted with a structure which functions to enhance the ability of the compositions to penetrate into the region of cells where the RNA whose activity is to be modulated is located. It is preferred that such linkages be sulfur-containing. It is presently preferred that such substitutions comprise phosphorothioate bonds. Others such as alkyl phosphorothioate bonds, N-alkyl phosphoramidates, phosphorodithioates, alkyl phosphonates, and short chain alkyl or cycloalkyl structures may also be useful. In accordance with other preferred embodiments, the phosphodiester bonds are substituted with structures which are, at once, substantially non-ionic and non-chiral. Persons of ordinary skill in the art will be able to select other linkages for use in the practice of the invention.

Oligonucleotide analogs may also include species which include at least some modified base forms. Thus, purines and pyrimidines other than those normally found in nature may be so employed. Similarly, modifications on the cyclofuranose portions of the nucleotide subunits may also occur an long as the essential tenets of this invention are adhered to.

Such analogs are best described as being functionally interchangeable with natural oligonucleotides (or synthesized oligonucleotides along natural lines), but which have one or more differences from natural structure. All such analogs are comprehended by this invention so long as they function effectively to hybridize with messenger RNA of herpesvirus or related viruses to inhibit the function of that RNA. The oligonucleotides and oligonucleotide analogs in accordance with this invention preferably comprise from about 6 to about 50 subunits. It is more preferred that such oligonucleotides and analogs comprise from about 8 to about 25 subunits. As will be appreciated, a subunits is a base and sugar combination suitably bound to adjacent subunits through phosphodiester or other bonds.

The oligonucleotides and oligonucleotide analogs of this invention are designed to be hybridizable with messenger RNA of herpesvirus. Such hybridization, when accomplished, interferes with the normal function of the messenger RNA to cause a loss of its utility to the virus. The functions of messenger RNA to be interfered-with include all vital functions such as translocation of the RNA to the situs for protein translation, actual translation of protein from the RNA, and possibly even independent catalytic activity which may be engaged in by the RNA. The overall effect of such interference with the RNA function is to cause the herpesvirus to lose the benefit of the RNA and, overall, to experience interference with expression of the viral genome. Such interference is generally fatal to the virus.

In accordance with the present invention, it is preferred to provide oligonucleotides and oligonucleotide analogs designed to interfere with messenger RNAs determined to be of enhanced metabolic significance to the virus as described above. It has been found to be preferred to target one or more translation initiation portions of an open reading frame for antisense attack. As will be appreciated, such portions generally comprise the sequence AUG (in RNA) such that the oligonucleotide sequence CAT will be specifically hybridizable therewith. Accordingly, oligonucleotides and oligonucleotide analogs comprising the CAT sequence are preferred for these embodiments. Additional nucleotide subunits are preferably included in the oligonucleotide or oligonucleotide analog such that specific hybridization with the nucleic acid is attained to a high degree. Accordingly a number of subunits on one or either "side" of the CAT sequence which are designed to be complementary to the sequence adjacent to the translation initiation site to be hybridized with are included in the preferred oligonucleotides or analogs. Six to twelve subunits so adjacent on either "side" are convenient and are presently preferred, however larger or smaller numbers may be profitably employed without deviating from the spirit of this invention.

The oligonucleotides and oligonucleotide analogs of this invention can be used in diagnostics, therapeutics and as research reagents and kits. For therapeutic use, the oligonucleotide or oligonucleotide analog is administered to an animal, especially a human, suffering from a herpesvirus infection such as genital herpes, herpes simplex gingivostomatitis, herpes labialis, herpes simplex encephalitis, keratoconjunctivitis, herpetic whitlow or disseminated herpes infections of neonates and immunocompromised hosts.

It is generally preferred to apply the therapeutic agent in accordance with this invention topically or intralesionally. Other forms of administration, such as orally, transdermally, intravenously or intramuscularly may also be useful. Inclusion in suppositories may also be useful. Use of the oligonucleotides and oligonucleotide analogs of this invention in prophylaxis is also likely to be useful. Such may be accomplished, for example, by providing the medicament as a coating in gloves, condoms and the like. Use of pharmacologically acceptable carriers is also preferred for some embodiments.

The present invention is also useful in diagnostics and in research. Since the oligonucleotides and oligonucleotide analogs of this invention hybridize to herpesvirus, sandwich and other assays can easily be constructed to exploit this fact. Provision of means for detecting hybridization of oligonucleotide or analog with herpesvirus present in a sample suspected of containing it can routinely be accomplished. Such provision may include enzyme conjugation, radiolabelling or any other suitable detection systems. Kits for detecting the presence or absence of herpesvirus may also be prepared.

In accordance with the teachings of the invention, a number of complementary oligonucleotides which are targeted to the translation initiation regions of selected HSV mRNAs were made (Table 8). Natural oligonucleotides containing a phosphodiester backbone were screened for anti-HSV activity in an infectious yield assay. The oligonucleotide (ISIS 1049) which showed the best activity in this assay was targeted to an internal translation initiation codon of the HSV-2 homolog of the HSV-1 UL13 gene. Synthesis of methylphosphonate and phosphorothioate analogs of this active sequence showed that the phosphorothioate backbone modification greatly enhanced the antiviral activity of the oligonucleotide over that observed with either the phosphodiester or methylphosphonate oligonucleotides. Rabbit reticulocyte translation of in vitro synthesized HSV-1 and HSV-2 UL13 RNA demonstrated that oligonucleotides containing either a phosphodiestor (ISIS 1049) or a phosphorothioate (ISIS 1082) backbone structure could inhibit the synthesis of the UL13 polypeptide. Dose response experiments compared the antiviral activity of ISIS 1082 with that of acycloguanosine (ACV) in two ACV$^r$ strains of HSV-1 PAAr$^5$, a KOS mutant which has an altered nucleotide binding site in the viral DNA polymerase gene and DM2.1 which contains a deletion of the viral thymidine kinase gene. The activity of ISIS 1082 in these assays showed that the oligonucleotide does not require phosphorylation by the viral thymidine kinase for activation and indicated that the oligonucleotide does not interact with the viral DNA polymerase at the PAA and ACV binding site. In vitro assessment of the cellular toxicity of ISIS 1082 demonstrated that the predicted therapeutic index for the compound is equivalent to or better than that predicted for ACV in parallel assays. The demonstration that ISIS 1082 shows antiviral activity in ACV-resistant strains of virus and the favorable therapeutic index observed with the compound underscore the potential clinical value of this class of antiviral compounds.

Antisense oligonucleotides have been shown to inhibit the replication of virus in cell culture. Little is known, however, about the effectiveness of antisense oligonucleotides in animal models of viral infection. Animal models of HSV induced keratitis are well suited for such studies. Such ocular HSV infections are usually treated topically and thus provide a relatively simple way to test the effectiveness of antisense oligonucleotides in vivo. The drugs can be applied topically in aqueous solution and several parameters of the infection can be monitored. Using a murine model, the effectiveness of a phosphorothioate antisense oligonucleotide made in accordance with the teachings of the invention was tested for treatment of herpetic keratitis. The oligonucleotide was directed against the UL13 gene of HSV-1 having the sequence GCCGAGGTCCATGTCGTACGC (ISIS 1082; SEQ ID NO.: 7). It was found that topical treatment with this anti-UL13 oligonucleotide significantly reduced the severity of HSV induced stromal keratitis.

Figure 7A:
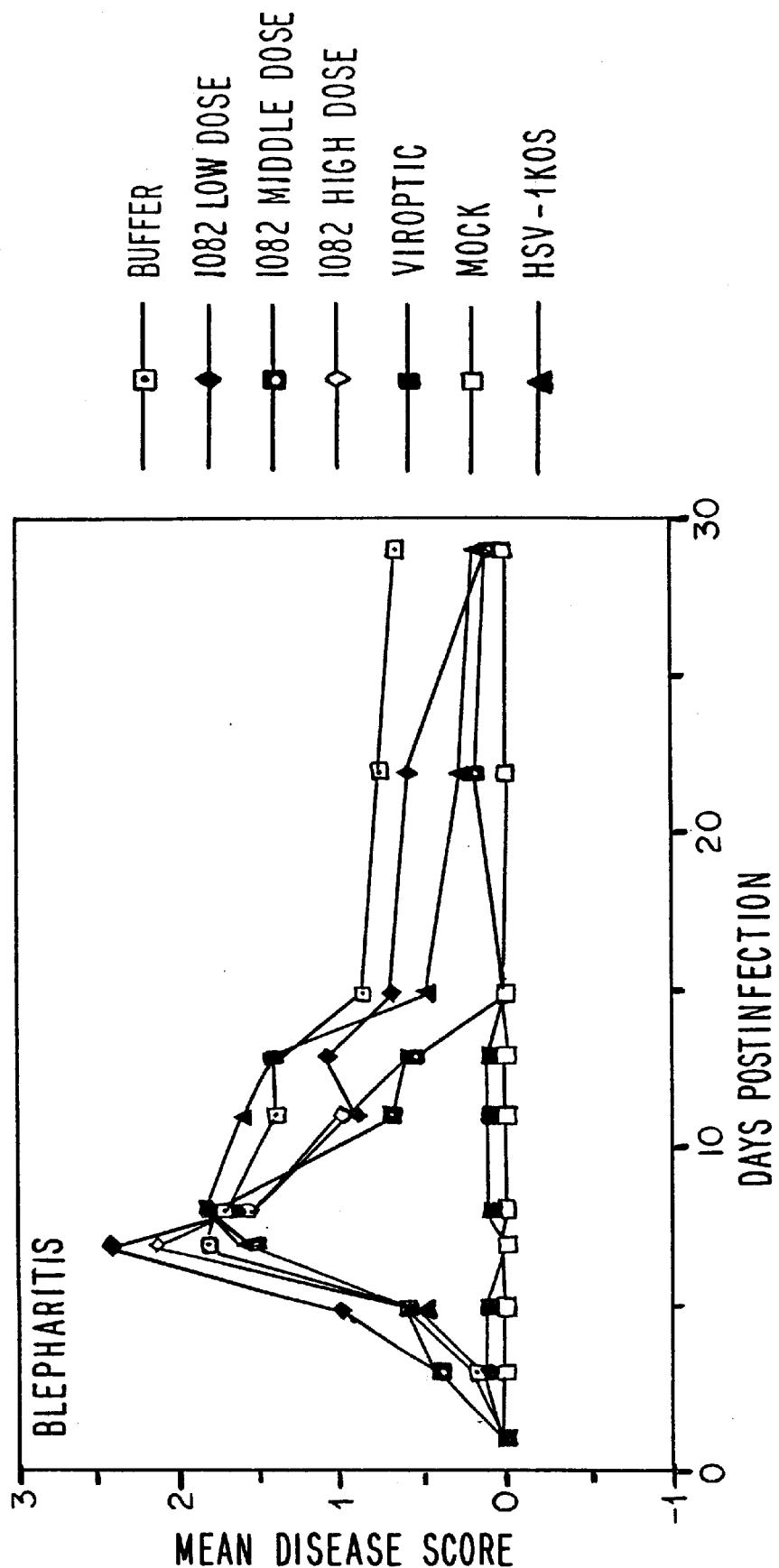
FIG. 7 is a graphical depiction showing mean disease scores at various times after infection. Mice were infected with $1\times10^5$ pfu of HSV-1 KOS and treatment was begun 4 hours pi. Each data point represents the mean disease scores of all mice in the group on the day indicated.
Figure 7B:
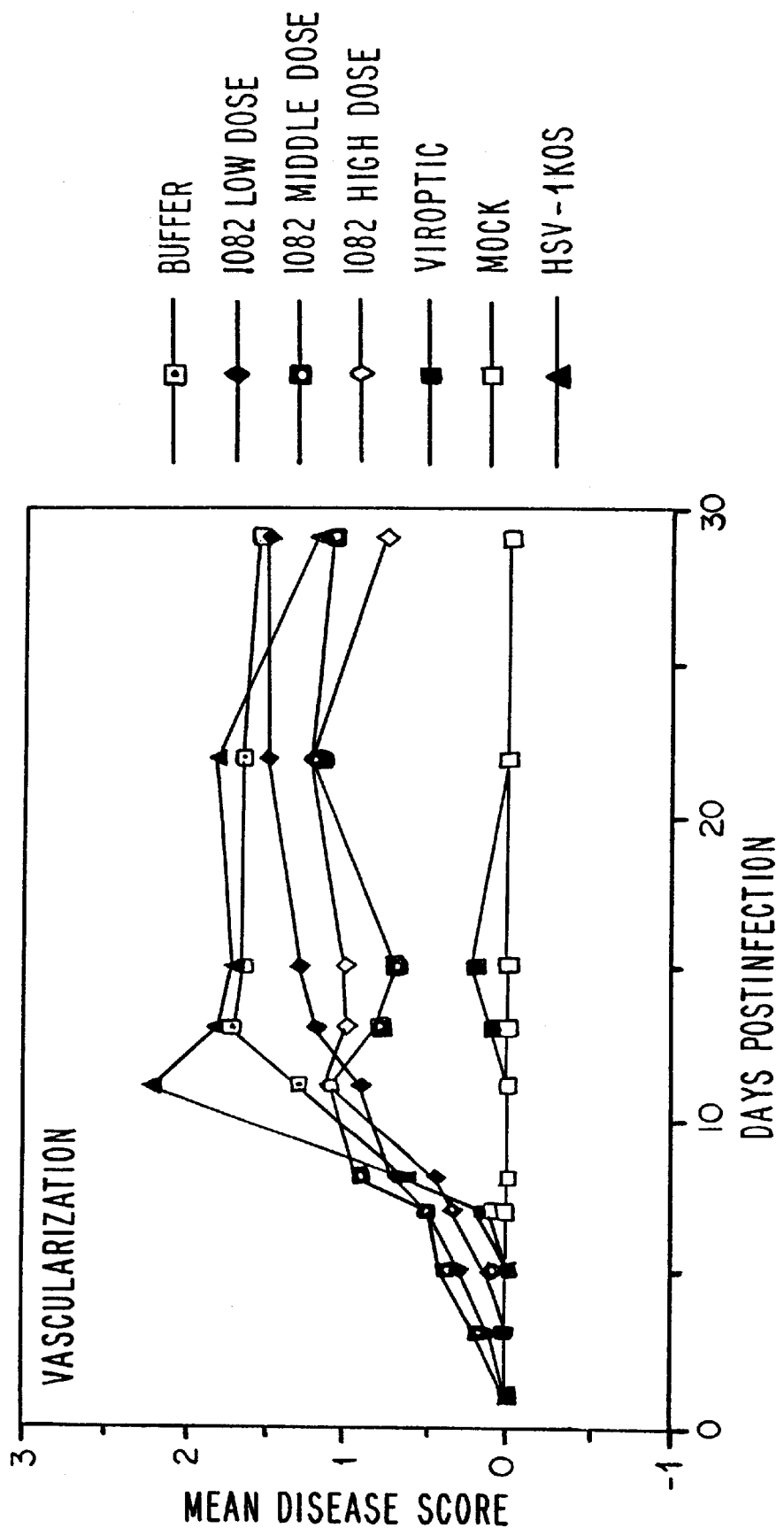
Figure 7C:
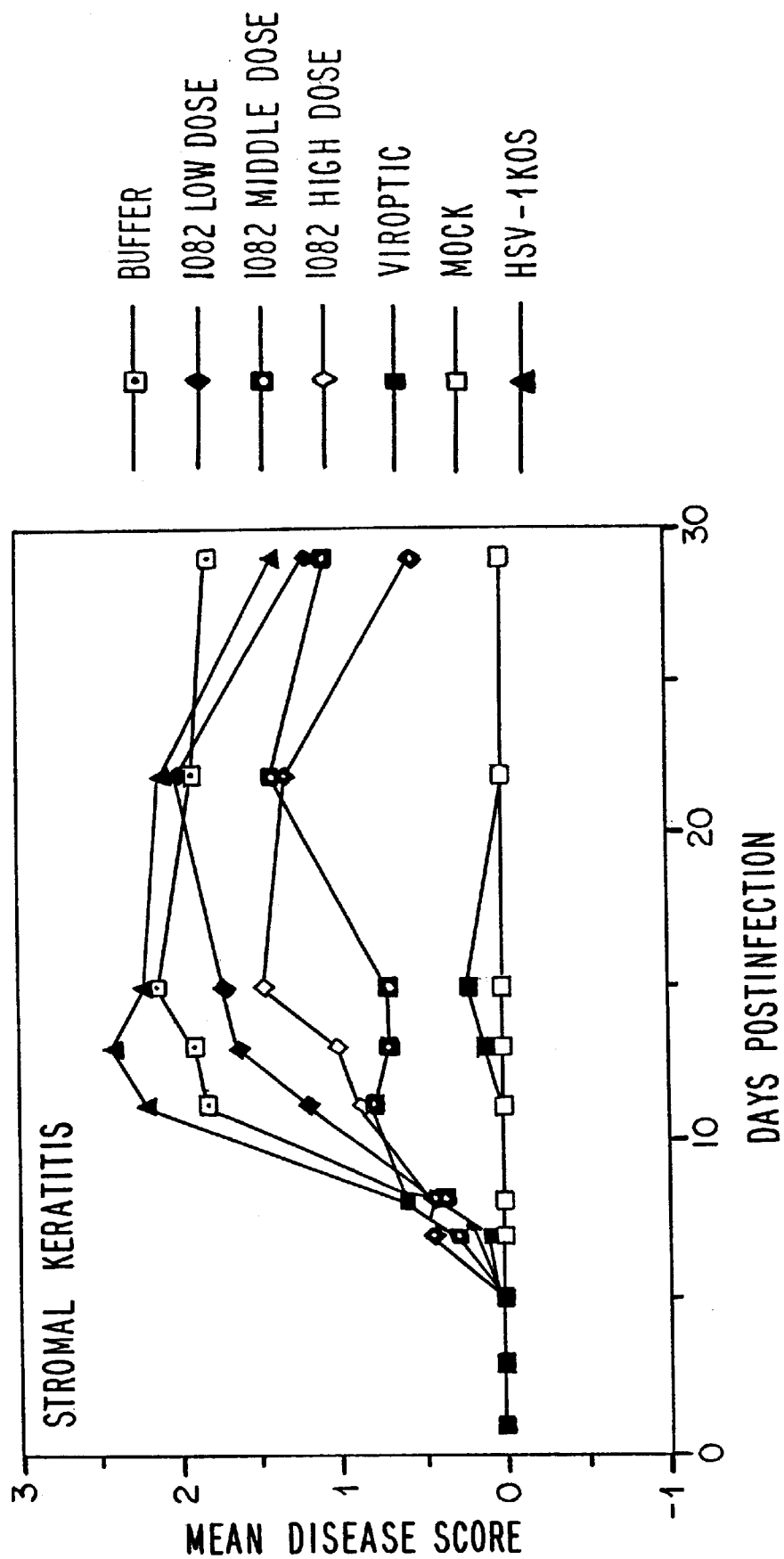
Figure 8A:
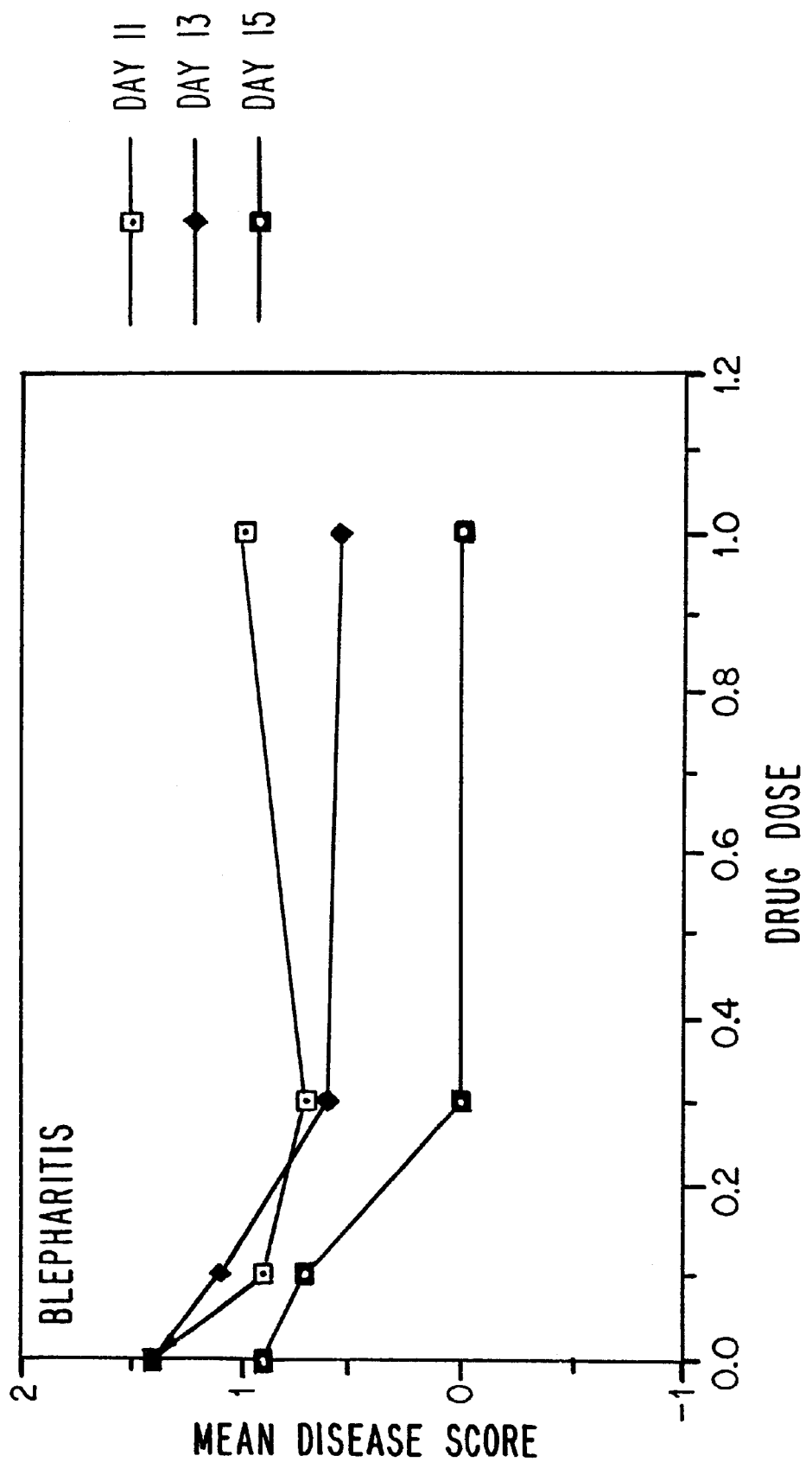
FIG. 8 is a graphical depiction showing the effect of drug dose on disease scores. The mean disease scores are plotted v. the dose of ISIS 1082 for days 11, 13 and 15 post infection.
Figure 8B:
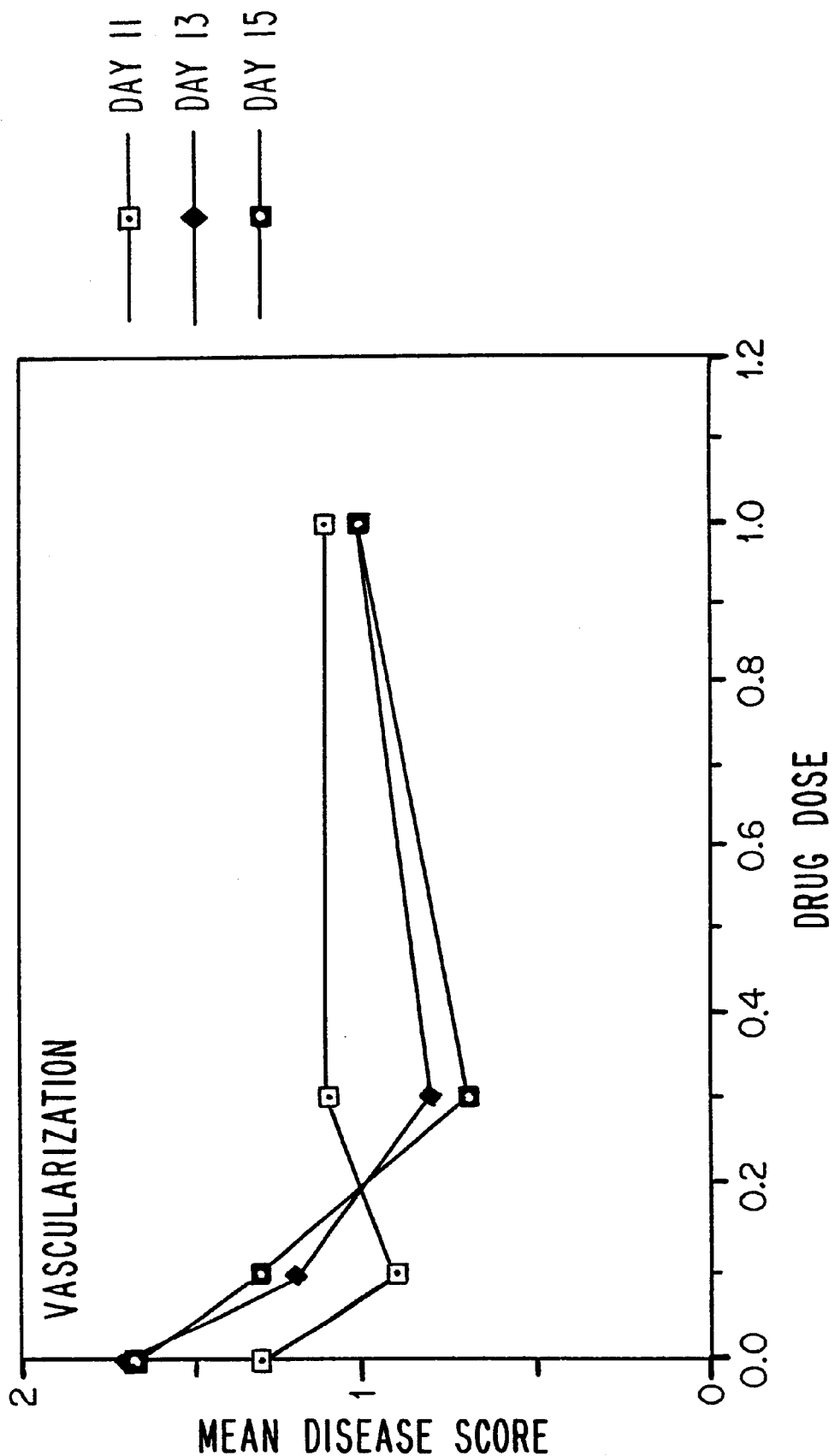
Figure 8C:
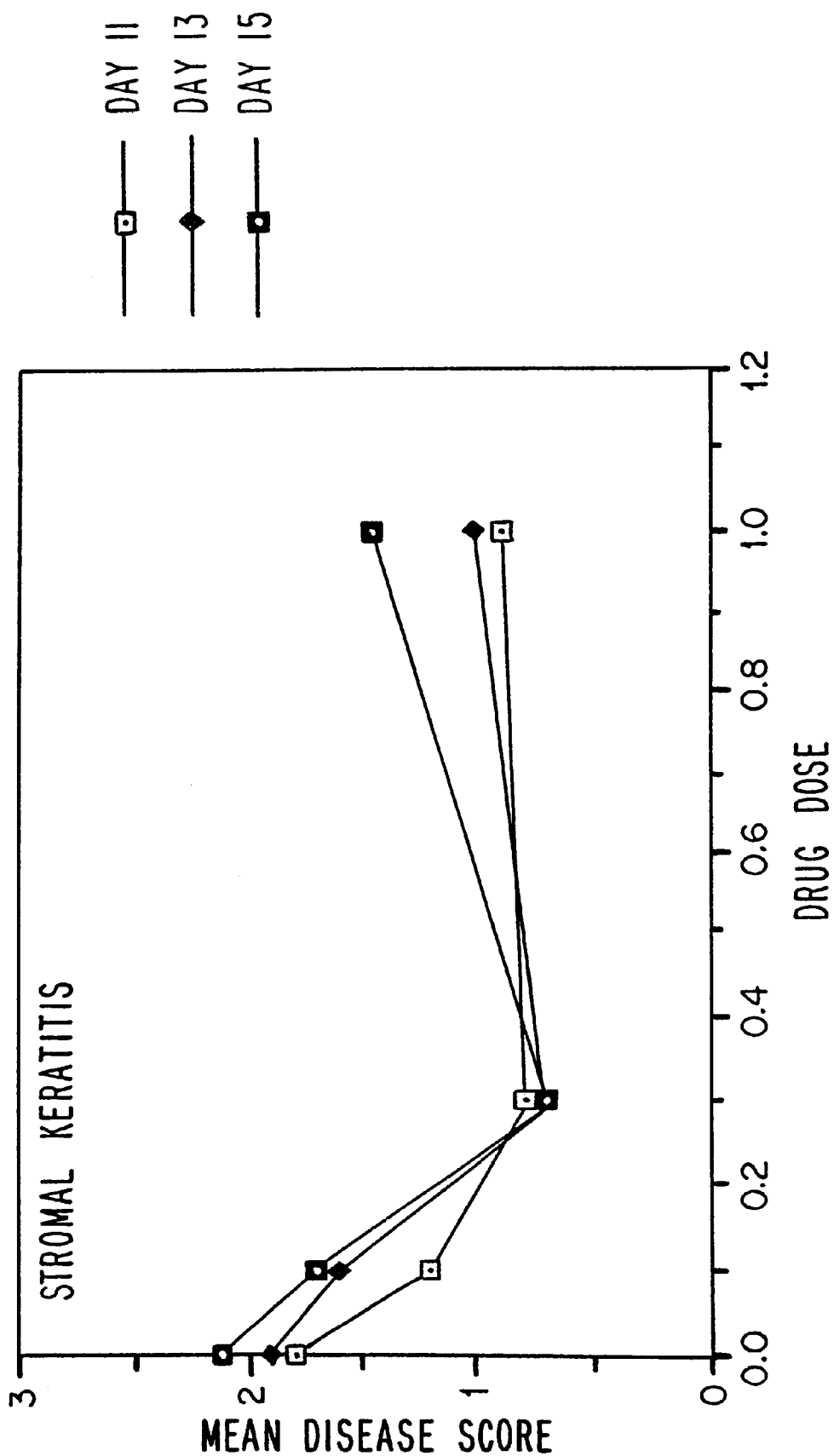

Three different concentrations of the oligonucleotide as well as a buffer control (50 mM sodium acetate, pH5.8, 0.15 M NaCl) and untreated animals infected with HSV-1 were tested. All animals were infected with $1 \times 10^5$ plaque forming units (pfu) following scratching of the cornea. It was found that treatment with 0.3% and 1.0% ISIS 1082 did not affect the severity of blepharitis, but mice treated with 0.3% and 1.0% ISIS 1082 healed slightly faster (FIG. 7). Treatment with ISIS 1082 reduced stromal disease and vascularization on days 11, 13, and 15 post-infection (FIG. 7). This reduction in disease was statistically significant on some days but not on others, probably because of small sample size and variability in the disease. A comparison of dose vs disease scores as shown in FIG. 8, indicated that ISIS 1082 has a narrow effective concentration range. The doses causing a 50% reduction in disease scores on day 15 post-infection were 0.17%, 0.25%, and 0.22% for blepharitis, vascularization and stromal diseases, respectively. These results indicate that antisense oligonucleotides of the invention may be useful in treating HSV keratitis.

The invention is further illustrated by the following examples which are meant to be illustrations only and are not intended to limit the present invention to specific embodiments

EXAMPLES

Example 1

HeLa (ATCC #CCL2) and Vero (ATCC #CCL81) cells used were obtained from the American Tissue Culture Collection. Cultures of HeLa cells were grown in Dulbecco's Modified Essential Medium (D-MEM) supplemented with 10% fetal bovine serum (FBS), penicillin (100 units/ml), streptomycin (100 micrograms/ml), and L-glutamine (2mM). Cultures of Vero cells were grown in D-MEN supplemented with 5.0% FBS, penicillin, streptomycin and L-glutamine. Stock cultures of HSV-1 (strain KOS) and HSV-2 (strain HG52) were grown in Vero cells using low multiplicity infections (multiplicity of infection [MOI]=0 02 plaque forming units [pfu]/cell).

To assess the ability of oligonucleotides to inhibit HSV replication, an infectious yield assay was employed. HeLa cells were seeded at a density of $5 \times 10^5$ cells per well in Falcon 6 well tissue culture plates. cells were overlaid with 3 ml of medium (D-MEM with 10% FBS) and incubated at 37° C. for 18–24 hours. Where appropriate, cells were overlaid with oligonucleotide preparations in 1 ml of culture medium at 24 hours after seeding the plates. Following an 18 hours incubation, all wells were rinsed with phosphate buffered saline and infected with either HSV-1 or HSV-2 at varying multiplicities of infection (MOI) suspended in 0.5 ml of serum-free D-MEM. Virus and cells were incubated at 37° C. for 1 hour with occasional rocking. Following viral adsorption, unadsorbed virus was rinsed away by washing the cells with phosphate buffered saline. Where appropriate, 1 ml of medium (D-MEM with 10% PBS) containing 4 µM concentrations of oligonucleotide wore added to the well and the cells were incubated for 48 hours at 37° C. Again, control wells received 1 ml of medium which contained no oligonucleotide.

The oligonucleotides used were designed to interfere with translation of either UL13, UL39 or UL40 mRNAs at a translation initiation region. Unmodified oligodeoxynucleotides were synthesized on an Applied Biosystems 380B DNA Synthesizer using standard phosphoramidite chemistry with oxidation by iodine. The reagents, both CPG-bound and β-cyanoethyldiisopropylphosphoramidites, were purchased from Applied Biosystems, Inc. (Foster City, Calif.). The standard oxidation bottle was replaced by 0.2 M solution of $^3$H-1,2-benzodithiole-3-one 1,1-dioxide (Iyer et al., (1990) *J. Am. Chem. Soc.*, 112, 1253–1254) in acetonitrile for the stepwise thiation of the phosphite linkages. The thiation cycle wait step was increased to 68 seconds and was followed by the capping step. After cleavage from the CPG-column and deblocking in concentrated ammonium hydroxide at 55° C. (18 hours), the phosphorothioates were purified by trityl-on HPLC with a PRP-1 column using a gradient of acetonitrile in 50 mM of triethyl-ammonium acetate, pH 7 (4% to 32% in 30 minutes, flow rate of 1.5 ml/minute). Appropriate fractions were pooled, evaporated, and treated with 5.0% acetic acid at ambient temperature for 15 minutes. The solution was extracted with an equal volume of ethyl acetate, neutralized with ammonium hydroxide, frozen and lyophilized. Analytical gel electrophoresis was accomplished in 20% acrylamide, 8 M urea, 45 mM-tris-borate buffer, pH 7, 40 V/cm. Oligodeoxynucleotides and their phosphorothioate analogs were judged from HPLC analysis and by polyacrylamide gal electrophoresis to be greater than 95% full length material.

The relative amounts of phosphorothioate and phosphodiester linkages obtained by our synthesis were determined by $^{31}$P NMR spectroscopy. The spectra were acquired on a Varian NMR spectrometer with a $^{31}$p frequency of 162 MHz. Typically, 1000 transients are co-added. A relaxation delay of 7.5 sac between transients is used to insure a fully relaxed spectrum. The $^{31}$P spectra are acquired at ambient temperature using deuterium oxide or dimethyl sulfoxide-$d_6$ as a solvent. Phosphorothioate samples typically contained less than one percent of phosphodiester linkages.

The sequences prepared are shown in Table 1.

TABLE 1

| HSV GENE | TYPE | OLIGONUCLEOTIDE SEQUENCE 5'                3' | (SEQ ID NO.:) | NORMAL STRUC. CODE # | PHOSPHO- THIOATE CODE # |
|---|---|---|---|---|---|
| UL48 | 1 | GTC CGC GTC CAT GTC GGC | 1 | 01 | 37 |
| UL13 | 1 | GGA CTC ATC CAT CCT TCG GCC | 2 | 02 | 34 |
| UL39 | 1 | GCG GCT GGC CAT TTC AAC AGA | 3 | 03 | 35 |
| UL40 | 1 | CGC GGA ATC CAT GGC AGC AGG | 4 | 04 | 36 |
| UL13 | 1 | ACC GAG GTC CAT GTC GTA CGC | 5 | 05 | 38 |
| UL13 | 2 | GGA CTC ATC CAT CCG TCC GCC | 6 | 06 | 39 |
| UL13 | 2 | GCC GAG GTC CAT GTC GTA CGC | 7 | 07 | 40 |
| UL39 | 2 | GCG GTT GGC CAT TGG AAC CAA | 8 | 08 | 41 |

Virus was harvested into the overlay medium and triplicate wells of each experimental point were combined and standardized to a volume of 3 ml. The suspension wars frozen and thawed four times, then drawn through a 20 gauge needle four times and stored at −80° C. in 2 ml aliquots. Alternatively, each well was harvested and prepared for replicate titrations at each experimental point. This latter protocol was used in the generation of dose response curves for individual strains of HSV-1. Virus titer was determined by plaque assay on Vero cell monolayers. Dilutions of each virus preparation were prepared and duplicate aliquots of each dilution were adsorbed onto Vero cells for 1 hour with occasional rocking. After adsorption, the virus inoculum was removed by rinsing the plates with phosphate buffered saline and the cells were overlaid with 2 ml of D-MEN containing 5.0% FBS and 0.75% methyl cellulose. Cells were incubated at 37° C. for 72 hours before plaques were fixed with formalin, stained with crystal violet and counted. Plaque counts from treated wells were compared to those from the control wells to establish the degree of inhibition of virus replication.

Table 2 sets forth the data collected. The virus type, HSV-1 or HSV-2 and multiplicity of infection, MOI, are set forth. Inhibition of replication may be seen through comparison of experimental and control values.

TABLE 2

| Virus Type | MOI | Oligo. | Yield 1 | Yield 2 | Average |
|---|---|---|---|---|---|
| HSV-1 | 0.5 | none | 5.4E+08 | 6.2E+08 | 5.80E+08 |
| HSV-1 | 0.5 | 01 | 6.3E+08 | 7.0E+08 | 6.65E+08 |
| HSV-1 | 0.5 | 03 | 7.7E+08 | 8.0E+08 | 7.85E+08 |
| HSV-1 | 0.5 | 04 | 3.9E+08 | 5.7E+08 | 4.80E+08 |
| HSV-1 | 0.5 | 05 | 7.7E+08 | 9.3E+08 | 8.50E+08 |
| HSV-1 | 0.5 | 08 | 7.9E+08 | 8.9E+08 | 8.40E+08 |
| HSV-1 | 0.5 | 42 | 5.7E+07 | 7.5E+07 | 6.60E+07 |
| HSV-1 | 0.5 | 39 | 1.4E+06 | 1.7E+06 | 1.55E+06 |
| HSV-1 | 0.5 | 41 | 1.2E+06 | 2.6E+06 | 1.90E+06 |
| HSV-2 | 0.5 | none | 8.0E+07 | 9.1E+07 | 8.55E+07 |
| HSV-2 | 0.5 | 01 | 7.6E+07 | 8.5E+07 | 8.05E+07 |
| HSV-2 | 0.5 | 03 | 8.3E+07 | 9.5E+07 | 8.90E+07 |
| HSV-2 | 0.5 | 04 | 4.9E+07 | 6.3E+07 | 5.60E+07 |
| HSV-2 | 0.5 | 05 | 6.6E+07 | 7.5E+07 | 7.05E+07 |
| HSV-2 | 0.5 | 08 | 5.1E+07 | 6.2E+07 | 5.65E+07 |
| HSV-2 | 0.5 | 39 | 5.0E+05 | 7.0E+05 | 6.00E+05 |
| HSV-2 | 0.5 | 41 | 3.0E+05 | 7.0E+05 | 5.00E+05 |
| HSV-1 | 0.5 | none | 6.0E+07 | 7.6E+07 | 6.80E+07 |
| HSV-1 | 0.5 | 01 | 1.2E+08 | 1.2E+08 | 1.20E+08 |
| HSV-1 | 0.5 | 03 | 1.3E+08 | 1.7E+08 | 1.50E+08 |
| HSV-1 | 0.5 | 07 | 8.9E+07 | 9.5E+07 | 9.20E+07 |
| HSV-1 | 0.5 | 08 | 9.0E+07 | 1.2E+08 | 1.05E+08 |
| HSV-1 | 0.5 | 09 | 1.5E+08 | 1.8E+08 | 1.64E+08 |
| HSV-1 | 0.5 | 35 | 1.7E+07 | 2.0E+07 | 1.85E+07 |
| HSV-1 | 0.5 | 37 | 3.5E+07 | 4.7E+07 | 4.10E+07 |
| HSV-1 | 0.5 | 38 | 5.7E+06 | 7.1E+06 | 6.40E+06 |
| HSV-1 | 0.5 | 40 | 1.7E+09 | 2.1E+09 | 1.86E+09 |
| HSV-1 | 0.05 | none | 2.8E+08 | 3.3E+08 | 3.05E+08 |
| HSV-1 | 0.05 | 03 | 3.5E+08 | 4.7E+08 | 4.10E+08 |
| HSV-1 | 0.05 | 07 | 2.6E+08 | 3.2E+08 | 2.90E+08 |
| HSV-1 | 0.05 | 08 | 3.0E+08 | 4.3E+08 | 3.65E+08 |
| HSV-1 | 0.05 | 09 | 3.5E+08 | 3.7E+08 | 3.60E+08 |
| HSV-1 | 0.05 | 35 | 4.2E+05 | 6.0E+05 | 5.10E+05 |
| HSV-1 | 0.05 | 37 | 2.9E+06 | 3.2E+06 | 3.05E+06 |
| HSV-1 | 0.05 | 38 | 2.5E+05 | 3.9E+05 | 3.20E+05 |
| HSV-1 | 2.5 | none | 1.5E+08 | 2.5E+08 | 2.00E+08 |
| HSV-1 | 2.5 | 01 | 4.0E+08 | 7.1E+08 | 5.55E+08 |
| HSV-1 | 2.5 | 02 | 6.2E+08 | 7.6E+08 | 6.90E+08 |
| HSV-1 | 2.5 | 03 | 4.0E+08 | 4.3E+08 | 4.15E+08 |
| HSV-1 | 2.5 | 04 | 5.0E+08 | 6.1E+08 | 5.55E+08 |
| HSV-1 | 2.5 | 06 | 5.4E+08 | 6.1E+08 | 5.75E+08 |
| HSV-1 | 2.5 | 07 | 2.9E+08 | 4.1E+08 | 3.50E+08 |
| HSV-1 | 0.25 | none | 7.7E+07 | 8.4E+07 | 8.05E+07 |
| HSV-1 | 0.25 | 01 | 6.5E+07 | 7.0E+07 | 6.75E+07 |
| HSV-1 | 0.25 | 02 | 5.9E+07 | 7.0E+07 | 6.45E+07 |
| HSV-1 | 0.25 | 03 | 5.4E+07 | 6.4E+07 | 5.90E+07 |
| HSV-1 | 0.25 | 04 | 5.2E+07 | 7.1E+07 | 6.15E+07 |
| HSV-1 | 0.25 | 06 | 6.7E+07 | 7.2E+07 | 6.95E+07 |
| HSV-1 | 0.25 | 07 | 2.1E+07 | 4.3E+07 | 3.20E+07 |
| HSV-2 | 1.5 | none | 1.3E+08 | 1.7E+08 | 1.48E+08 |
| HSV-2 | 1.5 | 01 | 5.9E+07 | 5.8E+07 | 5.85E+07 |
| HSV-2 | 1.5 | 02 | 5.3E+07 | 6.4E+07 | 5.85E+07 |
| HSV-2 | 1.5 | 03 | 1.1E+08 | 1.2E+08 | 1.15E+08 |
| HSV-2 | 1.5 | 04 | 1.3E+08 | 1.3E+08 | 1.28E+08 |
| HSV-2 | 1.5 | 06 | 1.1E+08 | 1.2E+08 | 1.12E+08 |
| HSV-2 | 1.5 | 07 | 5.0E+07 | 5.4E+07 | 5.20E+07 |
| HSV-2 | 1.5 | 08 | 8.7E+07 |  | 8.70E+07 |
| HSV-2 | 0.15 | none | 8.0E+07 | 8.4E+07 | 8.20E+07 |
| HSV-2 | 0.15 | 01 | 2.8E+07 | 3.1E+07 | 2.95E+07 |
| HSV-2 | 0.15 | 02 | 7.3E+07 | 8.5E+07 | 7.90E+07 |
| HSV-2 | 0.15 | 03 | 4.4E+07 | 5.0E+07 | 4.70E+07 |
| HSV-2 | 0.15 | 04 | 6.7E+07 | 7.2E+07 | 6.95E+07 |
| HSV-2 | 0.15 | 06 | 4.4E+07 | 4.8E+07 | 4.60E+07 |
| HSV-2 | 0.15 | 07 | 5.0E+07 | 5.4E+07 | 5.20E+07 |
| HSV-2 | 0.15 | 08 | 4.0E+07 | 4.1E+07 | 4.05E+07 |

The following data were collected in a similar fashion except that the cells were pre-exposed to oligonucleotide for 5 hours rather than 18 hours. In some cases, as indicated, higher oligonucleotide concentrations were employed.

TABLE 3

| Virus Type | MOI | Oligo. | Yield 1 | Yield 2 | Average | |
|---|---|---|---|---|---|---|
| HSV-1 | 0.5 | none | 6.1E+08 | 6.8E+08 | 6.45E+08 | |
| HSV-1 | 0.5 | 01 | 6.4E+08 | 7.4E+08 | 6.90E+08 | |
| HSV-1 | 0.5 | 02 | 6.2E+08 | 6.5E+08 | 6.35E+08 | 8 $\mu$M |
| HSV-1 | 0.5 | 03 | 7.9E+08 | 9.0E+08 | 8.45E+08 | 11 $\mu$M |
| HSV-1 | 0.5 | 06 | 5.7E+08 | 7.0E+08 | 6.35E+08 | |
| HSV-1 | 0.5 | 07 | 7.0E+08 | 8.0E+08 | 7.50E+08 | |
| HSV-1 | 0.5 | 08 | 6.9E+08 | 8.9E+08 | 7.90E+08 | 15 $\mu$M |
| HSV-1 | 0.5 | 09 | 6.6E+08 | 8.1E+08 | 7.35E+08 | |
| HSV-1 | 0.5 | 35 | 4.0E+05 | 5.0E+05 | 4.50E+05 | |
| HSV-1 | 0.5 | 37 | 1.8E+06 | | 1.8E+06 | |
| HSV-1 | 0.5 | 38 | 3.2E+06 | 3.8E+06 | 3.50E+06 | |
| HSV-1 | 0.05 | none | 6.7E+08 | 8.6E+08 | 7.65E+08 | |
| HSV-1 | 0.05 | 03 | 7.8E+07 | 9.0E+07 | 8.40E+07 | 11 $\mu$M |
| HSV-1 | 0.05 | 06 | 7.6E+07 | 7.7E+07 | 7.65E+07 | |
| HSV-1 | 0.05 | 07 | 8.4E+07 | 8.4E+07 | 8.40E+07 | |
| HSV-1 | 0.05 | 08 | 6.5E+07 | 8.3E+07 | 7.40E+07 | 15 $\mu$M |
| HSV-1 | 0.05 | 09 | 3.8E+07 | 4.5E+07 | 4.15E+07 | |
| HSV-1 | 0.05 | 35 | 4.5E+04 | 4.8E+04 | 4.65E+04 | |
| HSV-1 | 0.05 | 37 | 9.5E+04 | 1.0E+05 | 9.95E+04 | |
| HSV-1 | 0.05 | 38 | 2.3E+04 | 2.7E+04 | 2.50E+04 | |
| HSV-2 | 0.5 | none | 5.3E+07 | 6.3E+07 | 5.80E+07 | |
| HSV-2 | 0.5 | 07 | 2.8E+07 | 3.0E+07 | 2.90E+07 | |
| HSV-2 | 0.5 | 38 | 6.5E+06 | 7.1E+06 | 6.80E+06 | |
| HSV-2 | 0.05 | none | 4.3E+07 | 4.3E+07 | 4.30E+07 | |
| HSV-2 | 0.05 | 07 | 1.6E+07 | 1.8E+07 | 1.70E+07 | |
| HSV-2 | 0.05 | 38 | 6.7E+04 | 8.0E+04 | 7.35E+04 | |

From the foregoing, it is readily apparent that substantial reductions in virus replication can result from the application of oligonucleotides in accordance with this invention.

Example 2

The following studies were designed to test the effectiveness of an antisense oligonucleotide complementary to the HSV-1 UL13 gone on ocular HSV infections in a murine model of HSV ocular disease.

Treatment Protocol

An anti-UL13 oligonucleotide, having the sequence GCCGAGGTCCATGTCGTACGC (ISIS 1082; SEQ ID NO.: 7), was dissolved in a buffer containing 50 am sodium acetate (pH 5.8) and 0.15 M NaCl for administration to 4 to 5 week old female BALB/c mice. Three different doses of ISIS 1082 were tested and treatment was begun 4 hours post-infection (pi) with a laboratory strain of HSV-1 which causes severe ocular infections. The strain HSV-1 KOS (Grau et al., *Invest. Ophthalmol. Vis. Sci.*, 30:2474–2480 (1989) was used throughout these studies at an inoculum of $1 \times 10^5$ plaque forming units (pfu).

To administer the test drug, mice were anesthetized with halothane (2.5%) inhalation. A 10 $\mu$l drop of solution was placed on the cornea and the eye held open for 15 seconds. The mice were then returned to their cages. Excess drug was not removed. Treatment was administered every 2 hours for 16 hours per day (8 doses total per day) during the first 7 days and every 4 hours for 16 hours per day (4 doses per day) during the second week of treatment.

Mice were held for 30 days pi. At that time, trigeminal ganglia (TG) were aseptically removed. One half of the samples were homogenized, frozen and thawed 3 times and titered for infectious virus as described in Brandt and Grau, *Invest. Ophthalmol. Vis. Sci.*, 31:2214–2223 (1990). All samples were placed in 600 $\mu$l of cell culture media prior to processing for the assay. Three mice were used for each group at each tin point. Titers are reported as the mean total $\log_{10}$ pfu per tissue.

The remaining samples were minced and placed in culture dishes containing monolayers of Vero cells in medium containing 2% serum. Co-cultures were monitored every other day for 2 weeks for evidence of cytopathic effect.

The Effect of Treatment on Ocular Disease

Three doses of ISIS 1082, buffer, and commercially available triflurothymidine (TFT) solution (1.0%, Viroptic, Burroughs-Wellcome) were tested. The various treatment groups are listed in Table 4.

TABLE 4

| Group | No. of Animals | Treatment |
|---|---|---|
| A | 10 | Buffer Only |
| B | 10 | 0.1% ISIS 1082 |
| C | 10 | 0.3% ISIS 1082 |
| D | 9 | 1.0% ISIS 1082 |
| E | 9 | Viroptic (1.0%) |
| F | 10 | Mock Infected |
| G | 10 | No Treatment |

FIG. 7 shows the results from scoring the mice for blepharitis, vascularization of the cornea, and stromal keratitis. Blepharitis was first visible on day 3 pi in groups A, B, C, D, and G, increased in severity, peaked on day 7, and then began to heal. The blepharitis scores on day 7 for groups A, B, C, D, and G were not significantly different (p>0.05) indicating that ISIS 1082 had little if any effect on the development of severe blepharitis. Blepharitis had healed completely by day 15 in groups C and D but took as long as 28 days in groups B and G, and did not heal completely in group D. The differences in disease scores between groups A, B, C, and D and G were significantly different on day 15 (p>0.05) indicating that treatment with ISIS 1082 reduced healing tie. TFT (group E) prevented the development of significant blepharitis.

To determine if ISIS 1082 caused inflammation, 10 nice were mock infected with a 1.0% solution of ISIS 1082. The drug was given every 2 hours (8 doses per day) for 7 days and blepharitis was scored daily. None of the mice developed any signs of blepharitis or inflammation. Therefore, the blepharitis seen in ISIS 1082 treated animal (FIG. 7) was not caused by the drug.

Vascularization of the cornea was first detected between days 5 and 7 and increased in severity in groups A, B, C, D, and G. Vascularization peaked on day 11 in untreated, infected mice (group G), declined slightly on day 13, but remained high even out to day 28 pi (score 1.2). Vascularization peaked on day 13 (score 1.7) and remained high in mice treated with buffer only. Mice treated with ISIS 1082 developed vascularization that peaked on day 13 and then remained constant out to day 28 pi regardless of the dose. However, the vascularization in the ISIS 1082 treated groups was less severe than untreated or buffer treated mice (scores of 0.8 to 1.2 vs 1.7, respectively, on day 13), indicating that although ISIS 1082 did not prevent vascularization, it did reduce the severity of the disease. A mild vascularization was observed on day 15 in mice treated with TFT (group F) but cleared quickly.

Mice in groups A, B. C, D, and G all developed stromal keratitis. Stromal keratitis was first detected on days 7 and 8, increased in severity, and peaked between days 11 and 15 in groups A and G. Stromal keratitis did not peak until day 15 or 21 in mice treated with ISIS 1082 and was less severe on days 11, 13, and 15 compared to untreated and buffer treated mice. Mice treated with TFT developed mild stromal keratitis on day 15 that cleared by day 21.

The time course data for days 11, 13, and 15 were analyzed for statistically significant differences by ANOVA at the 95%, 90%, and 85% confidence levels. The results are shown in Table 5.

similar disease scores. These difficulties in statistical inter-

TABLE 5

| | Stromal Keratitis | | | | | | | | Vascularization | | | | | | | | Blepharitis | | | | | | |
|---|---|---|---|---|---|---|---|---|---|---|---|---|---|---|---|---|---|---|---|---|---|---|---|
| | Day 11 | | | | | | | | Day 11 | | | | | | | | Day 11 | | | | | | |
| | A | B | C | D | E | F | G§ | | A | B | C | D | E | F | G | | A | B | C | D | E | F | G |
| A | – | 0 | + | + | * | * | 0 | A | – | 0 | 0 | 0 | * | * | 0 | A | – | 0 | 0 | 0 | * | * | 0 |
| B | | – | 0 | 0 | * | * | + | B | | – | 0 | 0 | * | * | + | B | | – | 0 | 0 | # | + | 0 |
| C | | | – | 0 | # | # | * | C | | | – | 0 | * | * | 0 | C | | | – | 0 | 0 | 0 | + |
| D | | | | – | # | + | * | D | | | | – | * | * | 0 | D | | | | – | + | * | 0 |
| E | | | | | – | 0 | * | E | | | | | – | 0 | * | E | | | | | – | 0 | * |
| F | | | | | | – | * | F | | | | | | – | * | F | | | | | | – | * |
| G | | | | | | | – | G | | | | | | | – | G | | | | | | | – |
| | Day 13 | | | | | | | | Day 13 | | | | | | | | Day 13 | | | | | | |
| | A | B | C | D | E | F | G | | A | B | C | D | E | F | G | | A | B | C | D | E | F | G |
| A | – | 0 | + | 0 | * | * | 0 | A | – | 0 | + | # | * | * | 0 | A | – | 0 | # | + | * | * | 0 |
| B | | – | 0 | 0 | * | * | 0 | B | | – | 0 | # | * | * | 0 | B | | – | 0 | 0 | + | * | 0 |
| C | | | – | 0 | 0 | 0 | * | C | | | – | 0 | # | + | * | C | | | – | 0 | 0 | 0 | # |
| D | | | | – | 0 | # | * | D | | | | – | + | * | + | D | | | | – | 0 | 0 | + |
| E | | | | | – | 0 | * | E | | | | | – | 0 | * | E | | | | | – | 0 | * |
| F | | | | | | – | * | F | | | | | | – | * | F | | | | | | – | * |
| G | | | | | | | – | G | | | | | | | – | G | | | | | | | – |
| | Day 15 | | | | | | | | Day 15 | | | | | | | | Day 15 | | | | | | |
| | A | B | C | D | E | F | G | | A | B | C | D | E | F | G | | A | B | C | D | E | F | G |
| A | – | 0 | * | 0 | * | * | 0 | A | – | 0 | * | 0 | * | * | 0 | A | – | 0 | * | * | * | * | 0 |
| B | | – | # | 0 | * | * | 0 | B | | – | 0 | 0 | * | * | 0 | B | | – | * | * | * | * | 0 |
| C | | | – | 0 | 0 | 0 | * | C | | | – | 0 | 0 | # | * | C | | | – | 0 | 0 | 0 | + |
| D | | | | – | + | * | 0 | D | | | | – | # | * | 0 | D | | | | – | 0 | 0 | # |
| E | | | | | – | 0 | * | E | | | | | – | 0 | * | E | | | | | – | 0 | # |
| F | | | | | | – | * | F | | | | | | – | * | F | | | | | | – | + |
| G | | | | | | | – | G | | | | | | | – | G | | | | | | | – |

* = 95% confidence
+ = 90% confidence
# = 85% confidence

This analysis shows that 0.3% and 1.0% ISIS 1082 solutions significantly reduced the severity of stromal keratitis and vascularization of the cornea on days 11, 13, and 15 compared to the untreated and buffer treated mice. In some instances, a disease score will be significantly different on one day but not on another. It was also found that groups that should have been significantly different were not. For example, stromal keratitis scores for 0.3% ISIS 1082 treated nice were significantly different from buffer treated mice on day 15 but the 1.0% ISIS 1082 treated nice were not significantly different even though the two groups have pretation of the data are caused by variability in disease scores, which is normal in these types of studies, and the sample size.

The Effect of Treatment on In Vivo Replication

Mice were infected with $1 \times 10^5$ pfu of HSV-1 KOS and on days 1, 2, 3, 6, 8, and 10 post-infection, the eyes, TG, and eyelids were removed and the amount of infectious virus measured, as described above. The results are shown in Table 6.

TABLE 6

| | | Day | | | | | |
|---|---|---|---|---|---|---|---|
| Group | Treatment | 1 | 2 | 3 | 6 | 8 | 10 |
| | | Eye Titers+ | | | | | |
| A | Buffer | 4.36(3/3)* | 4.47(3/3) | 2.45(3/3) | 2.65(3/3) | 0(0/3) | 0(0/2) |
| B | 0.1% IS-1082 | 4.13(3/3) | 3.04(3/3) | 3.94(2/3) | 2.58(2/3) | 1.98(2/2) | 0(0/2) |
| C | 0.3% IS-1082 | 4.38(3/3) | 4.27(1/3) | 3.37(3/3) | 2.48(2/3) | 0(0/3) | 0(0/2) |
| D | 1.0% IS-1082 | 3.36(2/2) | 4.19(3/3) | 2.43(1/2) | 3.11(2/3) | 2.59(1/2) | 0(0/2) |
| E | 1.0% TFT | 3.04(3/3) | 2.98(2/3) | 0(0/3) | 0(/3) | 0(0/3) | 0(0/2) |
| G | None | 4.06(3/3) | 4.27(3/3) | 3.64(2/3) | 2.60(3/3) | 0(0/3) | 0(0/2) |
| | | Eyelid Titers+ | | | | | |
| A | Buffer | 2.71(1/3) | 2.06(1/3) | 3.56(1/3) | 1.96(2/3) | 2.16(1/3) | 0(0/2) |
| B | 0.1% IS-1082 | 0(0/3) | 0(0/3) | 1.83(1/3) | 0(0/3) | 0.78(1/3) | 0(0/2) |
| C | 0.3% IS-1082 | 0(0/3) | 0(0/3) | 3.92(2/2) | 3.42(2/3) | 2.20(2/3) | 0(0/2) |
| D | 1.0% IS-1082 | 0(0/3) | 2.13(2/3) | 3.45(1/3) | 2.70(1/3) | 0(0/2) | 0(0/2) |
| E | 1.0% TFT | 0(0/3) | 0(0/3) | 0(0/2) | 0(0/3) | 0(0/2) | 0(0/2) |
| G | None | 0(0/3) | 2.43(1/2) | 0.78(1/2) | 0.60(1/3) | 0(0/2) | 0(0/2) |

TABLE 6-continued

| Group | Treatment | 1 | 2 | 3 | 6 | 8 | 10 |
|---|---|---|---|---|---|---|---|
| | | Trigeminal Ganglia Titers+ | | | | | |
| A | Buffer | 0(0/3) | 0(0/2) | 2.18(2/2) | 3.71(3/3) | 1.75(2/3) | 0(0/1) |
| B | 0.1% IS-1082 | 0(0/3) | 0(0/3) | 0(0/3) | 3.29(3/3) | 2.66(3/3) | 0(0/2) |
| C | 0.3% IS-1082 | 0(0/3) | 0(0/3) | 3.26(1/2) | 0.30(1/3) | 2.32(2/3) | 0(0/2) |
| D | 1.0% IS-1082 | 0(0/3) | 0(0/3) | 0(0/3) | 2.88(2/3) | 0(0/2) | 0(0/2) |
| E | 1.0% TFT | 0(0/3) | 0(0/3) | 0(0/3) | 0.30(1/3) | 0(0/3) | 0(0/2) |
| G | None | 0(0/3) | 0(0/3) | 2.58(1/3) | 3.89(3/3) | 2.78(2/3) | 0(0/2) |

+$Log_{10}$ of mean total pfu for 3 mice per day
*No. positive/no. tested

Dose Response to ISIS 1082

Figure 9:
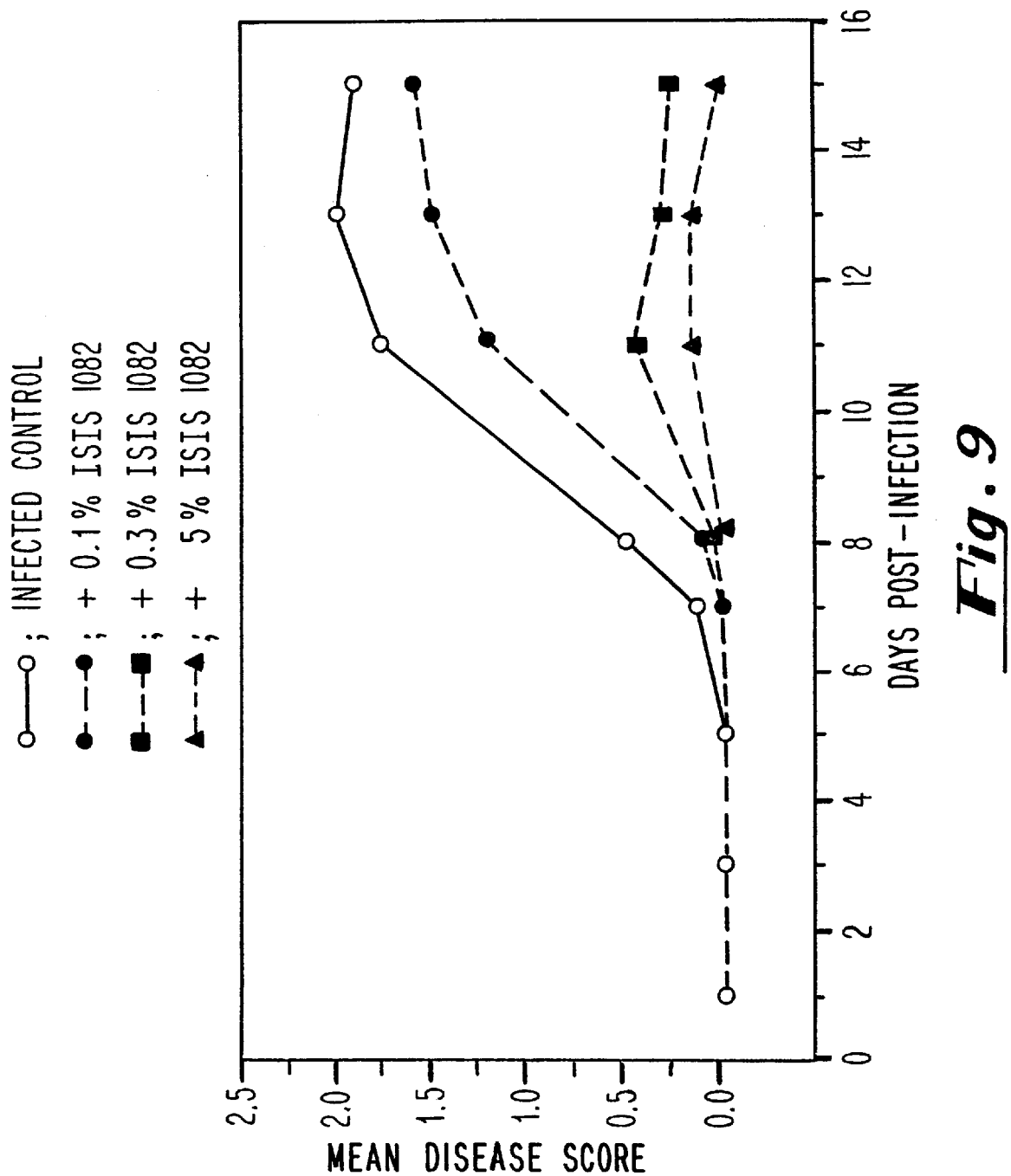
FIG. 9 is a graphical depiction showing mean disease scores at various times after infection. Mice were infected with $1\times10^5$ pfu of HSV-1, strain KOS, and treatment with ISIS 1082 was begun 4 hours pi. Each data point represents the mean disease scores of all mice in the group on a given day.

The results presented in FIG. 7 indicate that there was some effect of drug dose on ocular disease. FIG. 8 shows drug dose vs disease scores for blepharitis, vascularization, and stromal keratitis on days 11, 13, and 15 pi. In general, disease severity decreased at doses of 0.3% and 1.0% ISIS 1082. The high dose of ISIS 1082 (1.0%) did not appear to be more effective than the lower dose (0.3%). The antiviral effect of a 5.0% solution of ISIS 1082 compared to the lower concentrations versus HSV-1, strain KOS, in the murine ocular model of stromal keratitis is summarized in FIG. 9. As shown, treatment with a 5.0% solution of ISIS 1082 gave significant improvement in mean disease scores of stromal keratitis at day 11 pi. The reduction in disease with a 5.0% solution was greater than the reduction with a 0.3% solution, which in turn was greater than the reduction with a 0.1% solution. These dose dependent efficacy curves are similar to the effects observed in earlier experiments, which were summarized in FIGS. 7 and 8.

Establishment of Latency

The effect of drug treatments on latency was also determined. TG were removed at 28 days pi. One half of the tissues were assayed directly for infectious virus and the remaining samples were assayed by co-cultivation on Vero cells for reactivatable latent infection. None of the tissues were positive when titered directly for virus. As shown in Table 7, none of the TG from mice treated with 1.0% TFT were positive for reactivatable virus. Reactivatable virus was detected in TG from mice in all other treatment groups. By day 14 of co-cultivation, between 60 and 100% of the samples were positive.

TABLE 7

| | | | Reactivation | |
|---|---|---|---|---|
| Group | Virus | Treatment | Day 7 | Day 14 |
| A | + | Buffer | 3/5‡ (60)§ | 3/5 (60) |
| C | + | 0.3% IS-1082 | 3/5 (60) | 5/5 (100) |
| D | + | 1.0% IS-1082 | 3/5 (60) | 4/5 (80) |
| E | + | TFT | 0/5 (0) | 0/5 (0) |
| F | − | None | ND* — | ND* — |
| G | + | None | 3/5 (60) | 4/5 (80) |

Days after establishment of co-cultures
‡No. positive/no. tested
*Not done
§% of sample positive Example 3
Effect of Various Oligonucleotides Upon HSV Yield The effect of various oligonucleotides upon the replication of HSV was examined using an infectious yield assay, as generally described in Example 1.

HSV-1 strains PAAr[5] and DM.2.1 were obtained from Burroughs Wellcome Company.

Plasmids used for the in vitro synthesis of HSV-1 and HSV-2 UL13 RNAs were constructed by cloning relevant pieces of the HSV genes into the KpnI and BamHI restriction endonuclease sites in the polylinker region of the transcription vector pSP72 (Promega Corporation). The insertion in plasmid pIP-1 consists of a 3245 nucleotide KpnI-BglII fragment of HSV-1 DNA which was taken from plasmid p1B01 (kindly supplied by S. Weller, University of Connecticut Health Center, Farmington, Conn.) containing the HSV-1 BglII fragment 0 DNA. The KpnI-BglII fragment contains coding sequences which begin at nucleotide +68 within the 5', nontranslated portion of the HSV-1 UL13 mRNA, traverse the entire open reading frame encoding the UL13 protein and end at nucleotide +3313 within the UL13 mRNA. The insertion in plasmid pIP-2 consists of a 1684 nucleotide KpnI-Bam HI fragment of HSV-2 DNA which was taken from plasmid BEDJ (kindly supplied by E. Wagner, University of California, Irvine, Calif.) containing the coding region of the HSV-2 homolog to the UL13 gene. The KpnI-BamHI fragment contains coding sequences which begin at nucleotide +68 within the 5', nontranslated portion of the HSV-2 mRNA, traverse through the entire open reading frame encoding the UL13 protein and end at nucleotide +1752 within the UL13 mRNA. The HSV DNA inserts in plasmids pIP-1 and pIP-2 are oriented so that transcription from the T7 promoter contained within the plasmids will give viral sense-strand transcripts.

Transcription reagents were obtained from Promega Corporation and protocols were performed as recommended by the manufacturer. To produce pIP-1 and pIP-2 RNAs encoding the HSV-1 and HSV-2 UL13 reading frames, respectively, plasmids pIP-1 and pIP-2 were linearized by digestion with restriction enzyme XbaI, which cuts the DNAs at a unique site 3' of the HSV DNA sequences which were cloned into pSP72. These linearized plasmids were used as template for in vitro transcription with T7 RNA polymerase. in vitro transcripts were purified by digestion of the template DNA with RQ1 DNase (20 minutes, 37° C.), two extractions with phenol:chloroform: isoamyl alcohol (25:24:1), extraction with chloroform isoamyl alcohol (24:1), precipitation in 3.75 M ammonium acetate and 70% ethanol, and resuspension in diethyl pyrocarbonate (DEPC)-treated water. The integrity and purity of the RNA preparations wore verified by electrophoresis of an aliquot on a denaturing formaldehyde agarose gel according to standard procedures.

In vitro translation reagents were purchased from Promega Corporation. Translation reactions contained 120 ng of an appropriate RNA sample, 4 μl of rabbit reticulocyte lysate, 1 μl of a methionine-free amino acid mixture, 1 μl of [$^{35}$S] methionine (5 μCi, >1000 Ci/mmol, New England Nuclear), in a total volume of 12 μl. The translation mixture was incubated for 1 hour at 37° C. After translation, 12 μl of the translation mixture was added to 12 μl of 2×Laemmli Loading Buffer (1×=88 Tris-HCl, pH 6.8; 2% sodium dodecyl sulphate [SDS]; 5.0% β-mercaptoethanol; 10% glycerol; and 0.001% bromphenol blue), heated in a boiling water bath for 10 minutes, and the in vitro translation products were resolved by electrophoresis in a 10% polyacrylamide-SDS (Laemmli) gel. The resultant gels were dried under vacuum and autoradiography was performed using Kodak XRP-5 film. The RNA samples used for in vitro translation were preincubated for 1 hour at 37° C., with or without added oligonucleotide, immediately prior to addition into the translation mixture calls were overlaid with 1.5 ml of fresh medium, containing either ISIS 1082 or Acyclovir where appropriate, and incubated 3 days at 37° C. After the drug treatment, cells were overlaid with fresh medium and incubated for 6 days at 37° C. prior to fixation and staining with crystal violet. To determine the toxic effect of compound upon the HeLa cells, stained cells were counted and compared to cell counts from parallel cultures of untreated HeLa cells.

The antiviral activity of various oligonucleotides containing different nucleotide sequences and backbone compositions were compared to the inhibitory activity of ISIS 1043 which has been shown to have anti-HSV activity in vitro. The oligodeoxyribonucleotide sequences, their target mRNA regions and the backbone composition of the oligonucleotides tested are listed in Table 8.

TABLE 8

| Oligo Number | Backbone | Seauence | (SEQ ID NO.:) | Target | Gene | Location |
|---|---|---|---|---|---|---|
| 1043 | P=O | GTCCGCGTCCATGTCGGC | 1 | HSV-1 | UL48 | AUG[a] |
| 1044 | P=O | GGACTCATCCATCCTTCGGCC | 2 | HSV-1 | UL13 | AUG-1[b] |
| 1045 | P=O | GCGGCTGGCCATTTCAACAGA | 3 | HSV-1 | UL39 | AUG |
| 1046 | P=O | CGCGGAATCCATGGCAGCAGG | 4 | HSV-1 | UL40 | AUG |
| 1047 | P=O | ACCGAGGTCCATGTCGTACGC | 5 | HSV-1 | UL13 | AUG-2 |
| 1048 | P=O | GGACTCATCCATCCGTCCGCC | 6 | HSV-2 | UL13 | AUG-1 |
| 1049 | P=O | GCCGAGGTCCATGTCGTACGC | 7 | HSV-2 | UL13 | AUG-2 |
| 1076 | P=S | GGACTCATCCATCCTTCGGCC | 2 | HSV-1 | UL13 | AUG-1[b] |
| 1077 | P=S | GCGGCTGGCCATTTCAACAGA | 3 | HSV-1 | UL39 | AUG |
| 1078 | P=S | CGCGGAATCCATGGCAGCAGG | 4 | HSV-1 | UL40 | AUG |
| 1080 | P=S | ACCGAGGTCCATGTCGTACGC | 5 | HSV-1 | UL13 | AUG-2 |
| 1081 | P=S | GGACTCATCCATCCGTCCGCC | 6 | HSV-2 | UL13 | AUG-1 |
| 1082 | P=S | GCCGAGGTCCATGTCGTACGC | 7 | HSV-2 | UL13 | AUG-2 |

[a]Draper et al., Antiviral Res. 13: 151–164 (1990)
[b]UL13 AUG-1 is the primary translation initiation codon in the UL13 mRNA. UL13 AUG-2 is a second translation initiation codon which directs a low level of translational activity from the UL13 mRNA in in vitro translations.

Oligonucleotides were synthesized on an automated DNA synthesizer (Applied Biosystems model 380B) using standard phosphoramidite chemistry as described in Example 1. For the phosphorothioate oligonucleotides, sulfurization was performed after each coupling using 0.2 M $^3$H-1,2-Benzodithiol-3-one-1,1-dioxide dissolved in acetonitrile as described by Beaucage et al., Ann. N.Y. Acad. Sc. (1989). To insure complete thioation, the growing oligonucleotide was capped after each sulfurization step. For the methylphosponate oligonucleotides, methyl phosphoramidite bases were obtained from Glen Research Corporation. All oligonucleotides were purified by lyophilization and two ethanol precipitations prior to us*. The purity and integrity of the oligonucleotide preparation was determined by acrylamide gel electrophoresis.

Figure 10:
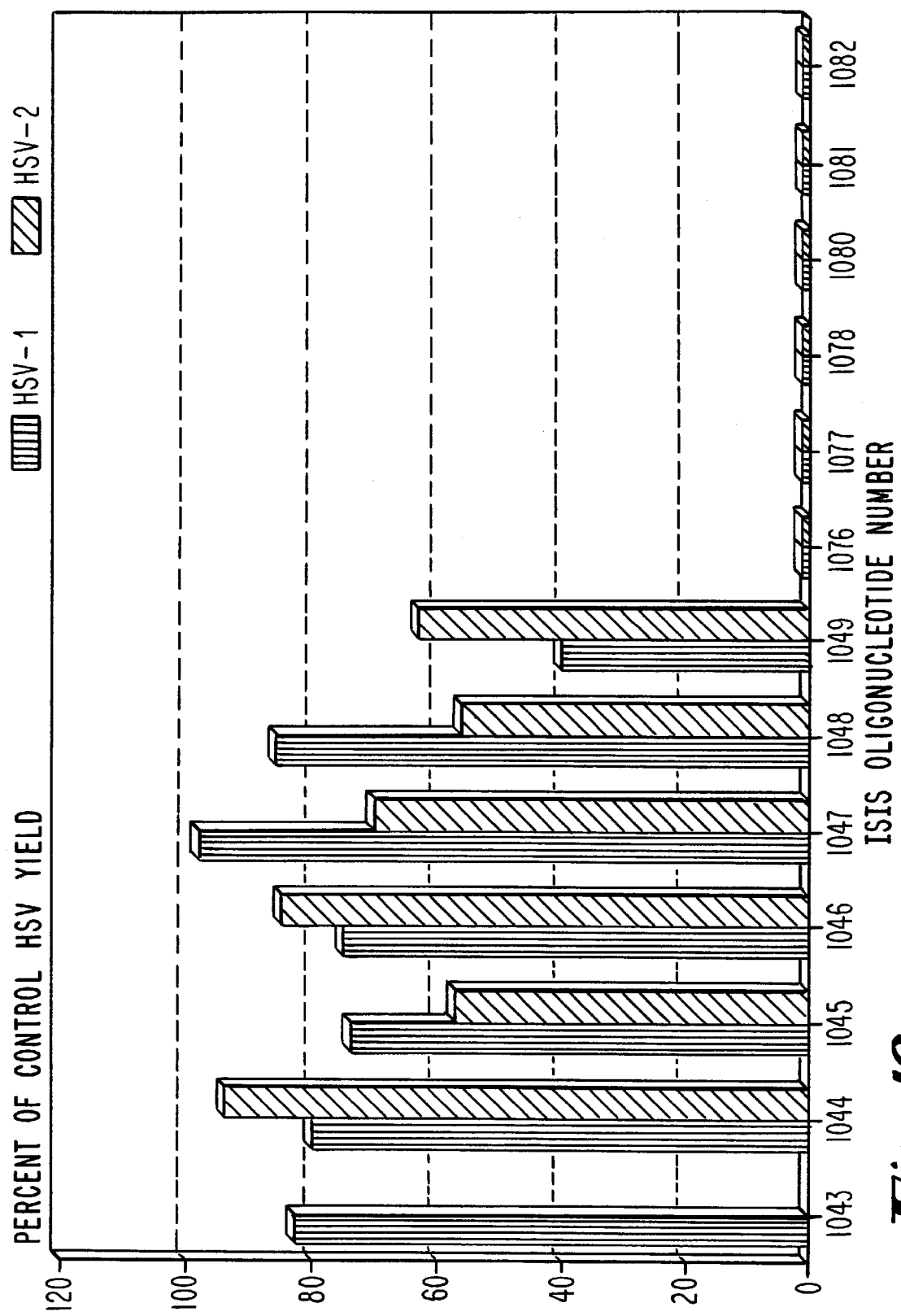
FIG. 10 is a graph showing the effect of various ISIS oligonucleotides upon HSV infectious yield. HSV-1 (strain KOS) and HSV-2 (strain HG52) were used. The control yield of HSV in these experiments was $8.1\times10^7$ pfu/ml and $8.2\times10^7$ pfu/ml for HSV-1 and HSV-2, respectively.

For each experimental point in the clonogenic assay, HeLa cells (2500 cells in 5 ml of DNEM-10% FCS) were seeded in triplicate into 60 mm$^2$ tissue culture plates and incubated 18 hours at 37° C. After the overnight incubation, A viral multiplicity of 0.5 pfu/cell was used for these activity screens. A representative comparison of antiviral activities versus HSV-1 and HSV-2 is shown in FIG. 10. Comparison of the antiviral effects of oligonucleotides with P=O backbones showed that the reduction of HSV infectious yield depended upon both the subtype of HSV used and the sequence of the oligonucleotide. The broadest antiviral activity was observed using ISIS 1049. Surprisingly, ISIS 1047, whose nucleotide sequence differs from ISIS 1049 only at the 5' terminal base, was not as effective as ISIS 1049 in inhibiting infectious virus yields. Although the trends of inhibition observed with the P=O oligonucleotides were consistent in all experiments, the absolute levels of inhibitory activity varied considerably (i.e., ISIS 1049 was invariably the best inhibitor of HSV replication, but the levels of inhibition ranged from a low of 18% to a high of 63% in 5 experiments). It was found that this variability was primarily due to differences in the temperature at which the fetal calf serum (FCS) was heat inactivated. The levels of inhibition shown in FIG. 10 were obtained using FCS which had been heat-treated at 65° C. This treatment of the serum was standardized for all subsequent experiments.

Conversion of the oligonucleotide backbone from the P=O structure to the P=S structure resulted in greatly enhanced anti-HSV activity of all novel oligonucleotides tested (FIG. 10). in contrast to the serum effects observed with P=O oligonucleotides and consistent with the increased resistance of P=S oligonucleotides to digestion by serum nucleases, it was found that the inhibitory activity of P=S oligonucleotides was independent of changes in the temperature of FCS heat-treatment.

Effect of Viral Multiplicity Upon ISIS 1082 Inhibition of HSV-1 Replication.

The effect of initial viral burden upon the antiviral activity of ISIS 1082 was examined using an infectious yield assay. Cells were infected at an MOI of either 0.05, 0.1, 0.25, 0.5, 1.0 or 2.5 pfu/cell, in the presence and absence of 4 uM concentrations of ISIS 1082. ISIS 1082 was chosen for this experiment because of the broad anti-HSV activity of its analog, ISIS 1049, and the increased nuclease-resistance associated with P=S oligonucleotides. Infection of HeLa cells with HSV-1 across this range of multiplicities resulted in only a threefold increase of infectious virus production between the lowest MOI (0.05 pfu/cell) and the highest MOI (2.5 pfu/cell), while the range of multiplicities increased by 50-fold (Table 9).

of 1.0 pfu/cell, to the highest level of inhibition (99.5%) at a MOI of 0.1 pfu/cell. Thus, when using MOIs between 0.1 and 1.0 pfu/cell, the amount of infectious virus produced did not reflect a simple mathematical relationship to the amount of input virus. However, the antiviral effect of ISIS 1082 was related inversely to the amount of input virus across this range of MOIs.

Effect of Backbone Composition Upon Antiviral Activity of Oligonucleotides

The effect of backbone composition upon the antiviral activity of oligonucleotides was examined by comparing different analogs of three oligonucleotide sequences in parallel assays. The nucleotide sequence of ISIS 1047 and a shortened version of this sequence, found in ISIS 1301, were synthesized with P=O, P=S and MeP backbones. The antiviral activities of these oligonucleotides in an infectious yield assay were compared to those of the MeP oligonucleotide described by Kulka et al., 1989. *Proc. Natl. Acad. Sci. USA* 86:6868–6872 and its P=S analog (Table 10).

TABLE 10

| (SEQ ID NO.:) | Sequence | Oligo | Backbone Linkage | % Control Yield HSV-1[a] | HSV-2[b] |
|---|---|---|---|---|---|
| 5 | ACCGAGGTCCATGTCGTACGC | 1047 | P=O | 105[c] | 107 |
|   |   | 1237 | MeP | 29.8 | 34.1 |
|   |   | 1080 | P=S | 0.4 | 2.5 |
| 9 | GAGGTCCATGTCGTA | 1301 | P=O | 63.1 | 95.5 |
|   |   | 1277 | MeP | 50.8 | 34.1 |
|   |   | 1302 | P=S | 1.4 | 10.9 |
| 10 | TTCCTCCTGCGG[d] | 1236 | MeP | 35.1 | 40.9 |
|   |   | 1235 | P=S | 108 | 105 |

[a]HSV-1 (strain KOS) used at input MOI = 0.5 pfu/cell.
[b]HSV-2 (strain HG52) used at input MOI = 0.5 pfu/cell.
[c]All oligonucleotides were applied at a concentration of 4 μM. The values used to determine percent control yield were achieved by calculating the average of duplicate titrations from a pooled sample of 2–3 experiments. All oligonucleotides gave >99% inhibition at concentrations of 100 μM.
[d]The methylphosphonate analog of this oligonucleotide sequence was previously reported to exhibit anti-HSV activity in a plaque reduction assay.

TABLE 9

| Input MOI[a] (pfu/cell) | ISIS 1082 | Virus Yield (pfu/ml) | % Control Yield |
|---|---|---|---|
| 2.5 | − | $58.5 \pm 5.5 \times 10^7$ |   |
|   | + | $56.5 \pm 6.0 \times 10^6$ | 9.7 |
| 1.0 | − | $46.0 \pm 4.0 \times 10^7$ |   |
|   | + | $44.5 \pm 0.5 \times 10^6$ | 9.7 |
| 0.5 | − | $42.0 \pm 7.0 \times 10^7$ |   |
|   | + | $71.0 \pm 3.0 \times 10^5$ | 1.7 |
| 0.25 | − | $35.0 \pm 3.0 \times 10^7$ |   |
|   | + | $11.1 \pm 0.5 \times 10^6$ | 3.2 |
| 0.1 | − | $35.0 \pm 1.0 \times 10^7$ |   |
|   | + | $18.5 \pm 3.5 \times 10^5$ | 0.5 |
| 0.05 | − | $19.5 \pm 0.5 \times 10^7$ |   |
|   | + | $15.5 \pm 3.5 \times 10^5$ | 0.8 |

[a]HSV-1 (strain KOS) was used for these experiments.

Over this same range of multiplicities, the antiviral effect of ISIS 1082 varied from a low inhibition of 90.3% at a MOI At oligonucleotide concentrations of either 4 μM or 100 μM, the degree of inhibition of HSV-1 progenesis was roughly equivalent for each of the nethylphosphonate oligonucleotide (ISIS 1237, 1277 and 1236). At an oligonucleotide concentration of 4 μm, the anti-HSV activities shown by the MeP oligonucleotides were similar with both subtypes of HSV tested. For ISIS 1237 and 1277, the antiviral activities of the MeP analogs were better than those observed with the corresponding P=O analogs, ISIS 1047 and 1301, respectively. Phosphorothioate analogs of the 21- and 15-nucleotide sequences (ISIS 1080 and ISIS 1302, respectively), exhibited greatly enhanced antiviral activity over that observed when using either ISIS 1237 or ISIS 1277. Surprisingly, neither HSV-1 nor HSV-2 replication was inhibited by ISIS 1235, the P=S analog of ISIS 1236. Comparatively, the level of antiviral activity was affected more profoundly by changes in composition of the oligonucleotide backbone or nucleotide sequence than by differences in the length of the oligonucleotide.

Effect of ISIS 1049 and 1082 Upon In Vitro Translation of UL13RNA

The ability of ISIS 1049 and 1082 oligonucleotides to bind specifically to target UL13 RNA (pIP-1 or pIP-2 transcript) and inhibit translation was examined using rabbit reticulocyte lysates for in vitro translations. ISIS 1238, which consists of a scrambled version of the ISIS 1080 nucleotide sequence, was included as a control for nonspecific phosphorothioate oligonucleotide effects upon translational activity. An in vitro synthesized transcript (5LO) containing the RNA sequence of the human 5-lipoxygenase transcript was used to determine the effect of the ISIS oligonucleotides upon translation of heterologous RNAs.

Translation of pIP-1 RNA (FIG. 11A) resulted in the synthesis of a major polypeptide product of approximately 61 kD mass and a number of lesser products, most notably a polypeptide of 33 kD mass which is initiated from the secondary AUG codon region complementary to the ISIS 1080 (1082) and 1047 (1049) oligonucleotides. Quantitatively, ISIS 1049 was a better inhibitor of the translation of pIP-1 RNA than ISIS 1082, which in turn was a better inhibitor than ISIS 1238. Qualitatively, the inhibition of pIP-1 RNA translation by ISIS 1049 and 1082 appears to be operating by slightly different molecular mechanisms. With both ISIS 1082 and 1049, the addition of oligonucleotide results in a reduction of the quantity of full length polypeptide synthesized from pIP-1 RNA. Additionally, inhibition with ISIS 1049 results in observable increases of three smaller polypeptide products of 33, 28, and 26 kD mass. The 33 kD polypeptide is the same polypeptide which is synthesized at low levels in the non-treated samples. The 28 kD polypeptide is believed to be a truncated version of the 61 kD and the 26 kD polypeptide is believed to be initiated at another in-phase AUG which is located 3' to the ISIS 1049 target region. Similar patterns of inhibition were observed when both the homologous in vitro transcript from pIP-2 (FIG. 11B) was substituted for pIP-1 RNA in the hybridization mixture and when translations were performed using wheat germ lysates.

Nonspecific inhibitory effects of oligonucleotides upon the translation of RNA were minimal. ISIS 1238 exhibited a slight, but detectable inhibition of the translation of pIP-1 RNA, while none of the oligonucleotides were inhibitory to the translation of the heterologous 5LO RNA.

Figure 12:
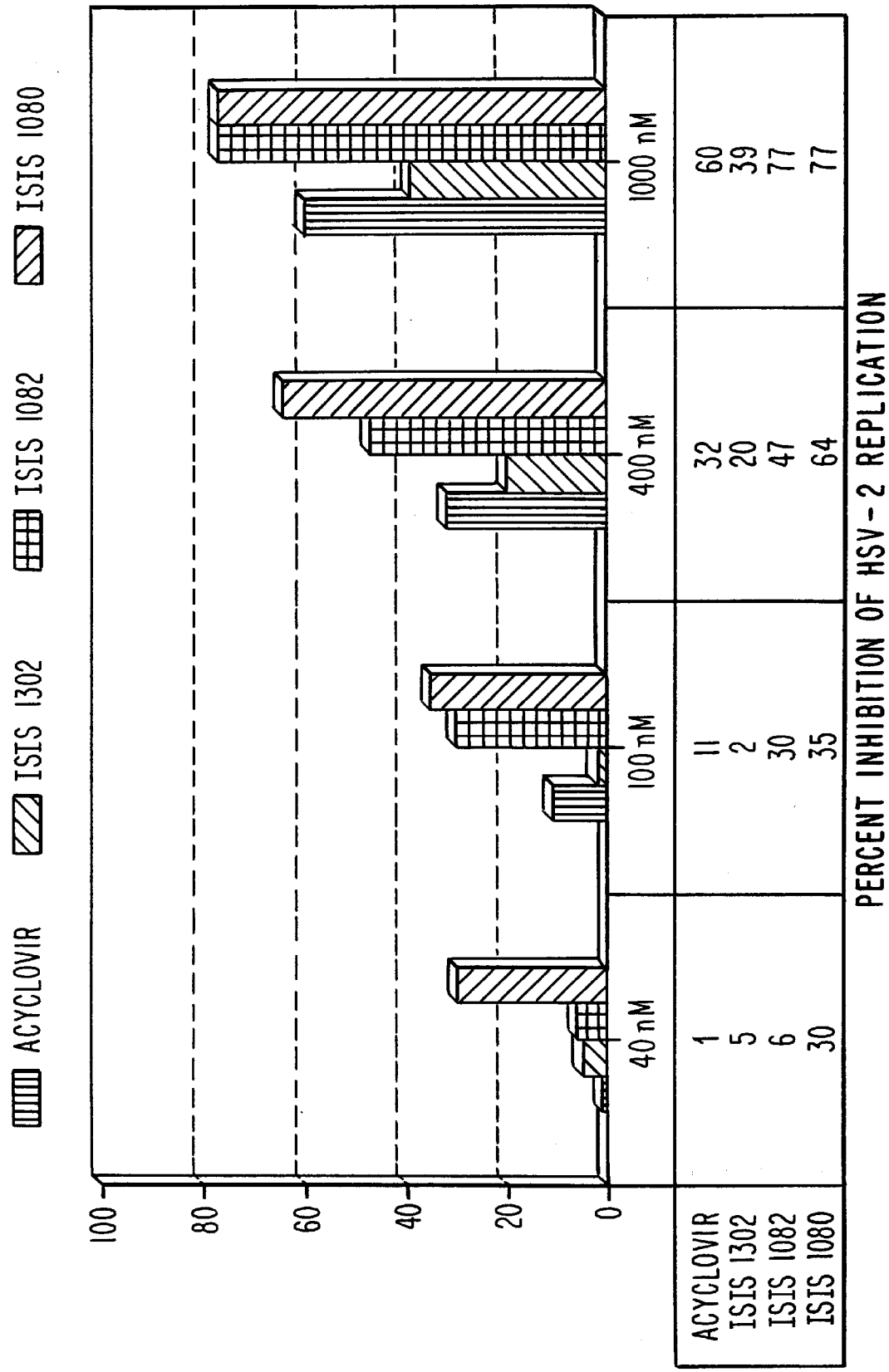
FIG. 12 depicts dose response curves showing inhibition of HSV-2 replication by treatment with various concentrations of ISIS oligonucleotides or Acyclovir. HSV-2 (strain HG52) was used in these infections. Control infections for the ACV-treated wells were adjusted in DMSO content to correspond to the level of DMSO present in cells treated with 1 $\mu$M concentrations of ACV.
Figure 13:
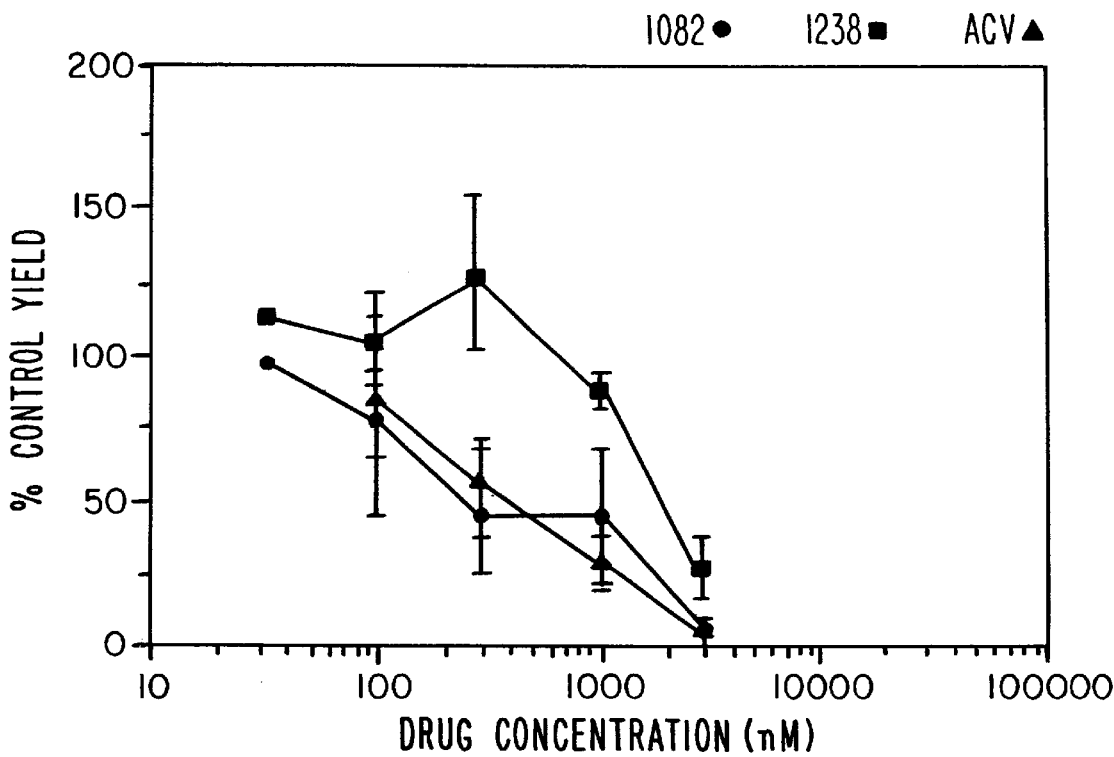
FIG. 13 illustrates the dose-dependent inhibition of HSV-1 (strain KOS) by ISIS 1082, ACV or ISIS 1238 treatment. Error bars represent the standard deviation (p>0.05) of the mean value for each concentration of compound.

Comparative Antiviral Effects of Acyclovir and ISIS Oligonucleotides Upon HSV-2 Replication Dose response curves for Acyclovir (ACV), ISIS 1302, ISIS 1080, and ISIS 1082 versus HSV-2 (strain HG52) were determined using the infectious yield assay. Because the ACV stock solutions (4 mM) were dissolved in dimethyl sulfoxide (DXSO), virus titers of the ACV-treated samples were compared to titers from control infections which were treated with 0.025% DMSO. The control virus yield calculated for DMSO-treated samples was approximately 30% greater than the yield observed in untreated samples. Representative dose response curves are shown in FIG. 13. Each of the four compounds affected HSV-2 replication in a dose-dependent manner. From the data shown in FIG. 12, the $IC_{50}$ values for these compounds were calculated to be 600 mM, 2 uM, 430 nM and 250 nM, respectively, for ACV, ISIS 1302, ISIS 1082 and ISIS 1080. The slopes of the dose response curves for ISIS 1080 and 1082 changed when other strains of HSV-1 or HSV-2 were used in the infection (e.g., see FIG. 12).

Dose Dependent Effect of ISIS 1082 Upon Replication of Two Strains of HSV-1

Figure 14:
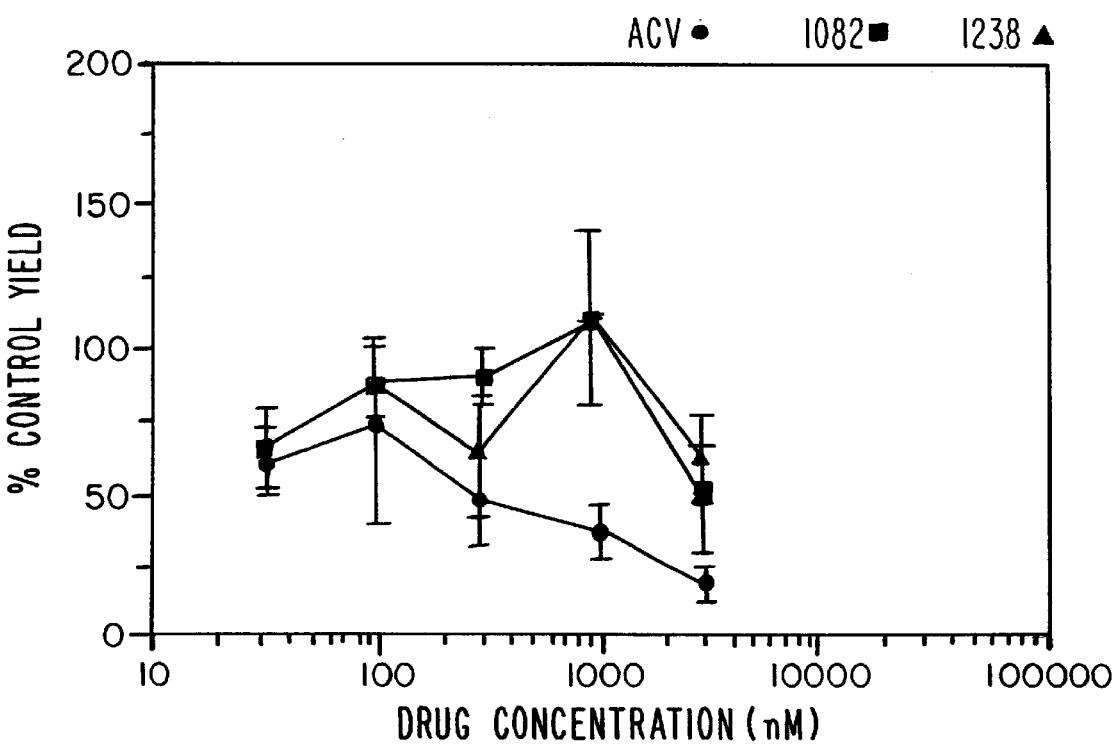
FIG. 14 illustrates the dose-dependent inhibition of HSV-1 (strain F) by ISIS 1082, ACV or ISIS 1238 treatment. Error bars represent the standard deviation (p>0.05) of the mean value for each concentration of compound.

The antiviral efficacy of ISIS 1082 versus two strains of HSV-1, KOS and F, was compared to the antiviral efficacy of both a known anti-HSV compound, ACV, and a non-complementary phosphorothioate oligonucleotide, ISIS 1238; this oligonucleotide comprises a scrambled version of ISIS 1080, serving as a control for nonspecific oligonucleotide effects on translational activity. ISIS 1238 was much less inhibitory than either ISIS 1082 or ACV in these studies. ISIS 1082 and ACV inhibited the KOS strain with predicted $IC_{90}$s of 2.73 and 2.57 $\mu$M, respectively (FIG. 13). The $IC_{90}$s of ACV and ISIS 1082 were extrapolated to be 3.6 and 5.8 $\mu$M, respectively for the F strain of the virus (FIG. 14). Although the $IC_{90}$ values of ACV and ISIS 1082 are similar for both virus strains, the dose response curves show that strain-specific patterns of inhibition exist among HSV strains treated with these compounds.

Dose Dependent Effect of ISIS 1082 Upon Replication of ACV-Resistant Strains of HSV-1

Figure 15A:
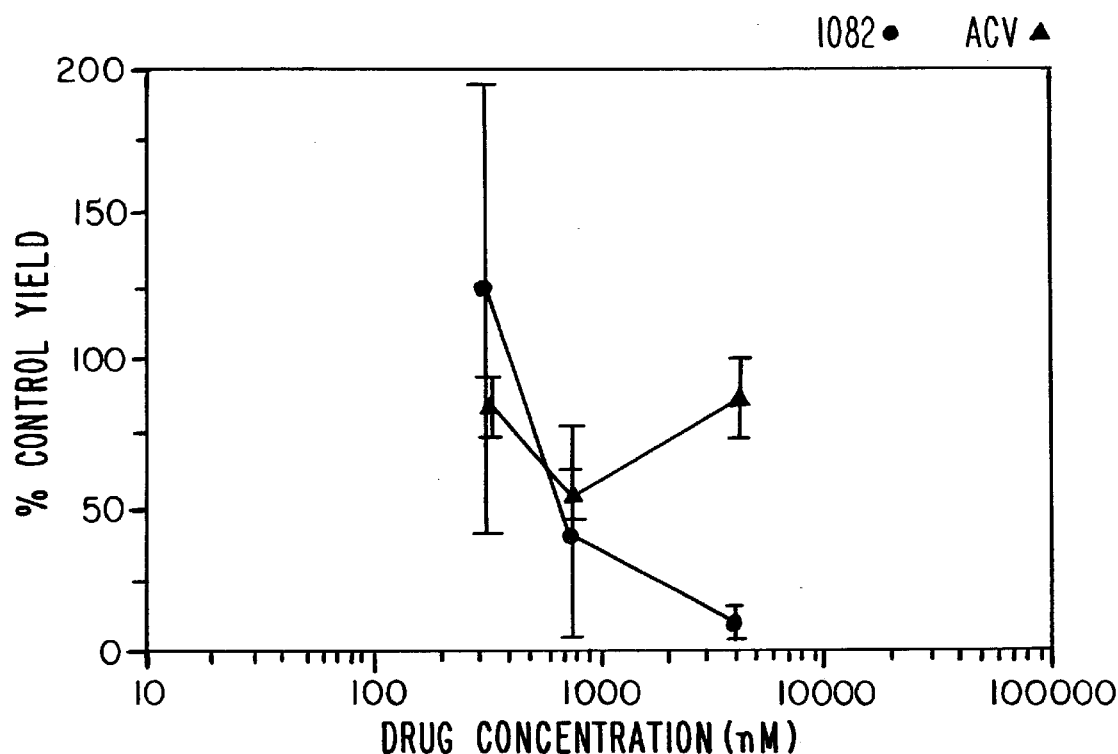
FIGS. 15A–15B show a dose dependent inhibition of HSV-1 strains by Acyclovir or ISIS 1082 treatment. Strains DM2.1 (FIG. 15B) and PAAr$^5$ (PAAr5) (FIG. 15A) were used. Control wells did not contain DMSO.
Figure 15B:
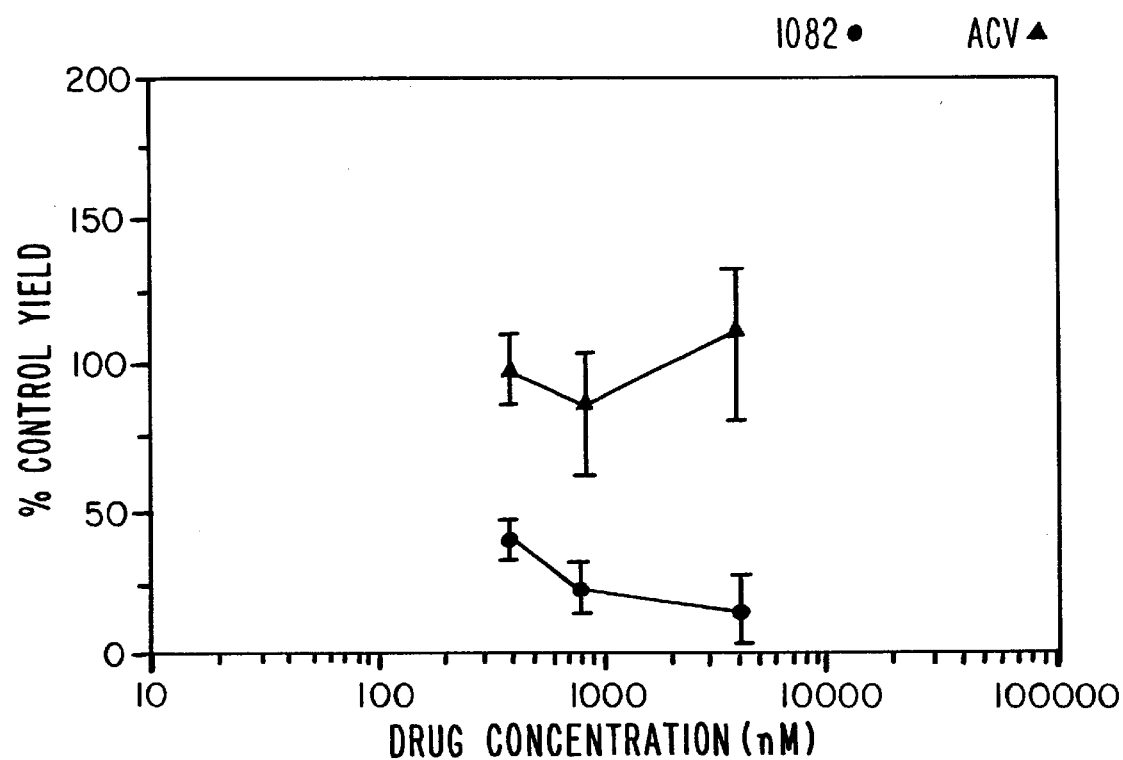

The antiviral efficacy of ISIS 1082 was examined using two $ACV^r$ strains of HSV-1, the DM2.1 strain which is devoid of the viral thymidine kinase gene and the $PAAr^5$ strain which expresses an altered nucleotide binding site in the viral DNA polymerase. Both virus strains were treated with ISIS 1082 at concentrations of 400 nM, 800 nM or 4 $\mu$M. For comparison, each strain was treated in parallel infections with the same concentrations of ACV. At the concentrations tested, ACV affected neither strain in a dose-dependent manner while treatment with ISIS 1082 inhibited viral yield of both strains in a dose-dependent manner (FIG. 15). The $IC_{50}$ values for ISIS 1082 were predicted from this data to be 300 nM and 600 nM with the DM2.1 and $PAAr^5$ strains of HSV-1, respectively. The reduction in yield of the DM2.1 strain at levels similar to those observed when treating other strains of HSV-1 (FIGS. 13, 14) or HSV-2 (FIG. 12) demonstrated that the antiviral effect of ISIS 1082 does not require phosphorylation of the oligonucleotide by the viral thymidine kinase enzyme.

Comparative Cellular Toxicities of ISIS 1082 and ACV

The cellular toxicities of ISIS 1082 and ACV were evaluated using a clonogenic assay in HeLa cells which reflected the time of compound exposure used for the infectious yield assays. At compound concentrations 100 uM, neither ISIS 1082 nor ACV caused a 50% reduction in the clonogenic capacity of HeLa cells in the assays. Using the average $IC_{50}$ values of 275 nM and 300 nM for ISIS 1082 and ACV, respectively, versus HSV-2 (FIG. 12), the Therapeutic Indices (TIs, TI=$LC_{50}/IC_{50}$) of the compounds were calculated to be >360 for ISIS 1082 and >334 for ACV. Thus, the predicted TI for ISIS 1082 from these studies was comparable to that of ACV.

What is claimed is:

1. A phosphorothioate or methylphosphonate oligonucleotide analog which comprises 15–50 bases, contains a sequence CAT and is capable of inhibiting activity of a herpesvirus, said oligonucleotide analog being complementary to a translation initiation portion of mRNA from a herpesvirus open reading frame selected from the group consisting of UL5, UL8, UL9, UL13, UL30, UL39, UL40, UL42 and UL52.

2. The oligonucleotide of claim 1 in a pharmaceutically acceptable carrier.

3. The oligonucleotide of claim 1 wherein at least some of the linking groups between nucleotide units of the oligonucleotide comprise phosphorothioate moieties.

4. An oligonucleotide consisting essentially of one of the sequences:

5'- 3'-

GGA CTC ATC CAT CCT TCG GCC, SEQ ID NO.:2,

GCG GCT GGC CAT TTC AAC AGA, SEQ ID NO.:3,

CGC GGA ATC CAT GGC AGC AGG, SEQ ID NO.:4,

ACC GAG GTC CAT GTC GTA CGC, SEQ ID NO.:5,

GGA CTC ATC CAT CCG TCC GCC, SEQ ID NO.:6,

GCC GAG GTC CAT GTC GTA CGC. SEQ ID NO.:7, and

GCG GTT GGC CAT TGG AAC CAA, SEQ ID NO.:8.

5. The oligonucleotide of claim 4 in a pharmaceutically acceptable carrier.

6. The oligonucleotide of claim 4 wherein at least some of the linking groups between nucleotide units of the oligonucleotide comprise phosphorothioate moieties.

7. A method of inhibiting the activity of a herpesvirus comprising directly injecting into a cell or tissue infected with the herpesvirus, an effective concentration of a phosphorothioate or methylphosphonate oligonucleotide analog 15–50 bases in length which contains a sequence CAT, said oligonucleotide analog being complementary to a translation initiation portion of mRNA from a herpesvirus open reading frame selected from the group consisting of UL5, UL8, UL9, UL13, UL30, UL39, UL40, UL42 and UL52 so that activity of the herpesvirus is inhibited.

8. The method of claim 7 wherein the herpesvirus is herpes simplex virus type 1, harps simplex virus type 2, cytomgalovirus, human herpes virus 6, Epstein Barr virus or varicella zoster virus.

9. The method of claim 7 wherein the oligonucleotide consists essentially of one of the sequences:

5'- 3'-

-continued

```
GGA CTC ATC CAT CCT TCG GCC,    SEQ ID NO.:2,

GCG GCT GGC CAT TTC AAC AGA,    SEQ ID NO.:3,

CGC GGA ATC CAT GGC AGC AGG,    SEQ ID NO.:4,

ACC GAG GTC CAT GTC GTA CGC,    SEQ ID NO.:5,

GGA CTC ATC CAT CCG TCC GCC,    SEQ ID NO.:6,

GCC GAG GTC CAT GTC GTA CGC.    SEQ ID NO.:7, and
```

-continued

```
GCG GTT GGC CAT TGG AAC CAA,    SEQ ID NO.:8.
```

10. The method of claim 7 wherein at least some of the linking groups between nucleotide units of the oligonucleotide comprise phosphorothioate moieties.

* * * * *